United States Patent
Chu et al.

(10) Patent No.: US 10,022,326 B2
(45) Date of Patent: Jul. 17, 2018

(54) LIPOSOMAL COMPOSITIONS OF EPOXYKETONE-BASED PROTEASOME INHIBITORS

(71) Applicant: ONYX THERAPEUTICS, INC., South San Francisco, CA (US)

(72) Inventors: Katherine A. Chu, San Francisco, CA (US); Elena T. Chan, San Mateo, CA (US); Ying Fang, Saratoga, CA (US); Mouhannad Jamaa, Foster City, CA (US); Christopher Justin Kirk, Milbrae, CA (US); Tony Muchamuel, Boulder Creek, CA (US); Zhengping Wang, San Mateo, CA (US); Jing Jiang, San Jose, CA (US); Jeffrey Joseph Jones, Redwood City, CA (US)

(73) Assignee: Onyx Therapeutics, Inc., Thousand Oaks, CA (US)

( * ) Notice: Subject to any disclaimer, the term of this patent is extended or adjusted under 35 U.S.C. 154(b) by 65 days.

(21) Appl. No.: 14/414,568

(22) PCT Filed: Jul. 17, 2013

(86) PCT No.: PCT/US2013/050872
§ 371 (c)(1),
(2) Date: Jan. 13, 2015

(87) PCT Pub. No.: WO2014/015027
PCT Pub. Date: Jan. 23, 2014

(65) Prior Publication Data
US 2015/0209282 A1 Jul. 30, 2015

Related U.S. Application Data

(60) Provisional application No. 61/794,603, filed on Mar. 15, 2013, provisional application No. 61/673,017, filed on Jul. 18, 2012.

(51) Int. Cl.
*A61K 9/127* (2006.01)
*A61K 38/07* (2006.01)
(Continued)

(52) U.S. Cl.
CPC ............ *A61K 9/127* (2013.01); *A61K 9/1271* (2013.01); *A61K 9/1277* (2013.01); *A61K 38/07* (2013.01);
(Continued)

(58) Field of Classification Search
CPC ...................................................... A61K 9/127
See application file for complete search history.

(56) References Cited

U.S. PATENT DOCUMENTS 4,235,871 A 11/1980 Papahadjopoulos et al.
4,535,152 A 8/1985 Szejtli et al.
(Continued)

FOREIGN PATENT DOCUMENTS

WO WO-1998/010779 A1 3/1998
WO WO-2003/028697 A2 4/2003

OTHER PUBLICATIONS

"Hydro Soy PC." Alvanti Lipids. Retrieved from http://avantilipids.com/product/840058/.*
(Continued)

*Primary Examiner* — Gollamudi Kishore
(74) *Attorney, Agent, or Firm* — Marshall, Gerstein & Borun LLP

(57) ABSTRACT

Liposomal compositions comprising peptide epoxyketone compounds are described, as well as methods of making and using such liposomal compositions. These liposomal compositions enhance the therapeutic window of peptide epoxyketone compounds by improving in vivo half-life relative to non-liposomal compositions comprising peptide epoxyketone compounds, providing desirable pharmacody-
(Continued)

namic profiles, and providing anti-tumor activity in a human tumor xenograft model, greater than or equal to non-liposomal compositions comprising peptide epoxyketone compounds. Further, experiments performed in support of the present invention demonstrated improved tolerability of liposomal compositions comprising peptide epoxyketone compounds.

26 Claims, 11 Drawing Sheets

(51) Int. Cl.
  A61K 45/06 (2006.01)
  A61K 47/22 (2006.01)
  A61K 47/48 (2006.01)
(52) U.S. Cl.
  CPC .............. *A61K 45/06* (2013.01); *A61K 47/22* (2013.01); *A61K 47/48969* (2013.01)

(56) References Cited

U.S. PATENT DOCUMENTS

| | | | |
|---|---|---|---|
| 4,544,545 A | 10/1985 | Ryan et al. | |
| 4,687,661 A | 8/1987 | Kikuchi et al. | |
| 4,727,064 A | 2/1988 | Pitha | |
| 4,737,323 A | 4/1988 | Martin et al. | |
| 4,789,633 A | 12/1988 | Huang et al. | |
| 4,920,214 A | 4/1990 | Friedman | |
| 5,013,556 A | 5/1991 | Woodle et al. | |
| 5,049,390 A | 9/1991 | Wojdani | |
| 5,089,181 A * | 2/1992 | Hauser .................. | A61K 9/127 264/4.1 |
| 5,134,127 A | 7/1992 | Stella et al. | |
| 5,173,481 A | 12/1992 | Pitha et al. | |
| 5,340,736 A | 8/1994 | Goldberg | |
| 5,385,891 A | 1/1995 | Moriya et al. | |
| 5,466,467 A | 11/1995 | Singh | |
| 5,527,528 A * | 6/1996 | Allen .................. | A61K 9/1271 424/178.1 |
| 5,534,241 A | 7/1996 | Torchilin et al. | |
| 5,593,622 A | 1/1997 | Yoshioka et al. | |
| 5,648,478 A | 7/1997 | Henderson | |
| 5,663,387 A | 9/1997 | Singh | |
| 5,676,971 A | 10/1997 | Yoshioka et al. | |
| 5,718,905 A | 2/1998 | Skiba et al. | |
| 5,756,069 A | 5/1998 | Torchilin et al. | |
| 5,759,573 A * | 6/1998 | Kim ........................ | A61K 9/127 424/450 |
| 5,780,052 A | 7/1998 | Khaw et al. | |
| 5,786,214 A | 7/1998 | Holmberg | |
| 5,830,686 A | 11/1998 | Henderson | |
| 5,834,012 A | 11/1998 | Perez-Soler et al. | |
| 5,837,282 A | 11/1998 | Fenske et al. | |
| 5,846,458 A | 12/1998 | Yoshioka et al. | |
| 5,891,468 A | 4/1999 | Martin et al. | |
| 5,945,122 A | 8/1999 | Abra et al. | |
| 6,004,534 A | 12/1999 | Langer et al. | |
| 6,046,177 A | 4/2000 | Stella et al. | |
| 6,056,973 A | 5/2000 | Allen et al. | |
| 6,057,299 A | 5/2000 | Henderson | |
| 6,077,834 A | 6/2000 | Cheng | |
| 6,110,666 A | 8/2000 | Grosveld et al. | |
| 6,126,966 A | 10/2000 | Abra et al. | |
| 6,177,059 B1 | 1/2001 | Matsuda et al. | |
| 6,245,427 B1 | 6/2001 | Duzgunes et al. | |
| 6,270,806 B1 | 8/2001 | Liversidge et al. | |
| 6,287,593 B2 | 9/2001 | Cherian | |
| 6,316,024 B1 | 11/2001 | Allen et al. | |
| 6,387,397 B1 | 5/2002 | Chen et al. | |
| 6,476,068 B1 | 11/2002 | Lauria et al. | |
| 6,524,613 B1 | 2/2003 | Steer et al. | |
| 6,530,944 B2 | 3/2003 | West et al. | |
| 6,586,559 B2 | 7/2003 | Ansell | |
| 6,627,218 B2 | 9/2003 | Huang et al. | |
| 6,723,338 B1 | 4/2004 | Sarris et al. | |
| 6,749,863 B1 | 6/2004 | Chang et al. | |
| 6,803,360 B1 | 10/2004 | Chang et al. | |
| 6,897,196 B1 | 5/2005 | Szoka, Jr. et al. | |
| 6,936,272 B2 | 8/2005 | Martin et al. | |
| 6,960,560 B2 | 11/2005 | Gwathmey | |
| 7,060,291 B1 | 6/2006 | Meers et al. | |
| 7,101,985 B2 | 9/2006 | Elledge et al. | |
| 7,122,202 B2 | 10/2006 | Allen et al. | |
| 7,311,924 B2 | 12/2007 | Sarris et al. | |
| 7,361,640 B2 | 4/2008 | Huang et al. | |
| 7,417,042 B2 | 8/2008 | Smyth et al. | |
| 7,737,112 B2 * | 6/2010 | Lewis .................. | A61K 9/0019 514/12.2 |
| 7,901,708 B2 | 3/2011 | MacLachlan et al. | |
| 2002/0119188 A1 | 8/2002 | Niemiec et al. | |
| 2002/0198164 A1 | 12/2002 | Henderson | |
| 2003/0027779 A1 | 2/2003 | Neuman et al. | |
| 2003/0072794 A1 | 4/2003 | Boulikas | |
| 2003/0082228 A1 | 5/2003 | Flowers et al. | |
| 2003/0143742 A1 | 7/2003 | Goomer | |
| 2003/0166601 A1 | 9/2003 | Woodle et al. | |
| 2003/0203865 A1 | 10/2003 | Harvie et al. | |
| 2003/0215490 A1 | 11/2003 | Allen et al. | |
| 2003/0220284 A1 | 11/2003 | Yotnda et al. | |
| 2003/0224037 A1 | 12/2003 | Eriguchi et al. | |
| 2003/0228285 A1 | 12/2003 | Hung et al. | |
| 2004/0022842 A1 | 2/2004 | Eriguchi et al. | |
| 2004/0234588 A1 | 11/2004 | Lu et al. | |
| 2005/0136064 A1 | 6/2005 | Allen et al. | |
| 2009/0092661 A1 * | 4/2009 | Huang .................. | A61K 9/1271 424/450 |
| 2009/0131367 A1 * | 5/2009 | Gore .................... | A61K 31/435 514/64 |
| 2011/0177156 A1 | 7/2011 | Szoka, Jr. et al. | |
| 2011/0236428 A1 | 9/2011 | Kirk et al. | |

OTHER PUBLICATIONS

"Product Information: Carfilzomib." Cayman Chemical. Retrieved from https://www.caymanchem.com/pdfs/17554.pdf.*

Adams, The proteasome: a suitable antineoplastic target, *Nature*, 4:349-60 (2004).

Avnir et al., Amphipathic weak acid glucocorticoid prodrugs remote-loaded into sterically stabilized nanoliposomes evaluated in arthritic rats and in a Beagle dog: a novel approach to treating autoimmune arthritis, *Arthritis & Rheumatism*, 58(1):119-29 (2008).

Braun et al., Targeting NF-kappaB in hematologic malignancies, *Cell Death Differ.*, 13:748-58 (2006).

Chapatte et al., Processing of tumor-associated antigen by the proteasomes of dendritic cells controls in vivo T-cell responses, *Cancer Res.*, 66:5461-8 (2006).

Ciechanover, The ubiquitin-proteasome proteolytic pathway, *Cell*, 79:13-21 (1994).

Cilloni et al., Nuclear factor κB as a target for new drug development in myeloid malignancies, *Haematologica*, 92:1224-1229 (2007).

Cohen, AIDS Mood Upbeat—For a Changes, *Science*, 267:959-60 (1995).

Collins, Endothelial nuclear factor-kappa B and the initiation of the atherosclerotic lesion, *Lab. Invest.*, 68:499-508 (1993).

Dos Santos et al., pH gradient loading of anthracyclines into cholesterol-free liposomes: enhancing drug loading rates through use of ethanol, *Biochim. Biophys. Acta.*, 1661:47-60 (2004).

Garrett et al., Selective inhibitors of the osteoblast proteasome stimulate bone formation in vivo and in vitro, *J. Clin. Invest.*, 111:1771-1782 (2003).

Gonzales et al., Proteasome function is required for encystation of Entamoeba invadens, *Arch. Med. Res.*, 28, Spec No. 139-140 (1997).

Gould et al., 2-Hydroxypropyl-beta-cyclodextrin (HP-beta-CD): a toxicology review, *Food Chem. Toxicol.*, 43(10):1451-9 (2005).

(56) References Cited

OTHER PUBLICATIONS

Hardy et al., The secret life of the hair follicle, *Trans. Genet.*, 8:55-61 (1992).
Harris et al., Comparison of the internal energy deposition of direct analysis in real time and electrospray ionization time-of-flight mass spectrometry, *J. Bone Miner. Res.*, 9:855-63 (1994).
Kojima et al., Two-way cleavage of β-amyloid protein precursor by multicatalytic proteinase, *Fed. Eur. Biochem. Soc.*, 304:57-60 (1992).
Kumatori et al., Abnormally high expression of proteasomes in human leukemic cells, *Proc. Natl. Acad. Sci. USA*, 87:7071-5 (1990).
Lightcap et al., Proteasome inhibition measurements: clinical application, *Clin. Chem.*, 46:673-83 (2000).
Palombella et al., The ubiquitin-proteasome pathway is required for processing the NF-kappa B1 precursor protein and the activation of NF-kappa B, *Cell*, 78:773-85 (1994).
Paugam, et al., Characterization and role of protozoan parasite proteasomes, *Trends Parasitol.*, 19(2):55-9(2003).
Petrakis et al., Scaling Dimensions of Nitrogen Adsorption Characteristics in Modulated Mesoporous Aluminophosphates, *J. Colloid and Interface Sci.*, 185(1):104-110 (1997).
Qureshi et al., The proteasome as a lipopolysaccharide-binding protein in macrophages: differential effects of proteasome inhibition on lipopolysaccharide-induced signaling events, *J. Immun.*, 171:1515-25 (2003).
Ramsay et al., Transition metal-mediated liposomal encapsulation of irinotecan (CPT-11) stabilizes the drug in the therapeutically active lactone conformation, *Pharm. Res.*, 23(12):2799-808 (2006).
Rolfe, et al., The ubiquitin-mediated proteolytic pathway as a therapeutic area, *J. Mol. Med.*, 75:5-17 (1997).
Simsek et al., Hepatitis B virus large and middle glycoproteins are degraded by a proteasome pathway in glucosidase-inhibited cells but not in cells with functional glucosidase enzyme, *J. Virol.*, 79:12914-20 (2005).
Stella et al., Cyclodextrins, *Toxicol. Pathol.*, 36(1):30-42 (2008).
Szalay et al., Ongoing coxsackievirus myocarditis is associated with increased formation and activity of myocardial immunoproteasomes, *Am. J. Pathol.*, 168:1542-52 (2006).
Szoka et al., Comparative Properties and Methods of Preparation of Lipid Vesicles (Liposomes), *Annu. Rev. Biophys. Bioeng.*, 9:467-508 (1980).
Thanos et al., NF-kappa B: a lesson in family values, *Cell*, 80:529-32 (1995).
Traenckner et al., A proteasome inhibitor prevents activation of NF-kappa B and stabilizes a newly phosphorylated form of I kappa B-alpha that is still bound to NF-kappa B, *EMBO J.* 13:5433-41 (1994).
Vemuri et al., Development and characterization of a liposome preparation by a pH-gradient method, *J. Pharm. Pharmacol.*, 46(10):778-83 (1994).
Yu et al., The ubiquitin-proteasome system facilitates the transfer of murine coronavirus from endosome to cytoplasm during virus entry, *J. Virol.*, 79:644-8 (2005).
International Preliminary Report on Patentability, PCT/US2013/050872, dated Jan. 20, 2015.
International Search Report and Written Opinion of the International Search Authority, PCT/US2013/050872, dated Nov. 29, 2013.

\* cited by examiner

| Lot | Composition | CFZ (mg) | EPC (mg) | mPEG (mg) | Cholesterol (mg) | Drug:Lipid Ratio (%) | Lipid Conc (mg/mL) | mPEG Conc (mg/mL) | Cholesterol Conc. (mg/mL) | Rehydration Volume (ml) | Theoretical Conc (mg/ml) | Avg Conc (mg/ml) | n = | % Diff | SD | % RSD |
|---|---|---|---|---|---|---|---|---|---|---|---|---|---|---|---|---|
| 6005-27B | A | 0 | 104.1 | 0 | 0 | 0 | 13.0 | 0 | 0 | 8 | 0 | 0 | N/A | N/A | N/A | N/A |
| 6005-29C | B | 5.8 | 111.3 | 0 | 0 | 5% | 13.9 | 0 | 0 | 8 | 0.73 | 0.81 | 3 | 12 | 0.008 | 0.95 |
| 6005-35B | D | 0 | 91.39 | 10.31 | 0 | 0 | 11.4 | 1.3 | 0 | 8 | 0 | 0 | 1 | N/A | N/A | N/A |
| 6005-45A | C | 17.2 | 112.3 | 0 | 0 | 13% | 14.0 | 0 | 0 | 8 | 2.15 | N/A | N/A | N/A | N/A | N/A |
| 6005-45B | C | 16.5 | 105.5 | 0 | 0 | 14% | 13.2 | 0 | 0 | 8 | 2.06 | N/A | N/A | N/A | N/A | N/A |
| 6005-45A.B Pooled | C | N/A | N/A | N/A | 0 | N/A | N/A | 0 | 0 | N/A | N/A | 1.97 | 3 | N/A | 0.004 | 0.2 |
| 6005-45C | E | 17 | 94.6 | 12.7 | 0 | 15% | 11.8 | 1.6 | 0 | 8 | 2.13 | N/A | N/A | N/A | N/A | N/A |
| 6005-45D | E | 16 | 93.9 | 11.5 | 0 | 15% | 11.7 | 1.4 | 0 | 8 | 2.00 | N/A | N/A | N/A | N/A | N/A |
| 6005-45CCD Pooled | E | N/A | N/A | N/A | 0 | N/A | N/A | 0 | 0 | N/A | N/A | 2.06 | 3 | N/A | 0.104 | 5.0300 |
| 6005-53A | C | 22.6 | 130.6 | 0 | 0 | 15% | 13.1 | 0 | 0 | 10 | 2.26 | 2.31 | 3 | 2 | 0.015 | 0.63 |
| 6005-53D | C | 41.9 | 251.8 | 0 | 0 | 14% | 12.6 | 0 | 0 | 20 | 2.10 | 2.10 | 3 | 0 | 0.012 | 0.59 |
| 6005-53A-D Pooled | C | N/A | N/A | N/A | 0 | N/A | N/A | 0 | 0 | N/A | N/A | 2.04 | 3 | N/A | 0.108 | 5.29 |
| 6005-53C | A | 0 | 129.8 | 0 | 0 | 0 | 13.0 | 0 | 0 | 10 | 0 | 0 | N/A | N/A | N/A | N/A |
| 6005-67B | C | 41.7 | 252.9 | 0 | 0 | 14% | 12.6 | 0 | 0 | 20 | 2.09 | 2.10 | 3 | 1 | 0.006 | 0.27 |
| 6005-69A | C | 21.3 | 126.9 | 0 | 0 | 14% | 12.7 | 0 | 0 | 10 | 2.13 | 2.18 | 3 | 2 | 0.02 | 0.96 |
| 6005-69B | A | 0 | 125.9 | 0 | 0 | 0 | 12.6 | 0 | 0 | 10 | 0 | 0 | 1 | N/A | N/A | N/A |
| 6005-71D | F | 0 | 124.5 | 13.2 | 31.4 | 0 | 12.5 | 1.3 | 3.1 | 10 | 0 | 0 | 1 | N/A | N/A | N/A |
| 6005-71E | G | 20.0 | 127.2 | 13.6 | 31.6 | 14% | 12.7 | 1.4 | 3.2 | 10 | 2.0 | 1.97 | 3 | 1.5 | .01 | 0.24 |

FIG. 1

LIPOSOMAL COMPOSITIONS OF EPOXYKETONE-BASED PROTEASOME INHIBITORS

CROSS-REFERENCE TO RELATED APPLICATIONS

This application claims the benefit of U.S. Provisional Application Ser. No. 61/673,017, filed 18 Jul. 2012, and U.S. Provisional Application Ser. No. 61/794,603, filed 15 Mar. 2013, both of which applications are herein incorporated by reference in their entireties.

TECHNICAL FIELD

The present invention relates generally to pharmaceutical liposomal compositions comprising peptide epoxyketone compounds. Aspects of the present invention include, but are not limited to, methods for making stable pharmaceutical liposomal compositions comprising peptide epoxyketone compounds, methods of using pharmaceutical liposomal compositions, and dry pharmaceutical compositions comprising peptide epoxyketone compounds made from the pharmaceutical liposomal compositions.

BACKGROUND OF THE INVENTION

In eukaryotes, protein degradation is predominately mediated through the ubiquitin pathway in which proteins targeted for destruction are ligated to the 76 amino acid polypeptide ubiquitin. Once targeted, ubiquitinated proteins then serve as substrates for the 26S proteasome, a multi-catalytic protease, which cleaves proteins into short peptides through the action of its three major proteolytic activities. While having a general function in intracellular protein turnover, proteasome-mediated degradation also plays a key role in many processes such as major histocompatibility complex (MHC) class I presentation, apoptosis, cell growth regulation, NF-κB activation, antigen processing, and transduction of pro-inflammatory signals.

The 20S proteasome is a 700 kDa cylindrical-shaped multicatalytic protease complex comprised of 28 subunits organized into four rings. In yeast and other eukaryotes, 7 different α subunits form the outer rings and 7 different β subunits comprise the inner rings. The α subunits serve as binding sites for the 19S (PA700) and 11S (PA28) regulatory complexes, as well as a physical barrier for the inner proteolytic chamber formed by the two β subunit rings. Thus, in vivo, the proteasome is believed to exist as a 26S particle ("the 26S proteasome"). In vivo experiments have shown that inhibition of the 20S form of the proteasome can be readily correlated to inhibition of 26S proteasome. Cleavage of amino-terminal prosequences of β subunits during particle formation exposes amino-terminal threonine residues, which serve as the catalytic nucleophiles.

The subunits responsible for catalytic activity in proteasomes thus possess an amino terminal nucleophilic residue, and these subunits belong to the family of N-terminal nucleophile (Ntn) hydrolases (where the nucleophilic N-terminal residue is, for example, Cys, Ser, Thr, or other nucleophilic moieties). This family includes, for example, penicillin G acylase (PGA), penicillin V acylase (PVA), glutamine PRPP amidotransferase (GAT), and bacterial glycosylasparaginase. In addition to the ubiquitously expressed β subunits, higher vertebrates also possess three interferon-γ-inducible β subunits (LMP7, LMP2 and MECL1), which replace their normal counterparts, β5, β1 and β2 respectively, thus altering the catalytic activities of the proteasome.

Through the use of different peptide substrates, three major proteolytic activities have been defined for the eukaryote 20S proteasome: chymotrypsin-like activity (CT-L), which cleaves after large hydrophobic residues; trypsin-like activity (T-L), which cleaves after basic residues; and caspase-like (C-L), which cleaves after acidic residues. The major proteasome proteolytic activities appear to be contributed by different catalytic sites, because inhibitors, point mutations in β subunits, and the exchange of interferon-γ-inducing β subunits alter these activities to various degrees.

There are several examples of small molecules that have been used to inhibit proteasome activity and have been shown to be effective against cancer, particularly multiple myeloma. However, unlike the peptide epoxyketone compounds described herein, these compounds generally lack the specificity, stability, or potency necessary to explore and exploit the roles of the proteasome at the cellular and molecular level, and thus maximize their therapeutic activity.

SUMMARY OF THE INVENTION

The present invention generally relates to pharmaceutical liposomal compositions comprising a peptide epoxyketone compound, methods of making such liposomal compositions, methods of using such liposomal compositions, dry pharmaceutical compositions comprising a peptide epoxyketone compound, and methods of making and using such dry pharmaceutical compositions.

In one aspect, the present invention relates to pharmaceutical liposomal compositions. In some embodiments, the pharmaceutical liposomal compositions comprise liposome entrapped peptide epoxyketone compound. Such pharmaceutical compositions typically comprise an aqueous solution comprising liposomes, wherein the liposomes comprise between about 0.5 wt. % and about 50 wt. % of a peptide epoxyketone compound, and between about 99.5 wt. % and about 50 wt. % total lipids (weight ratio of peptide epoxyketone compound:total lipids of between about 0.005:0.995 and about 0.5:0.5).

In preferred embodiments the total lipids comprise a phospholipid, for example, L-α-phosphatidylcholine, 1,2-distearoyl-sn-glycero-3-phosphocholine, 1,2-dipalmitoyl-sn-glycero-3-phosphocholine, 1,2-Distearoyl-sn-glycero-3-phospho-rac-(1-glycerol), 1-Palmitoyl-2-oleoyl-sn-glycero-3-phosphocholine, sphingomyelin, 1,2-distearoyl-sn-glycero-3-phosphoethanolamine, as well as combinations thereof. Total lipids can further comprise, for example, a hydrophilic polymer-derivatized lipid, and/or a cholesterol or cholesterol derivative.

The liposomes of the liposomal compositions comprising peptide epoxyketone compounds typically have an average size of between about 0.05 microns and about 0.5 microns.

In some embodiments of the present invention, the liposomal compositions comprise liposomes comprising the peptide epoxyketone compound and a solubilizing agent in an internal aqueous core of the liposomes. In some embodiments, the solubilizing agent is a compound (e.g., a cyclodextrin), and the liposomes of the liposomal composition comprise the peptide epoxyketone compound complexed with the compound (e.g., a cyclodextrin) in the internal aqueous core of the liposomes.

The pharmaceutical liposomal compositions of the present invention can also include one or more excipients.

In other aspects, the present invention relates to dry pharmaceutical compositions comprising peptide epoxyketone compounds. Such dry pharmaceutical compositions are typically made by dehydration of the pharmaceutical liposomal compositions described here.

In yet further aspects, the present invention relates to methods of making the pharmaceutical liposomal compositions described herein. One method of making a pharmaceutical liposomal composition comprises preparing a dried film comprising total lipids, and rehydrating the dried film with an aqueous solution comprising a peptide epoxyketone compound to form a liposomal composition comprising liposomes dispersed in aqueous solution. Typically the aqueous solution comprises a peptide epoxyketone compound and a solubilizing agent. Another method of making a pharmaceutical liposomal composition comprises preparing a lipid solution comprising total lipids and a solvent, and injecting the lipid solution into an aqueous solution comprising a peptide epoxyketone compound. Typically the aqueous solution comprises a peptide epoxyketone compound and a solubilizing agent.

In some embodiments, peptide epoxyketone compounds not encapsulated in liposomes are removed from the pharmaceutical liposomal compositions.

In other aspects, the present invention relates to pharmaceutical liposomal compositions comprising peptide epoxyketone compounds made by the methods of the invention, dry pharmaceutical compositions made therefrom, as well as reconstituted liposomal compositions comprising peptide epoxyketone compounds made from the dry pharmaceutical compositions.

In further aspects, the present invention relates to methods of treating a disease or condition in a subject in need of treatment, comprising administering a therapeutically effective amount of a pharmaceutical liposomal composition comprising liposomes comprising a peptide epoxyketone compound. In some embodiments the methods of treating further comprise simultaneous, sequential, or separate administration of a therapeutically effective amount of another therapeutic agent, for example, a chemotherapeutic agent, a cytokine, a steroid, an immunotherapeutic agent, or combinations thereof.

These and other embodiments of the present invention will readily occur to those of ordinary skill in the art in view of the disclosure herein.

BRIEF DESCRIPTION OF THE FIGURES

FIG. 1 presents specific experimental formulations and HPLC characterization data of selected, exemplary liposomal compositions (Compositions A to G; Table 2A), which were used to generate associated data presented in the Examples and Tables herein. The nominal concentrations of exemplary liposomal Compositions A to G are presented in Table 2A. Note that the drug to lipid ratios in FIG. 1 (Drug:Lipid Ratio (%)) were calculated by taking the weight of drug (carfilzomib) divided by the weight of drug plus weight of phospholipid; however, the more conventional calculation is a ratio of the weight of drug to the weight of total lipids (e.g. phospholipid, hydrophilic polymer-derivatized lipid, cholesterol; see, e.g., Table 3). The more conventional calculation of Drug:Total Lipid Ratio for the specific experimental formulations in FIG. 1 are presented in Table 2B. The columns for the HPLC characterization data are as follows: "n" is the number of replicate samples assayed; "% Diff" is the percent difference between the theoretical drug concentration and the average experimental drug concentration; "SD" is the standard deviation of the experimentally determined drug concentration; and "% RSD" is the percent relative standard deviation of the experimentally determined drug concentration. The rows of "Pooled" data in FIG. 1 represent instances where two separate batches of a particular liposomal composition were combined into a single batch liposomal composition (see, e.g., "6005-45A/B Pooled" represents a liposomal Composition C prepared by combining Composition C (6005-45A) and Composition C (6005-45B)).

DETAILED DESCRIPTION OF THE INVENTION

Figure 2A:
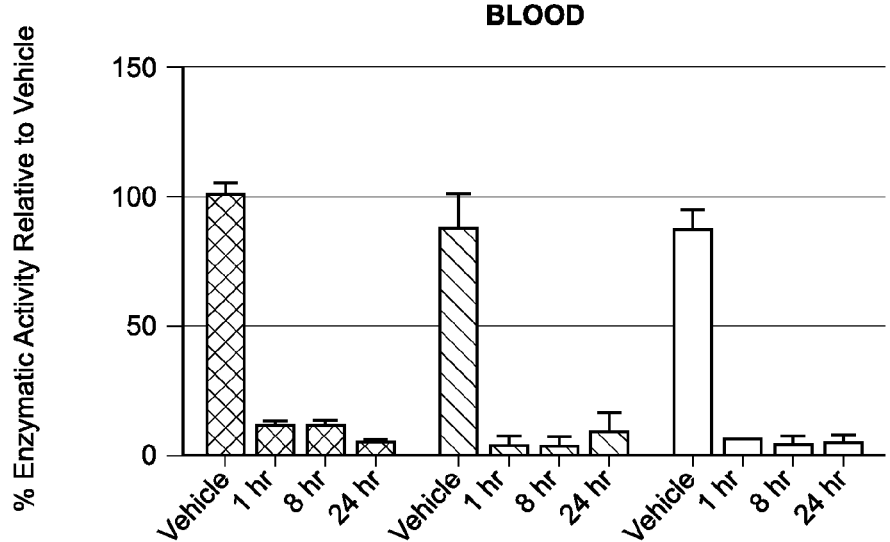
FIG. 2A presents data related to pharmacodynamic responses in BALB/C mice to different compositions of carfilzomib. In the figure, the vertical axis is the percent (%) enzymatic activity relative to vehicle, wherein the enzymatic activity corresponds to proteasome CT-L activity in whole blood (primarily erythrocytes). Three groups of data are presented on the horizontal axis as follows. The first group, represented in the figure as cross-hatched bars, presents data for an injectable composition of carfilzomib (CFZ) formulated in 10% sulfobutylether beta cyclodextrin (SBE-β-CD, also referred to herein as SBE-B-CD), and 10 mM Citrate, pH 3.5 (non-liposomal): the first bar presents control data for the placebo vehicle without carfilzomib, the second bar presents data for CFZ SBE-B-CD at 1 hour, the third bar presents data for CFZ SBE-B-CD at 8 hours, and the fourth bar presents data for CFZ SBE-B-CD at 24 hours. The second group, represented in the figure as diagonal-lined bars, presents data for a liposomal composition of carfilzomib (liposomes comprising CFZ (L-CFZ, Composition C)): the first bar presents control data for the liposomal vehicle without carfilzomib, the second bar presents data for the carfilzomib liposomal composition at 1 hour, the third bar presents data for the carfilzomib liposomal composition at 8 hours, and the fourth bar presents data for the carfilzomib liposomal composition at 24 hours. The third group, represented in the figure as white, outlined bars, presents data for a pegylated liposomal composition of carfilzomib (pegylated liposomes comprising (pL-CFZ, Composition E)): the first bar presents control data for the pegylated liposomal vehicle without carfilzomib, the second bar presents data for the carfilzomib pegylated liposomal composition at 1 hour, the third bar presents data for the carfilzomib pegylated liposomal composition at 8 hours, and the fourth bar presents data for the carfilzomib pegylated liposomal composition at 24 hours. Error bars are represented unidirectionally.
Figure 2B:
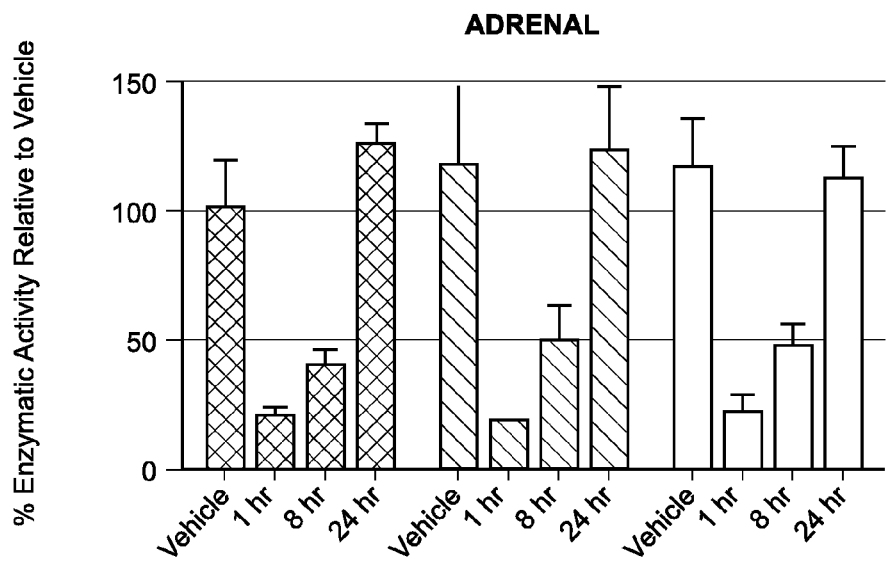
FIG. 2B presents data related to pharmacodynamic responses in BALB/C mice to different compositions of carfilzomib. In the figure, the vertical axis is the percent (%) enzymatic activity relative to vehicle, wherein the enzymatic activity corresponds to proteasome CT-L activity in adrenal tissue. Three groups of data are presented on the horizontal axis as follows. The first group, represented in the figure as cross-hatched bars, presents data for injectable CFZ SBE-B-CD (non-liposomal): the first bar presents control data for the vehicle without carfilzomib, the second bar presents data for CFZ SBE-B-CD at 1 hour, the third bar presents data for CFZ SBE-B-CD at 8 hours, and the fourth bar presents data for CFZ SBE-B-CD at 24 hours. The second group, represented in the figure as diagonal-lined bars, presents data for a liposomal composition of carfilzomib (liposomes comprising CFZ (L-CFZ, Composition C)): the first bar presents control data for the liposomal vehicle without carfilzomib, the second bar presents data for the carfilzomib liposomal composition at 1 hour, the third bar presents data for the carfilzomib liposomal composition at 8 hours, and the fourth bar presents data for the carfilzomib liposomal composition at 24 hours. The third group, represented in the figure as white, outlined bars, presents data for a pegylated liposomal composition of carfilzomib (pegylated liposomes comprising (pL-CFZ, Composition E)): the first bar presents control data for the pegylated liposomal vehicle without carfilzomib, the second bar presents data for the carfilzomib pegylated liposomal composition at 1 hour, the third bar presents data for the carfilzomib pegylated liposomal composition at 8 hours, and the fourth bar presents data for the carfilzomib pegylated liposomal composition at 24 hours. Error bars are represented unidirectionally.
Figure 2C:
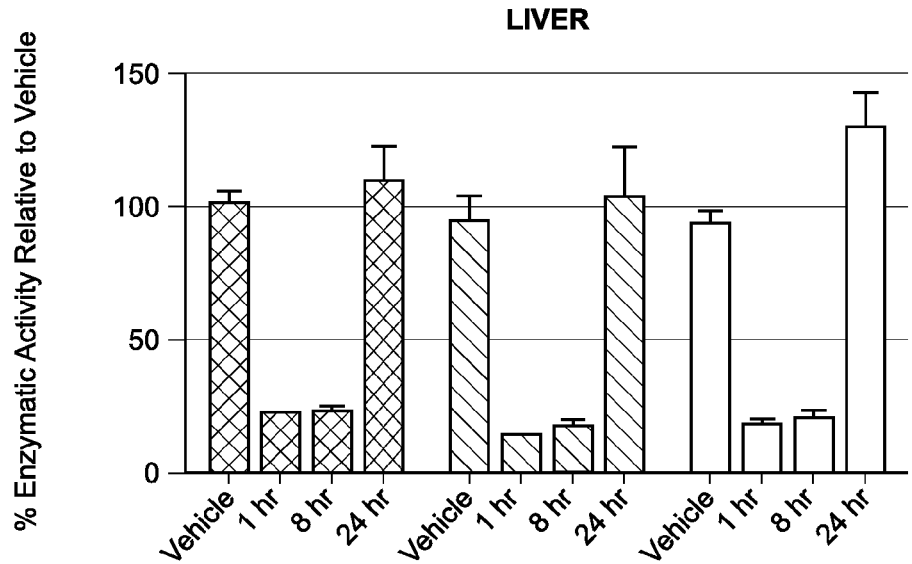
FIG. 2C presents data related to pharmacodynamic responses in BALB/C mice to different compositions of carfilzomib. In the figure, the vertical axis is the percent (%) enzymatic activity relative to vehicle, wherein the enzymatic activity corresponds to proteasome CT-L activity in liver tissue. Three groups of data are presented on the horizontal axis as follows. The first group, represented in the figure as cross-hatched bars, presents data for injectable CFZ SBE-B-CD (non-liposomal): the first bar presents control data for the vehicle without carfilzomib, the second bar presents data for the carfilzomib SBE-B-CD composition at 1 hour, the third bar presents data for the carfilzomib composition at 8 hours, and the fourth bar presents data for the carfilzomib composition at 24 hours. The second group, represented in the figure as diagonal-lined bars, presents data for a liposomal composition of carfilzomib (liposomes comprising CFZ (L-CFZ, Composition C)): the first bar presents control data for the liposomal vehicle without carfilzomib, the second bar presents data for the carfilzomib liposomal composition at 1 hour, the third bar presents data for the carfilzomib liposomal composition at 8 hours, and the fourth bar presents data for the carfilzomib liposomal composition at 24 hours. The third group, represented in the figure as white, outlined bars, presents data for a pegylated liposomal composition of carfilzomib (pegylated liposomes comprising (pL-CFZ, Composition E)): the first bar presents control data for the pegylated liposomal vehicle without carfilzomib, the second bar presents data for the carfilzomib pegylated liposomal composition at 1 hour, the third bar presents data for the carfilzomib pegylated liposomal composition at 8 hours, and the fourth bar presents data for the carfilzomib pegylated liposomal composition at 24 hours. Error bars are represented unidirectionally.
Figure 2D:
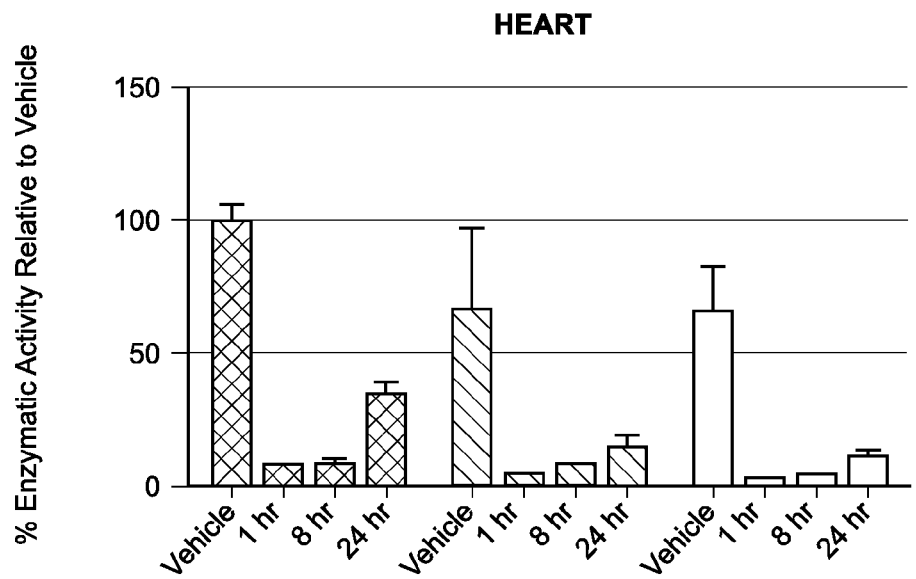
FIG. 2D presents data related to pharmacodynamic responses in BALB/C mice to different compositions of carfilzomib. In the figure, the vertical axis is the percent (%) enzymatic activity relative to vehicle, wherein the enzymatic activity corresponds to proteasome CT-L activity in heart tissue. Three groups of data are presented on the horizontal axis as follows. The first group, represented in the figure as cross-hatched bars, presents data for injectable CFZ SBE-B-CD (non-liposomal): the first bar presents control data for the vehicle without carfilzomib, the second bar presents data for CFZ SBE-B-CD at 1 hour, the third bar presents data for CFZ SBE-B-CD at 8 hours, and the fourth bar presents data for CFZ SBE-B-CD at 24 hours. The second group, represented in the figure as diagonal-lined bars, presents data for a liposomal composition of carfilzomib (liposomes comprising CFZ (L-CFZ, Composition C)): the first bar presents control data for the liposomal vehicle without carfilzomib, the second bar presents data for the carfilzomib liposomal composition at 1 hour, the third bar presents data for the carfilzomib liposomal composition at 8 hours, and the fourth bar presents data for the carfilzomib liposomal composition at 24 hours. The third group, represented in the figure as white, outlined bars, presents data for a pegylated liposomal composition of carfilzomib (pegylated liposomes comprising (pL-CFZ, Composition E)): the first bar presents control data for the pegylated liposomal vehicle without carfilzomib, the second bar presents data for the carfilzomib pegylated liposomal composition at 1 hour, the third bar presents data for the carfilzomib pegylated liposomal composition at 8 hours, and the fourth bar presents data for the carfilzomib pegylated liposomal composition at 24 hours. Error bars are represented unidirectionally.
Figure 3A:
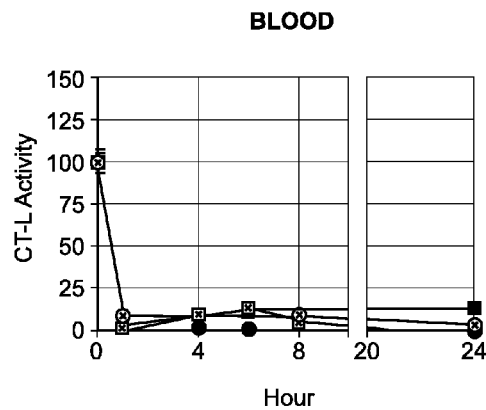
FIG. 3A presents data related to pharmacodynamic responses in BALB/C mice to different compositions of carfilzomib. In the figure, the vertical axis (CT-L activity) is the percent (%) enzymatic activity relative to a corresponding vehicle without carfilzomib (CFZ), wherein the enzymatic activity corresponds to proteasome CT-L activity in whole blood (primarily erythrocytes). The horizontal axis is the time in hours (Hour). Four groups of data are presented. The first group (open squares containing an X) presents data for an injectable composition of carfilzomib (CFZ) formulated in 10% sulfobutylether beta cyclodextrin (SBE-B-CD), and 10 mM Citrate, pH 3.5, (non-liposomal) administered at 5 mg/kg with data points at 0, 1, 4, 6, 8, and 24 hours. The second group (open circles containing an X) presents data for an injectable composition of carfilzomib (CFZ) formulated in 10% sulfobutylether beta cyclodextrin (SBE-B-CD), and 10 mM Citrate, pH 3.5, (non-liposomal) administered at 10 mg/kg with data points at 0, 1, 8, and 24 hours. The third group (solid squares) presents data for a pegylated liposomal composition of carfilzomib wherein the aqueous core of the pegylated liposomes comprises carfilzomib and SBE-B-CD (ap-L11) administered at 5 mg/kg with data points at 0, 1, 4, 6, and 24 hours. The fourth group (solid circles) presents data for a pegylated liposomal composition of carfilzomib wherein the aqueous core of the pegylated liposomes comprises carfilzomib and SBE-B-CD (ap-L11) administered at 15 mg/kg with data points at 0, 1, 4, 6, and 24 hours. Error bars are represented unidirectionally.
Figure 3B:
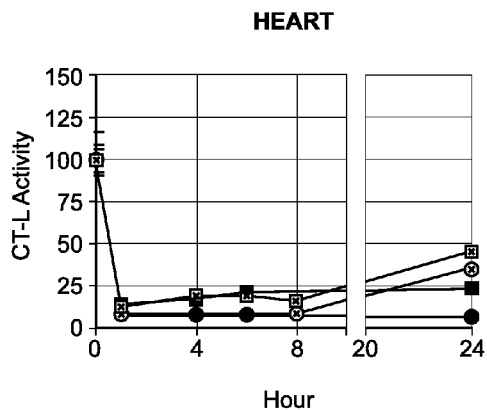
FIG. 3B presents data related to pharmacodynamic responses in BALB/C mice to different compositions of carfilzomib. In the figure, the vertical axis (CT-L activity) is the percent (%) enzymatic activity relative to a corresponding vehicle without carfilzomib (CFZ), wherein the enzymatic activity corresponds to proteasome CT-L activity in heart tissue. The horizontal axis is the time in hours (Hour). Four groups of data are presented. The first group (open squares containing an X) presents data for an injectable composition of carfilzomib (CFZ) formulated in 10% sulfobutylether beta cyclodextrin (SBE-B-CD), and 10 mM Citrate, pH 3.5, (non-liposomal) administered at 5 mg/kg with data points at 0, 1, 4, 6, 8, and 24 hours. The second group (open circles containing an X) presents data for an injectable composition of carfilzomib (CFZ) formulated in 10% sulfobutylether beta cyclodextrin (SBE-B-CD), and 10 mM Citrate, pH 3.5, (non-liposomal) administered at 10 mg/kg with data points at 0, 1, 8, and 24 hours. The third group (solid squares) presents data for a pegylated liposomal composition of carfilzomib wherein the aqueous core of the pegylated liposomes comprises carfilzomib and SBE-B-CD (ap-L11) administered at 5 mg/kg with data points at 0, 1, 4, 6, and 24 hours. The fourth group (solid circles) presents data for a pegylated liposomal composition of carfilzomib wherein the aqueous core of the pegylated liposomes comprises carfilzomib and SBE-B-CD (ap-L11) administered at 15 mg/kg with data points at 0, 1, 4, 6, and 24 hours. Error bars are represented unidirectionally.
Figure 3C:
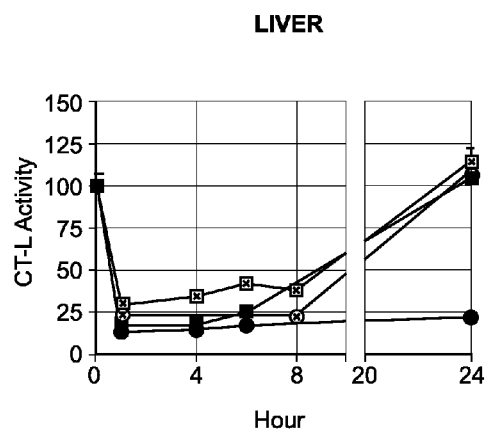
FIG. 3C presents data related to pharmacodynamic responses in BALB/C mice to different compositions of carfilzomib. In the figure, the vertical axis (CT-L activity) is the percent (%) enzymatic activity relative to a corresponding vehicle without carfilzomib (CFZ), wherein the enzymatic activity corresponds to proteasome CT-L activity in liver tissue. The horizontal axis is the time in hours (Hour). Four groups of data are presented. The first group (open squares containing an X) presents data for an injectable composition of carfilzomib (CFZ) formulated in 10% sulfobutylether beta cyclodextrin (SBE-B-CD), and 10 mM Citrate, pH 3.5, (non-liposomal) administered at 5 mg/kg with data points at 0, 1, 4, 6, 8, and 24 hours. The second group (open circles containing an X) presents data for an injectable composition of carfilzomib (CFZ) formulated in 10% sulfobutylether beta cyclodextrin (SBE-B-CD), and 10 mM Citrate, pH 3.5, (non-liposomal) administered at 10 mg/kg with data points at 0, 1, 8, and 24 hours. The third group (solid squares) presents data for a pegylated liposomal composition of carfilzomib wherein the aqueous core of the pegylated liposomes comprises carfilzomib and SBE-B-CD (ap-L11) administered at 5 mg/kg with data points at 0, 1, 4, 6, and 24 hours. The fourth group (solid circles) presents data for a pegylated liposomal composition of carfilzomib wherein the aqueous core of the pegylated liposomes comprises carfilzomib and SBE-B-CD (ap-L11) administered at 15 mg/kg with data points at 0, 1, 4, 6, and 24 hours. Error bars are represented unidirectionally.
Figure 3D:
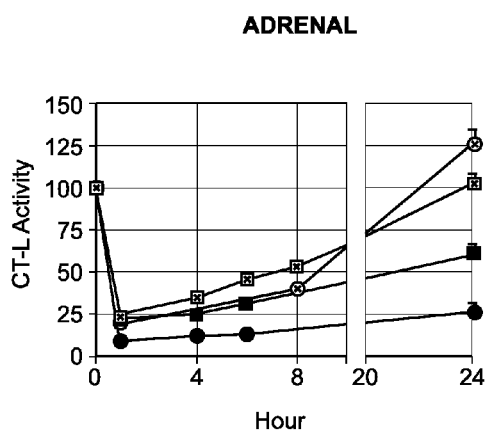
FIG. 3D presents data related to pharmacodynamic responses in BALB/C mice to different compositions of carfilzomib. In the figure, the vertical axis (CT-L activity) is the percent (%) enzymatic activity relative to a corresponding vehicle without carfilzomib (CFZ), wherein the enzymatic activity corresponds to proteasome CT-L activity in adrenal tissue. The horizontal axis is the time in hours (Hour). Four groups of data are presented. The first group (open squares containing an X) presents data for an injectable composition of carfilzomib (CFZ) formulated in 10% sulfobutylether beta cyclodextrin (SBE-B-CD), and 10 mM Citrate, pH 3.5, (non-liposomal) administered at 5 mg/kg with data points at 0, 1, 4, 6, 8, and 24 hours. The second group (open circles containing an X) presents data for an injectable composition of carfilzomib (CFZ) formulated in 10% sulfobutylether beta cyclodextrin (SBE-B-CD), and 10 mM Citrate, pH 3.5, (non-liposomal) administered at 10 mg/kg with data points at 0, 1, 8, and 24 hours. The third group (solid squares) presents data for a pegylated liposomal composition of carfilzomib wherein the aqueous core of the pegylated liposomes comprises carfilzomib and SBE-B-CD (ap-L11) administered at 5 mg/kg with data points at 0, 1, 4, 6, and 24 hours. The fourth group (solid circles) presents data for a pegylated liposomal composition of carfilzomib wherein the aqueous core of the pegylated liposomes comprises carfilzomib and SBE-B-CD (ap-L11) administered at 15 mg/kg with data points at 0, 1, 4, 6, and 24 hours. Error bars are represented unidirectionally.

All patents, publications, and patent applications cited in this specification are herein incorporated by reference as if each individual patent, publication, or patent application was specifically and individually indicated to be incorporated by reference in its entirety for all purposes.

1.0.0 Definitions

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a lipid" includes one or more lipids, or mixtures of lipids; reference to "a phospholipid" includes one or more lipids, or mixtures of phospholipids; reference to "a cholesterol or cholesterol derivative" includes one or more cholesterol or cholesterol derivative, or mixtures of a cholesterol and a cholesterol derivative; reference to "a hydrophilic polymer-derivatized lipid" includes one or more a hydrophilic polymer-derivatized lipids, or mixtures of a hydrophilic polymer-derivatized lipids; reference to "a hydrophilic polymer" includes one or more hydrophilic polymers, or mixtures of hydrophilic polymers; reference to "a drug" includes one or more drugs, and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The term "enzyme" as used herein refers to any partially or wholly proteinaceous molecule that carries out a chemical reaction in a catalytic manner. Such enzymes can be native enzymes, fusion enzymes, proenzymes, apoenzymes, denatured enzymes, farnesylated enzymes, ubiquitinated enzymes, fatty acylated enzymes, gerangeranylated enzymes, GPI-linked enzymes, lipid-linked enzymes, prenylated enzymes, naturally-occurring or artificially generated mutant enzymes, enzymes with side chain or backbone modifications, enzymes having leader sequences, and enzymes complexed with non-proteinaceous material, such as proteoglycans and proteoliposomes. Enzymes can be made by any means, including natural expression, promoted expression, cloning, various solution-based and solid-based peptide syntheses, and similar methods known to those skilled in the art.

The term "$C_{x\text{-}y}$ alkyl" as used herein refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2\text{-}y}$ alkenyl" and "$C_{2\text{-}y}$ alkynyl" refer to substituted or unsubstituted unsaturated aliphatic groups analogous in length and possible substitution to the alkyls, but that contain at least one double or triple bond respectively.

The term "alkoxy" as used herein refers to an alkyl group having an oxygen attached thereto. Representative alkoxy groups include methoxy, ethoxy, propoxy, tert-butoxy, and the like.

The term "ether" as used herein refers to two hydrocarbons covalently linked by an oxygen. Accordingly, the substituent of an alkyl that renders that alkyl an ether is or resembles an alkoxy.

The term "$C_{1\text{-}6}$ alkoxyalkyl" as used herein refers to a $C_{1\text{-}6}$ alkyl group substituted with an alkoxy group, thereby forming an ether.

The term "$C_{1\text{-}6}$ aralkyl" as used herein refers to a $C_{1\text{-}6}$ alkyl group substituted with an aryl group.

The terms "amine" and "amino" as used herein are art-recognized and refer to both unsubstituted and substituted amines and salts thereof, e.g., a moiety that can be represented by the general formulae:

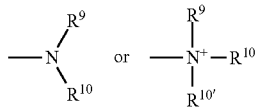

wherein $R^9$, $R^{10}$ and $R^{10'}$ each independently represent a hydrogen, an alkyl, an alkenyl, —$(CH_2)_m$—$R^8$, or $R^9$ and $R^{10}$ taken together with the N atom to which they are attached complete a heterocycle having from 4 to 8 atoms in the ring structure; $R^8$ represents an aryl, a cycloalkyl, a cycloalkenyl, a heterocyclyl or a polycyclyl; and m is zero or an integer from 1 to 8. In preferred embodiments, only one of $R^9$ or $R^{10}$ can be a carbonyl, e.g., $R^9$, $R^{10}$, and the nitrogen together do not form an imide. In even more preferred embodiments, $R^9$ and $R^{10}$ (and optionally $R^{10'}$) each independently represent a hydrogen, an alkyl, an alkenyl, or —$(CH_2)_m$—$R^8$. In certain embodiments, the amino group is basic, meaning the protonated form has a $pK_a \geq 7.00$.

The terms "amide" and "amido" are art-recognized as referring to an amino-substituted carbonyl and including a moiety that can be represented by the general formula:

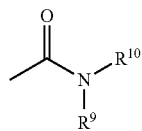

wherein $R^9$, $R^{10}$ are as defined above. Preferred embodiments of the amide does not include imides that can be unstable.

The term "aryl" as used herein refers to 5-membered, 6-membered, and 7-membered substituted or unsubstituted single-ring aromatic groups in which each atom of the ring is carbon. The term "aryl" also includes polycyclic ring systems having two or more cyclic rings in which two or more carbons are common to two adjoining rings, wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "carbocycle" and "carbocyclyl" as used herein refer to a non-aromatic substituted or unsubstituted ring in which each atom of the ring is carbon. The terms "carbocycle" and "carbocyclyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls.

The term "carbonyl" as used herein is art-recognized and refers to moieties as can be represented by the general formula:

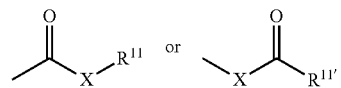

wherein X is a bond or represents an oxygen or a sulfur, and $R^{11}$ represents a hydrogen, an alkyl, an alkenyl, —$(CH_2)_m$—$R^8$, or a pharmaceutically acceptable salt; $R^{11'}$ represents a hydrogen, an alkyl, an alkenyl, or —$(CH_2)_m$—$R^8$, where m and $R^8$ are as defined below. Where X is an oxygen and $R^{11}$ or $R^{11'}$ is not hydrogen, the formula represents an "ester." Where X is an oxygen and $R^{11}$ is a hydrogen, the formula represents a "carboxylic acid."

The term "$C_{1\text{-}6}$ heteroaralkyl" as used herein refers to a $C_{1\text{-}6}$ alkyl group substituted with a heteroaryl group.

The term "heteroaryl" as used herein refers to substituted or unsubstituted aromatic 5-membered to 7-membered ring structures, more preferably 5-membered to 6-membered rings, whose ring structures include one to four heteroatoms. The term "heteroaryl" also includes polycyclic ring systems having two or more cyclic rings in which two or more carbons are common to two adjoining rings, wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, triazole, pyrazole, pyridine, pyrazine, pyridazine, pyrimidine, and the like.

The term "heteroatom" as used herein refers to an atom of any element other than carbon or hydrogen. Preferred heteroatoms are nitrogen, oxygen, phosphorus, and sulfur.

The terms "heterocyclyl" and "heterocyclic group" as used herein refer to substituted or unsubstituted non-aromatic 3-membered to 10-membered ring structures, more preferably 3-membered to 7-membered rings, whose ring structures include one to four heteroatoms. The term terms "heterocyclyl" or "heterocyclic group" also include polycyclic ring systems having two or more cyclic rings in which two or more carbons are common to two adjoining rings, wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "$C_{1-6}$hydroxyalkyl" as used herein refers to a $C_{1-6}$alkyl group substituted with a hydroxy group.

The term "thioether" as used herein refers to an alkyl group having a sulfur moiety attached thereto. In preferred embodiments, the "thioether" is represented by —S— alkyl. Representative thioether groups include methylthio, ethylthio, and the like.

The term "substituted" as used herein refers to moieties having substituents replacing a hydrogen on one or more carbons of the backbone. The terms "substitution" or "substituted with" include the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein that satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "inhibitor" as used herein refers to a compound that blocks or reduces an activity of an enzyme (e.g., inhibition of proteolytic cleavage of standard fluorogenic peptide substrates such as suc-LLVY-AMC, Boc-LLR-AMC and Z-LLE-AMC, inhibition of various catalytic activities of the 20S proteasome). An inhibitor can act with competitive, uncompetitive, or noncompetitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme.

The term "peptide" as used herein refers not only to standard amide linkage with standard α-substituents, but also to commonly used peptidomimetics, other modified linkages, non-naturally occurring side chains, and side chain modifications, for example, as described in U.S. Pat. No. 7,417,042.

The terms "polycyclyl" and "polycyclic" as used herein refer to two or more rings (e.g., cycloalkyls, cycloalkenyls, cycloalkynyls, aryls, heteroaryls, and/or heterocyclyls) in which two or more carbons are common to two adjoining rings, e.g., the rings are "fused rings." Each of the rings of the polycycle can be substituted or unsubstituted.

The term "prodrug" as used herein refers to compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The term "preventing" as used herein is art-recognized, and when used in relation to a condition, such as a local recurrence (e.g., pain), a disease such as cancer, a syndrome complex such as heart failure or any other medical condition, is well understood in the art, and includes administration of a composition that reduces the frequency of, or delays the onset of, symptoms of a medical condition in a subject relative to a subject who does not receive the composition. Thus, prevention of cancer includes, for example, reducing the number of detectable cancerous growths in a population of subjects receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "cancer," as used herein, includes, but is not limited to, blood borne and solid tumors.

The terms "autoimmune disease" and "autoimmune disorder," as used herein refer to a disease or disorder arising from and directed against an individual's own tissues.

The term "graft" as used herein refers to biological material derived from a donor for transplantation into a recipient.

The term "prophylactic or therapeutic" treatment, as used herein, is art-recognized and refers to administration to the subject of one or more of the subject compositions. If it is administered prior to clinical manifestation of the unwanted condition (e.g., disease or other unwanted state of the subject) then the treatment is prophylactic, (i.e., it protects the subject against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "proteasome" as used herein refers to immuno- and constitutive proteasomes.

The term "therapeutically effective amount" as used herein refers to an amount of the compound(s) (e.g., a peptide epoxyketone compound) in a preparation that, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The terms "treating" and "treatment" as used herein refer to reversing, reducing, or arresting the symptoms, clinical signs, and underlying pathology of a condition in manner to improve or stabilize a subject's condition.

The term "amphipathic lipids" as used herein refers to molecules that are mostly lipid-like (hydrophobic) in structure, but at one end have a region that is polar, charged, or a combination of polar and charged (hydrophilic). The hydrophilic region is referred to as the head group, and the lipid portion is known as the tail group(s). Examples of amphipathic lipids include phospholipids, glycolipids, and sphingolipids.

The terms "hydrophilic polymer" and "water-soluble polymer" as used herein refer to polymers, for example, polyethylene glycol (PEG) or other polyethoxylated polymers, used to shield liposomes and thereby enhance liposomal circulatory half-life. "Hydrophilic polymer" encompasses free hydrophilic polymers associated non-covalently with the liposomes and hydrophilic polymers that are conjugated or covalently linked to a component of the liposome (e.g., PEG-derivatized lipids). Additional exemplary hydrophilic polymers include, but are not limited to, polyvinyl alcohol, polylactic acid, polyglycolic acid, polyacrylamide, polyglycerol, poly(oxazoline), poly(N-(2-hydroxypropyl) methacrylamide)), poly-N-vinylpyrrolidone, and poly (amino acid)s (PAA) (including, for example, poly(hydroxy-ethyl 1-glutamine)-N-succinyldioctadecylamine (PHEG-DODASuc) and poly(hydroxyl-ethyl 1-asparagine)-DODASuc (PHEA-DODASuc)).

The term "free sterol" as used herein refers to a sterol that is not covalently bound to another compound. "Free cholesterol" refers to cholesterol that is not covalently bound as a moiety in a sterol-modified amphiphilic lipid compound.

The terms "sterol" and "steroid alcohols" as used herein refer to the subgroup of steroids having a free hydroxyl or a derivative thereof. Exemplary sterols include, but are not limited to, the class cholesterol and derivatives thereof, the class phytosterols and derivatives thereof, and the class fungal sterols and derivatives thereof. Sterols can be natural or synthetic.

The term "sterol-modified amphiphilic lipid" as used herein refers to amphiphilic lipid compounds having a hydrophilic head group, and two or more hydrophobic tails of which at least one is sterol. "Sterol-modified amphiphilic phospholipids" refers to a sterol-modified amphiphilic lipid comprising a phosphate-containing moiety, such as phosphocholine or phosphoglycerol.

The term "therapeutic agent" as used herein refers to an agent used in testing, development, or application as a therapeutic, including drugs and pharmaceutical agents.

The term "drug" as used herein refers to any chemical compound (e.g., a peptide epoxyketone compound) used in the diagnosis, treatment, or prevention of disease or other abnormal condition.

The term "prodrug" as used herein refers to compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the subject.

The terms "therapeutically acceptable" and "pharmaceutically acceptable" as used herein refer to a material that is not biologically or otherwise undesirable, i.e., the material can be administered to a subject together with an active ingredient without causing undesirable biological effects or interacting adversely with any other component of the composition.

The term "emulsion" as used herein refers to a mixture of two immiscible (unblendable) substances.

The term "bilayer" as used herein refers to a structure composed of amphiphilic lipid molecules (often phospho-lipids) arranged in two molecular layers, with the hydrophobic tails on the interior and the polar head groups on the exterior surfaces.

The term "monolayer" as used herein refers to a single molecular layer of amphipathic molecules with the head groups aligned on one side, and hydrophobic groups on the opposite side.

The term "liposome" as used herein refers to a vesicle comprising a lipid bilayer, for example, a closed vesicle formed when amphipathic lipids (e.g., phospholipids or their derivatives) are dispersed in water. The liposomes of the present invention typically comprise one or more phospholipids, and may also contain mixed lipid chains with surfactant properties (e.g., egg phosphatidylethanolamine). Liposome can employ surface ligands to target binding to unhealthy tissue (e.g., tumors or neoplastic cells). Liposomes typically have an aqueous core.

The term "entrapped" as used herein refers to the non-covalent association of peptide epoxyketone compounds with a liposome bilayer and/or the liposome's interior aqueous volume (also called the liposome's aqueous core).

The terms "liposomal composition" and "liposome-containing composition" are used interchangeably herein and refer to liposome formulations or mixtures comprising lipids (e.g., phospholipids, hydrophilic polymer-derivatized lipids, sterol components such as cholesterols, and combinations thereof) and peptide epoxyketone compounds, and such liposome mixtures or formulations can further comprise additional excipients. A liposomal composition typically comprises an aqueous solution comprising the liposomes. Encapsulated aqueous solution is aqueous solution in the aqueous core of the liposomes. Non-encapsulated aqueous solution is aqueous solution in which the liposomes are dispersed.

The term "excipient" as used herein typically refers to any pharmacologically inactive substance used for in the formulation or administration of the liposomal compositions of the present invention, for example, phospholipid, buffer, a carrier or vehicle (such as diluents), and so on. Examples of excipients useful in the practice of the present invention are described herein.

The term "pH adjusting agent" as used herein refers to any agent used to modify the pH of an aqueous solution. pH is adjusted by using acidifying (e.g., acids) and alkalizing agents (e.g., salts of acids or bases). Acidifying agents are used in a formulation to lower the pH and alkalizing agents are used to increase the pH. pH adjusting agents include buffering systems (e.g., combinations of acids and bases). Pharmaceutical compositions of the present invention can contain one or more of these agents to achieve a desirable pH either for preparation (i.e., in bulk solution) of the composition or upon reconstitution for therapeutic administration.

The term "solublizing agent" as used herein refers to an agent, typically a compound, pH adjusting agent, or cosolvent, that increases the solubility of a peptide epoxyketone compound in an aqueous solution.

The term "physiological conditions" as used herein refers to conditions compatible with living cells, e.g., predominantly aqueous conditions of a temperature, pH, salinity, etc.

The terms "therapeutic composition," "pharmaceutical composition," "therapeutic preparation," and "pharmaceutical preparation" are used interchangeably herein and encompass liposomal compositions of the present invention suitable for application or administration to a subject, typically a human. In general such compositions are safe, sterile or aseptic, and preferably free of contaminants that are capable of eliciting undesirable responses in the subject (i.e., the compound(s) comprising the composition are pharmaceutically acceptable). Compositions can be formulated for application or administration to a subject in need thereof by a number of different routes of administration including oral (i.e., administered by mouth or alimentary canal) or parenteral (e.g., buccal, rectal, transdermal, transmucosal, subcutaneous, intravenous, intraperitoneal, intradermal, intratracheal, intrathecal, pulmonary, and the like).

The term "aseptic conditions" as used herein typically refers to manufacturing or processing conditions wherein the manufactured product is free from contamination with pathogens.

The term "subject" as used herein refers to any member of the subphylum chordata, including, without limitation, humans and other primates, including non-human primates such as rhesus macaque, chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese; and the like. The term does not denote a particular age. Thus, adult, young, and newborn individuals are intended to be covered.

2.0.0 General Overview of the Invention

Before describing the present invention in detail, it is to be understood that this invention is not limited to particular types of liposomes, particular sources of drugs, particular lipids, particular polymers, and the like, as use of such particulars can be selected in view of the teachings of the present specification. It is also to be understood that the terminology used herein is for the purpose of describing particular embodiments of the invention only, and is not intended to be limiting.

Peptide epoxyketone compounds (e.g., carfilzomib) are proteasome inhibitors useful for the treatment of a wide variety of diseases and conditions. At present, carfilzomib for injection is prepared by dissolving carfilzomib drug substance in sulfobutylether beta cyclodextrin (SBE-B-CD) with citric acid using a slurry method to create a bulk solution that is then lyophilized to yield a lyophilized carfilzomib suitable for reconstitution and injection.

However, intravenous administration of the carfilzomib SBE-B-CD composition results in a short half-life due to rapid metabolism. Clearance of carfilzomib is largely extra-hepatic, and carfilzomib is predominantly eliminated by peptidase cleavage and epoxide hydrolysis. Therefore, multiple weekly injections are used for treatment regimens. In addition, the use of the SBE-B-CD composition can limit dose increases of carfilzomib, which can impact its best profile activities.

Liposomes are spherical vesicles, typically comprising phospholipids, that have an internal aqueous volume that is enclosed by one or more concentric lipid bilayers with the polar head groups oriented towards the interior and exterior aqueous phases. Natural phospholipids are biocompatible and biodegradable as they are naturally occurring in the body and are a major constituent of cell membranes. Liposomes can act as drug carriers by entrapping drugs in the aqueous core and/or within the lipid bilayers. Liposomes range in size and can exist as unilamellar or multilamellar vesicles.

The present application describes the successful development of a variety of pharmaceutical liposomal compositions incorporating peptide epoxyketone proteasome inhibitors. In some aspects of the present invention, entrapment of peptide epoxyketone compounds are described. In other aspects of the present invention, incorporation of peptide epoxyketone compounds into the interior aqueous core of liposomes are described. The liposomal compositions comprising peptide epoxyketone compounds described herein enhance the therapeutic window of peptide epoxyketone compounds by: improving in vivo half-life (e.g., plasma half-life) relative to non-liposomal compositions comprising peptide epoxyketone compounds; providing desirable pharmacodynamic profiles (e.g., biodistribution, proteasome chymotrypsin-like (CT-L) activity inhibition, and prolonged inhibition of proteasome CT-L activity in selected tissues); and providing anti-tumor activity in a human tumor xenograft model, greater than or equal to non-liposomal compositions comprising peptide epoxyketone compounds. Further, experiments performed in support of the present invention demonstrated improved tolerability of liposomal compositions comprising peptide epoxyketone compounds (e.g., improving maximum tolerated dose relative to non-liposomal compositions comprising peptide epoxyketone compounds).

The pharmaceutical liposomal compositions of the present invention are typically prepared to be sterile or aseptic compositions, and methods of making the pharmaceutical liposomal compositions suitable for administration to a subject are typically carried out under sterile or aseptic conditions. Terminal sterilization of the pharmaceutical liposomal compositions of the present invention can also be employed.

In a first aspect, the present invention relates to pharmaceutical liposomal compositions. In some embodiments, the pharmaceutical liposomal compositions comprise liposome entrapped peptide epoxyketone compound. Such pharmaceutical compositions typically comprise an aqueous solution comprising liposomes, wherein the liposomes comprise between about 0.5 wt. % and about 50 wt. % of a peptide epoxyketone compound, and between about 99.5 wt. % and about 50 wt. % total lipids (weight ratio of peptide epoxyketone compound:total lipids of between about 0.005:0.995 and about 0.5:0.5). In preferred embodiments the total lipids comprise a phospholipid selected from the group consisting of L-α-phosphatidylcholine; 1,2-distearoyl-sn-glycero-3-phosphocholine; 1,2-dipalmitoyl-sn-glycero-3-phosphocholine; 1,2-Distearoyl-sn-glycero-3-phospho-rac-(1-glycerol); 1-Palmitoyl-2-oleoyl-sn-glycero-3-phosphocholine; sphingomyelin; 1,2-distearoyl-sn-glycero-3-phosphoethanolamine; as well as combinations thereof.

In embodiments of the pharmaceutical liposomal compositions of the present invention, the weight ratio of peptide epoxyketone compound:total lipid is between about 0.005:0.995 and about 0.35:0.65 (in weight percent, between about 0.5 wt. % and about 35 wt. % peptide epoxyketone compound and between about 99.5 wt. % and about 65 wt. % total lipids), preferably between about 0.01:0.99 and about 0.30:0.70 (in weight percent, between about 1 wt. % and about 30 wt. % peptide epoxyketone compound and between about 99 wt. % and about 70 wt. % total lipids), and more preferably between about 0.01:0.99 and about 0.25:0.75 (in weight percent, between about 1 wt. % and about 25 wt. % peptide epoxyketone compound and between about 99 wt. % and about 75 wt. % total lipids).

In some embodiments of the pharmaceutical liposomal compositions of the present invention, the total lipids of the liposomes comprise between about 20 wt. % to about 100 wt. % phospholipid. In preferred embodiments of the pharmaceutical liposomal compositions of the present invention, the weight percents of phospholipid include, but are not limited to, the following: wherein the total lipids of the liposomes comprise between about 30 wt. % and about 90 wt. % phospholipid, preferably between about 50 wt. % and about 75 wt. % phospholipid.

In further embodiments, the total lipids of the liposomes comprise a hydrophilic polymer-derivatized lipid, for example, wherein the total lipids comprise between about 0.1 wt. % and about 30 wt. % of a hydrophilic polymer-derivatized lipid, between about 5 wt. % and about 25 wt. % of a hydrophilic polymer-derivatized lipid, and preferably between about 8 wt. % and about 20 wt. % of a hydrophilic polymer-derivatized lipid. Exemplary embodiments include, but are not limited to, liposomes of the pharmaceutical liposomal composition comprising between about 90 wt. % of the phospholipid and about 75 wt. % of the phospholipid, and between about 10 wt. % of the hydrophilic polymer-derivatized lipid and about 25 wt. % of the hydrophilic polymer-derivatized lipid (total lipid weight ratio of phospholipid:hydrophilic polymer-derivatized lipid: {cholesterol or cholesterol derivative} of between about 0.9:0.1:0 and about 0.75:0.25:0). In embodiments wherein the total lipids comprise a hydrophilic polymer-derivatized lipid, the lipid of the hydrophilic polymer-derivatized lipid is, for example, cholesterol or a phospholipid. In some embodiments, the hydrophilic polymer of a hydrophilic polymer-derivatized lipid is a polyethylene glycol. In a preferred embodiment, the hydrophilic polymer-derivatized lipid is 1,2-distearoyl-sn-glycero-3-phosphoethanolamine-N-[methoxy(polyethylene glycol)-2000] (mPEG2000DSPE).

In further embodiments, the total lipids of the liposomes comprise a cholesterol or cholesterol derivative, wherein the total lipids comprise between about 10 wt. % and about 50 wt. % a cholesterol or cholesterol derivative, between about 15 wt. % and about 40 wt. % a cholesterol or cholesterol derivative, preferably between about 15 wt. % and about 30 wt. % a cholesterol or cholesterol derivative. Exemplary embodiments include, but are not limited to, liposomes of the pharmaceutical liposomal composition comprising between about 90 wt. % and about 50 wt. % of the phospholipid, and between about 10 wt. % and about 50 wt. % of a cholesterol or derivative (total lipid weight ratio of phospholipid:hydrophilic polymer-derivatized lipid: {cholesterol or cholesterol derivative} of between about 0.9:0:0.1 and about 0.5:0:0.5). In preferred embodiments wherein the total lipids comprise a cholesterol or cholesterol derivative, the cholesterol or cholesterol derivative is cholesterol.

In additional embodiments, the total lipids of the liposomes comprise a phospholipid, a hydrophilic polymer-derivatized lipid, and a cholesterol or cholesterol derivative. Exemplary embodiments include, but are not limited to, liposomes of the pharmaceutical liposomal composition that comprise total lipids of between about 83.3 wt. % of the phospholipid and about 57 wt. % of the phospholipid, between about 8.33 wt. % of the hydrophilic polymer-derivatized lipid and about 14 wt. % of the hydrophilic polymer-derivatized lipid, and between about 8.33 wt. % of the cholesterol or cholesterol derivative and about 29 wt. % of the cholesterol or cholesterol derivative (total lipid weight ratio of phospholipid:hydrophilic polymer-derivatized lipid: {cholesterol or cholesterol derivative} of between about 0.833:0.0833:0.0833 and about 0.57:0.14:0.29).

The liposomes of the liposomal compositions of the present invention typically have an average size of between about 0.05 microns and about 0.5 microns, between about 0.05 microns and about 0.2 microns, between about 0.05 microns and about 0.15 microns, and preferably between about 0.05 microns and about 0.10 microns.

The lipids of the liposomes, in some embodiments, further comprise α-tocopherol, for example, at about 0.001 to about 5 weight percent.

The aqueous solution in which the liposomes are dispersed can also comprise one or more excipients, including, but not limited to, a pH adjusting agent (e.g., a buffer) and/or an agent to maintain isotonicity.

In other embodiments of this first aspect of the present invention, the liposomal compositions comprise liposomes comprising the peptide epoxyketone compound and a solubilizing agent in an internal aqueous core of the liposomes. In some embodiments, the solubilizing agent is a compound (e.g., a cyclodextrin), and the liposomes of the liposomal composition comprise the peptide epoxyketone compound complexed with the compound (e.g., a cyclodextrin) in the internal aqueous core of the liposomes. A preferred solubilizing agent that is a compound is a cyclodextrin, for example, a sulfobutylether-betacyclodextrin or a hydroxypropyl-betacyclodextrin.

The pharmaceutical liposomal composition of the present invention can also include liposomal compositions wherein the aqueous solution is adjusted to a pH of between about pH 3.0 and about pH 7.0. Preferably, the aqueous solution is adjusted to a human physiological pH.

Examples of peptide epoxyketone compounds for use in liposomal compositions of the present invention include, but are not limited to, compound I. Preferred peptide epoxyketone compounds for use in liposomal compositions include compound II, compound III, compound IV, and, most preferably carfilzomib (compound V).

Preferred embodiments of pharmaceutical liposomal compositions comprising peptide epoxyketone compounds include, but are not limited to, the following: peptide epoxyketone compound-EPC-mPEG2000DSPE-cholesterol; peptide epoxyketone compound-sphingomyelin-mPEG2000DSPE-cholesterol; and peptide epoxyketone compound-HSPC-mPEG2000DSPE-cholesterol.

In a second aspect, the present invention relates to dry pharmaceutical compositions formed by drying the pharmaceutical liposomal compositions described herein.

In a third aspect, the present invention relates to dry pharmaceutical compositions comprising peptide epoxyketone compounds. One embodiment of this third aspect of the present invention is a dry pharmaceutical composition comprising between about 0.5 wt. % and about 50 wt. % of a peptide epoxyketone compound, and between about 99.5 wt. % and about 50 wt. % total lipids (weight ratio of peptide epoxyketone compound:total lipids of between about 0.005:0.995 and about 0.5:0.5). In preferred embodiments, the total lipids comprise a phospholipid selected from the group consisting of L-α-phosphatidylcholine; 1,2-distearoyl-sn-glycero-3-phosphocholine; 1,2-dipalmitoyl-sn-glycero-3-phosphocholine; 1,2-Distearoyl-sn-glycero-3-phospho-rac-(1-glycerol); 1-Palmitoyl-2-oleoyl-sn-glycero-3-phosphocholine; sphingomyelin; 1,2-distearoyl-sn-glycero-3-phosphoethanolamine; and combinations thereof.

In embodiments of the dry pharmaceutical compositions of the present invention, the weight ratio of peptide epoxyketone compound:total lipid is between about 0.005:0.995 and about 0.35:0.65 (in weight percent, between about 0.5 wt. % and about 35 wt. % peptide epoxyketone compound and between about 99.5 wt. % and about 65 wt. % total lipids), preferably between about 0.01:0.99 and about 0.30:0.70 (in weight percent, between about 1 wt. % and about 30 wt. % peptide epoxyketone compound and between about 99 wt. % and about 70 wt. % total lipids), and more preferably between about 0.01:0.99 and about 0.25:0.75 (in weight percent, between about 1 wt. % and about 25 wt. % peptide epoxyketone compound and between about 99 wt. % and about 75 wt. % total lipids).

In some embodiments of the dry pharmaceutical compositions of the present invention, the total lipids comprise between about 20 wt. % to about 100 wt. % phospholipid. In preferred embodiments of the dry pharmaceutical compositions of the present invention, the weight percents of phospholipid include, but are not limited to, the following: wherein the total lipids comprise between about 30 wt. % and about 90 wt. % phospholipid, preferably between about 50 wt. % and about 75 wt. % phospholipid.

In further embodiments, the total lipids of the dry pharmaceutical compositions comprise a hydrophilic polymer-derivatized lipid, for example, wherein the total lipids comprise between about 0.1 wt. % and about 30 wt. % of a hydrophilic polymer-derivatized lipid, between about 5 wt. % and about 25 wt. % of a hydrophilic polymer-derivatized lipid, and preferably between about 8 wt. % and about 20 wt. % of a hydrophilic polymer-derivatized lipid. Exemplary embodiments include, but are not limited to, dry pharmaceutical compositions comprising between about 90 wt. % of the phospholipid and about 75 wt. % of the phospholipid, and between about 10 wt. % of the hydrophilic polymer-derivatized lipid and about 25 wt. % of the hydrophilic polymer-derivatized lipid (total lipid weight ratio of phospholipid:hydrophilic polymer-derivatized lipid: {cholesterol or cholesterol derivative} of between about 0.9:0.1:0 and about 0.75:0.25:0). In embodiments wherein the total lipids comprise a hydrophilic polymer-derivatized lipid, the lipid of the hydrophilic polymer-derivatized lipid is, for example, cholesterol or a phospholipid. In some embodiments, the hydrophilic polymer of a hydrophilic polymer-derivatized lipid is a polyethylene glycol. In a preferred embodiment, the hydrophilic polymer-derivatized lipid is 1,2-distearoyl-sn-glycero-3-phosphoethanolamine-N-[methoxy(polyethylene glycol)-2000] (mPEG2000DSPE).

In further embodiments, the total lipids of the dry pharmaceutical compositions comprise a cholesterol or cholesterol derivative, wherein the total lipids comprise between about 10 wt. % and about 50 wt. % a cholesterol or cholesterol derivative, between about 15 wt. % and about 40 wt. % a cholesterol or cholesterol derivative, preferably between about 15 wt. % and about 30 wt. % a cholesterol or cholesterol derivative. Exemplary embodiments include, but are not limited to, dry pharmaceutical compositions comprising between about 90 wt. % and about 50 wt. % of the phospholipid, and between about 10 wt. % and about 50 wt. % of a cholesterol or derivative (total lipid weight ratio of phospholipid:hydrophilic polymer-derivatized lipid: {cholesterol or cholesterol derivative} of between about 0.9:0:0.1 and about 0.5:0:0.5). In preferred embodiments wherein the total lipids comprise a cholesterol or cholesterol derivative, the cholesterol or cholesterol derivative is cholesterol.

In additional embodiments, the total lipids of the dry pharmaceutical compositions comprise a phospholipid, a hydrophilic polymer-derivatized lipid, and a cholesterol or cholesterol derivative. Exemplary embodiments include, but are not limited to, dry pharmaceutical compositions that comprise total lipids of between about 83.3 wt. % of the phospholipid and about 57 wt. % of the phospholipid, between about 8.33 wt. % of the hydrophilic polymer-derivatized lipid and about 14 wt. % of the hydrophilic polymer-derivatized lipid, and between about 8.33 wt. % of the cholesterol or cholesterol derivative and about 29 wt. % of the cholesterol or cholesterol derivative (total lipid weight ratio of phospholipid:hydrophilic polymer-derivatized lipid: {cholesterol or cholesterol derivative} of between about 0.833:0.0833:0.0833 and about 0.57:0.14:0.29).

The dry pharmaceutical compositions, in some embodiments, further comprise α-tocopherol, for example, at about 0.001 to about 5 weight percent.

The dry pharmaceutical compositions comprising peptide epoxyketone compounds can also comprise one or more excipients, including, but not limited to, a pH adjusting agent (e.g., a buffer) and/or an agent to maintain isotonicity.

In other embodiments of this third aspect of the present invention, the dry pharmaceutical compositions comprise the peptide epoxyketone compound and a cyclodextrin. Preferred cyclodextrins include sulfobutylether-betacyclodextrins or hydroxypropyl-betacyclodextrins.

Examples of peptide epoxyketone compounds for use in dry pharmaceutical compositions of the present invention include, but are not limited to, compound I. Preferred peptide epoxyketone compounds for use in dry pharmaceutical compositions include compound II, compound III, compound IV, and, most preferably carfilzomib (compound V).

In some embodiments, dry pharmaceutical compositions further comprise additional excipients, for example cryoprotectant agents (e.g., glycerol, dimethylamine, dimethylsulfoxide), glass transition modifying agents (e.g. sugars, polyols, polymers, amino acids), combinations thereof, and/or other stabilizing excipients.

Preferred embodiments of dry pharmaceutical compositions comprising peptide epoxyketone compounds include, but are not limited to, the following: peptide epoxyketone compound-EPC-mPEG2000DSPE-cholesterol; peptide epoxyketone compound-sphingomyelin-mPEG2000DSPE-cholesterol; and peptide epoxyketone compound-HSPC-mPEG2000DSPE-cholesterol.

In a fourth aspect, the present invention relates to a method of making pharmaceutical liposomal compositions comprising reconstituting dry pharmaceutical compositions comprising peptide epoxyketone compounds and lipids (for example, as described in the third aspect of the present invention) using an aqueous solution to form liposomes, the pharmaceutical liposomal composition comprising the aqueous solution comprising the liposomes.

In a fifth aspect, the present invention relates to pharmaceutical liposomal compositions made by the method described in the fourth aspect of the present invention. The liposomes of the pharmaceutical liposomal compositions have, for example, liposomes with an average size of between about 0.05 microns and about 0.5 microns, between about 0.05 microns and about 0.2 microns, between about 0.05 microns and about 0.15 microns, and preferably between about 0.05 microns and about 0.10 microns.

In a sixth aspect, the present invention relates to a method of making a pharmaceutical liposomal composition comprising preparing a dried film comprising total lipids, and rehydrating the dried film with an aqueous solution comprising a peptide epoxyketone compound and a solubilizing agent to form the pharmaceutical liposomal composition. Typically the method comprises preparing a dried film comprising total lipids, wherein the total lipids comprise a phospholipid selected from the group consisting of L-α-phosphatidylcholine; 1,2-distearoyl-sn-glycero-3-phosphocholine; 1,2-dipalmitoyl-sn-glycero-3-phosphocholine; 1,2-Distearoyl-sn-glycero-3-phospho-rac-(1-glycerol); 1-Palmitoyl-2-oleoyl-sn-glycero-3-phosphocholine; sphingomyelin; 1,2-distearoyl-sn-glycero-3-phosphoethanolamine; and a combination thereof. The dried film is rehydrated with an aqueous solution comprising a peptide epoxyketone compound and a solubilizing agent to form the pharmaceutical liposomal composition comprising liposomes dispersed in the aqueous solution; wherein the liposomes comprise (i) between about 0.5 wt. % and about 50 wt. % of the peptide epoxyketone compound entrapped in the liposomes, and (ii) between about 99.5 wt. % and about 50 wt. % of the total lipids (i.e., weight ratio of peptide epoxyketone compound:total lipids of between about 0.005:0.995 and about 0.5:0.5).

In embodiments of the methods of this sixth aspect of the present invention, the weight ratio of peptide epoxyketone compound:total lipid is between about 0.005:0.995 and about 0.35:0.65 (in weight percent, between about 0.5 wt. % and about 35 wt. % peptide epoxyketone compound and between about 99.5 wt. % and about 65 wt. % total lipids), preferably between about 0.01:0.99 and about 0.30:0.70 (in weight percent, between about 1 wt. % and about 30 wt. % peptide epoxyketone compound and between about 99 wt. % and about 70 wt. % total lipids), and more preferably between about 0.01:0.99 and about 0.25:0.75 (in weight percent, between about 1 wt. % and about 25 wt. % peptide epoxyketone compound and between about 99 wt. % and about 75 wt. % total lipids).

In some embodiments of the methods of this sixth aspect of the present invention, the total lipids comprise between about 20 wt. % to about 100 wt. % phospholipid. In preferred embodiments of the method, the weight percents of phospholipid include, but are not limited to, the following: wherein the total lipids comprise between about 30 wt. % and about 90 wt. % phospholipid, preferably between about 50 wt. % and about 75 wt. % phospholipid.

In further embodiments of the method, the total lipids comprise a hydrophilic polymer-derivatized lipid, for example, wherein the total lipids comprise between about 0.1 wt. % and about 30 wt. % of a hydrophilic polymer-derivatized lipid, between about 5 wt. % and about 25 wt. % of a hydrophilic polymer-derivatized lipid, and preferably between about 8 wt. % and about 20 wt. % of a hydrophilic polymer-derivatized lipid. Exemplary embodiments include, but are not limited to, wherein the total lipids comprise between about 90 wt. % of the phospholipid and about 75 wt. % of the phospholipid, and between about 10 wt. % of the hydrophilic polymer-derivatized lipid and about 25 wt. % of the hydrophilic polymer-derivatized lipid (total lipid weight ratio of phospholipid:hydrophilic polymer-derivatized lipid: {cholesterol or cholesterol derivative} of between about 0.9:0.1:0 and about 0.75:0.25:0). In embodiments wherein the total lipids comprise a hydrophilic polymer-derivatized lipid, the lipid of the hydrophilic polymer-derivatized lipid is, for example, cholesterol or a phospholipid. In some embodiments, the hydrophilic polymer of a hydrophilic polymer-derivatized lipid is a polyethylene glycol. In a preferred embodiment, the hydrophilic polymer-derivatized lipid is 1,2-distearoyl-sn-glycero-3-phosphoethanolamine-N-[methoxy(polyethylene glycol)-2000] (mPEG2000DSPE).

In further embodiments of the methods of this sixth aspect of the present invention, the total lipids comprise a cholesterol or cholesterol derivative, wherein the total lipids comprise between about 10 wt. % and about 50 wt. % a cholesterol or cholesterol derivative, between about 15 wt. % and about 40 wt. % a cholesterol or cholesterol derivative, preferably between about 15 wt. % and about 30 wt. % a cholesterol or cholesterol derivative. Exemplary embodiments include, but are not limited to, total lipids comprising between about 90 wt. % and about 50 wt. % of the phospholipid, and between about 10 wt. % and about 50 wt. % of a cholesterol or derivative (total lipid weight ratio of phospholipid:hydrophilic polymer-derivatized lipid: {cholesterol or cholesterol derivative} of between about 0.9:0:0.1 and about 0.5:0:0.5). In preferred embodiments wherein the total lipids comprise a cholesterol or cholesterol derivative, the cholesterol or cholesterol derivative is cholesterol.

In additional embodiments of the method, the total lipids comprise a phospholipid, a hydrophilic polymer-derivatized lipid, and a cholesterol or cholesterol derivative. Exemplary embodiments include, but are not limited to, total lipids of between about 83.3 wt. % of the phospholipid and about 57 wt. % of the phospholipid, between about 8.33 wt. % of the hydrophilic polymer-derivatized lipid and about 14 wt. % of the hydrophilic polymer-derivatized lipid, and between about 8.33 wt. % of the cholesterol or cholesterol derivative and about 29 wt. % of the cholesterol or cholesterol derivative (total lipid weight ratio of phospholipid:hydrophilic polymer-derivatized lipid: {cholesterol or cholesterol derivative} of between about 0.833:0.0833:0.0833 and about 0.57:0.14:0.29).

In some embodiments of the method of this sixth aspect of the present invention the solubilizing agent is, for example, a compound, a pH adjusting agent, a cosolvent, or a combination thereof. In some embodiments, the solubilizing agent is a compound (e.g., a cyclodextrin), and the liposomes of the liposomal composition comprise the peptide epoxyketone compound complexed with the compound (e.g., a cyclodextrin) in the internal aqueous core of the liposomes. A preferred solubilizing agent that is a compound is a cyclodextrin, for example, a sulfobutylether-betacyclodextrin or a hydroxypropyl-betacyclodextrin. In other embodiments, the solubilizing agent comprises a pH adjusting agent and the aqueous solution has a pH of between about pH 0.5 and about pH 3, between about pH 0.5 and about pH 2, and preferably between about pH 1 and about pH 2. In further embodiments, the solubilizing agent comprises a cosolvent.

The methods of this sixth aspect of the present invention can further include dialysis, desalting, buffer exchange, and/or gel filtration.

The method can further comprise sizing the liposomes to have an average size of between about 0.05 microns and about 0.5 microns, an average size of between about 0.05 microns and about 0.2 microns, between about 0.05 microns and about 0.15 microns, and preferably between about 0.05 microns and about 0.10 microns.

In some embodiments, the method further comprises, after forming the liposomal composition (wherein the liposomal composition comprises aqueous solution encapsulated in the liposomes and aqueous solution not encapsulated in the liposomes, i.e., non-encapsulated aqueous solution), removing peptide epoxyketone compound from the non-encapsulated aqueous solution in which the liposomes are dispersed. Removal of peptide expoxyketone compounds from the non-encapsulated aqueous solution can be accomplished, for example, using dialysis, ultracentrifugation, gel filtration, or combinations thereof.

In some embodiments, the method further comprise, after rehydrating the dried film to form the liposomal composition, adjusting the pH of the aqueous solution. The pH can be adjusted to, for example, a pH of between about pH 3.0 and about pH 7.0, preferably to a human physiological pH.

The method can further comprise, after rehydrating the dried film to form the liposomal composition, adding one or more excipients to the aqueous solution, for example, a pH adjusting agent (e.g., a buffer) and/or an agent to maintain isotonicity.

Examples of peptide epoxyketone compounds for use in the method include, but are not limited to, compound I. Preferred peptide epoxyketone compounds for use in liposomal compositions include compound II, compound III, compound IV, and, most preferably carfilzomib (compound V).

In a seventh aspect, the present invention relates to pharmaceutical liposomal compositions made by the method of the sixth aspect of the present invention; the liposomal composition comprising liposomes dispersed in the aqueous solution, wherein the liposomes comprise a peptide epoxyketone compound entrapped in the liposomes.

In an eight aspect, the present invention relates to a dry pharmaceutical composition formed by drying the pharmaceutical liposomal composition of the seventh aspect of the invention.

In a ninth aspect, the present invention relates to a method of making a pharmaceutical liposomal composition comprising preparing a lipid solution and injecting the lipid solution into an aqueous solution comprising a peptide epoxyketone compound. The lipid solution comprises a solvent and total lipids. The total lipids typically comprise a phospholipid, for example, L-α-phosphatidylcholine, 1,2-distearoyl-sn-glycero-3-phosphocholine, 1,2-dipalmitoyl-sn-glycero-3-phosphocholine, 1,2-Distearoyl-sn-glycero-3-phospho-rac-(1-glycerol), 1-Palmitoyl-2-oleoyl-sn-glycero-3-phosphocholine, sphingomyelin, 1,2-distearoyl-sn-glycero-3-phosphoethanolamine, and combinations thereof. Typically the method comprises injecting the lipid solution into an aqueous solution comprising a peptide epoxyketone compound and a solubilizing agent to form the pharmaceutical liposomal composition. The pharmaceutical liposomal composition comprises liposomes dispersed in the aqueous solution, wherein the liposomes comprise (i) between about 0.5 wt. % and about 50 wt. % of the peptide epoxyketone compound entrapped in the liposomes, and (ii) between about 99.5 wt. % and about 50 wt. % of the total lipids (weight ratio of peptide epoxyketone compound:total lipids of between about 0.005:0.995 and about 0.5:0.5).

In some embodiments the solvent is an organic solvent, for example an alcohol (e.g., ethanol).

In embodiments of the methods of this ninth aspect of the present invention, the weight ratio of peptide epoxyketone compound:total lipid is between about 0.005:0.995 and about 0.35:0.65 (in weight percent, between about 0.5 wt. % and about 35 wt. % peptide epoxyketone compound and between about 99.5 wt. % and about 65 wt. % total lipids), preferably between about 0.01:0.99 and about 0.30:0.70 (in weight percent, between about 1 wt. % and about 30 wt. % peptide epoxyketone compound and between about 99 wt. % and about 70 wt. % total lipids), and more preferably between about 0.01:0.99 and about 0.25:0.75 (in weight percent, between about 1 wt. % and about 25 wt. % peptide epoxyketone compound and between about 99 wt. % and about 75 wt. % total lipids).

In some embodiments of the methods of this ninth aspect of the present invention, the total lipids comprise between about 20 wt. % to about 100 wt. % phospholipid. In preferred embodiments of the method, the weight percents of phospholipid include, but are not limited to, the following: wherein the total lipids comprise between about 30 wt. % and about 90 wt. % phospholipid, preferably between about 50 wt. % and about 75 wt. % phospholipid.

In further embodiments of the method, the total lipids comprise a hydrophilic polymer-derivatized lipid, for example, wherein the total lipids comprise between about 0.1 wt. % and about 30 wt. % of a hydrophilic polymer-derivatized lipid, between about 5 wt. % and about 25 wt. % of a hydrophilic polymer-derivatized lipid, and preferably between about 8 wt. % and about 20 wt. % of a hydrophilic polymer-derivatized lipid. Exemplary embodiments include, but are not limited to, wherein the total lipids comprise between about 90 wt. % of the phospholipid and about 75 wt. % of the phospholipid, and between about 10 wt. % of the hydrophilic polymer-derivatized lipid and about 25 wt. % of the hydrophilic polymer-derivatized lipid (total lipid weight ratio of phospholipid:hydrophilic polymer-derivatized lipid: {cholesterol or cholesterol derivative} of between about 0.9:0.1:0 and about 0.75:0.25:0). In embodiments wherein the total lipids comprise a hydrophilic polymer-derivatized lipid, the lipid of the hydrophilic polymer-derivatized lipid is, for example, cholesterol or a phospholipid. In some embodiments, the hydrophilic polymer of a hydrophilic polymer-derivatized lipid is a polyethylene glycol. In a preferred embodiment, the hydrophilic polymer-derivatized lipid is 1,2-distearoyl-sn-glycero-3-phosphoethanolamine-N-[methoxy(polyethylene glycol)-2000] (mPEG2000DSPE).

In further embodiments of the methods of this ninth aspect of the present invention, the total lipids comprise a cholesterol or cholesterol derivative, wherein the total lipids comprise between about 10 wt. % and about 50 wt. % a cholesterol or cholesterol derivative, between about 15 wt. % and about 40 wt. % a cholesterol or cholesterol derivative, preferably between about 15 wt. % and about 30 wt. % a cholesterol or cholesterol derivative. Exemplary embodiments include, but are not limited to, total lipids comprising between about 90 wt. % and about 50 wt. % of the phospholipid, and between about 10 wt. % and about 50 wt. % of a cholesterol or derivative (total lipid weight ratio of phospholipid:hydrophilic polymer-derivatized lipid: {cholesterol or cholesterol derivative} of between about 0.9:0:0.1 and about 0.5:0:0.5). In preferred embodiments wherein the total lipids comprise a cholesterol or cholesterol derivative, the cholesterol or cholesterol derivative is cholesterol.

In additional embodiments of the method, the total lipids comprise a phospholipid, a hydrophilic polymer-derivatized lipid, and a cholesterol or cholesterol derivative. Exemplary embodiments include, but are not limited to, total lipids of between about 83.3 wt. % of the phospholipid and about 57 wt. % of the phospholipid, between about 8.33 wt. % of the hydrophilic polymer-derivatized lipid and about 14 wt. % of the hydrophilic polymer-derivatized lipid, and between about 8.33 wt. % of the cholesterol or cholesterol derivative and about 29 wt. % of the cholesterol or cholesterol derivative (total lipid weight ratio of phospholipid:hydrophilic polymer-derivatized lipid: {cholesterol or cholesterol derivative} of between about 0.833:0.0833:0.0833 and about 0.57:0.14:0.29).

In some embodiments of the method of this ninth aspect of the present invention the solubilizing agent is, for example, a compound, a pH adjusting agent, a cosolvent, or a combination thereof. In some embodiments, the solubilizing agent is a compound (e.g., a cyclodextrin), and the liposomes of the liposomal composition comprise the peptide epoxyketone compound complexed with the compound (e.g., a cyclodextrin) in the internal aqueous core of the liposomes. A preferred solubilizing agent that is a compound is a cyclodextrin, for example, a sulfobutylether-betacyclodextrin or a hydroxypropyl-betacyclodextrin. In other embodiments, the solubilizing agent comprises a pH adjusting agent and the aqueous solution has a pH of between about pH 0.5 and about pH 3, between about pH 0.5 and about pH 2, and preferably between about pH 1 and about pH 2. In further embodiments, the solubilizing agent comprises a cosolvent.

The method of this ninth aspect of the present invention can further include dialysis, desalting, buffer exchange, and/or gel filtration.

The method can further comprise sizing the liposomes to have an average size of between about 0.05 microns and about 0.5 microns, an average size of between about 0.05 microns and about 0.2 microns, between about 0.05 microns and about 0.15 microns, and preferably between about 0.05 microns and about 0.10 microns.

In some embodiments, the method further comprises, after forming the liposomal composition (wherein the liposomal composition comprises aqueous solution encapsulated in the liposomes and aqueous solution not encapsulated in the liposomes, i.e., non-encapsulated aqueous solution), removing peptide epoxyketone compound from the non-encapsulated aqueous solution in which the liposomes are dispersed. Removal of peptide expoxyketone compounds from the non-encapsulated aqueous solution can be accomplished, for example, using dialysis, ultracentrifugation, gel filtration, or combinations thereof.

In some embodiments, the method further comprise, after injecting the lipid solution into the aqueous solution to form the liposomal composition, adjusting the pH of the aqueous solution. The pH can be adjusted to, for example, a pH of between about pH 3.0 and about pH 7.0, preferably to a human physiological pH.

The method can further comprise, after injecting the lipid solution into the aqueous solution to form the liposomal composition, adding one or more excipients to the aqueous solution, for example, a pH adjusting agent (e.g., a buffer) and/or an agent to maintain isotonicity.

Examples of peptide epoxyketone compounds for use in the method include, but are not limited to, compound I. Preferred peptide epoxyketone compounds for use in liposomal compositions include compound II, compound III, compound IV, and, most preferably carfilzomib (compound V).

In a tenth aspect, the present invention relates to pharmaceutical liposomal compositions made by the method of the ninth aspect of the present invention; the liposomal composition comprising liposomes dispersed in the aqueous solution, wherein the liposomes comprise a peptide epoxyketone compound entrapped in the liposomes.

In an eleventh aspect, the present invention relates to a dry pharmaceutical composition formed by drying the pharmaceutical liposomal composition of the tenth aspect of the invention.

In a twelfth aspect, the present invention relates to methods of treating a disease or condition in a subject in need of treatment, comprising administering a therapeutically effective amount of a pharmaceutical liposomal composition, as described herein, comprising liposomes comprising a peptide epoxyketone compound. In some embodiments the methods of treating further comprise simultaneous, sequential, or separate administration of a therapeutically effective amount of another therapeutic agent, for example, a chemotherapeutic agent, a cytokine, a steroid, an immunotherapeutic agent, or combinations thereof. Examples of diseases or conditions that are treated using the pharmaceutical liposomal compositions of the present invention comprising peptide epoxyketone compounds include, but are not limited to, multiple myeloma, solid tumors, infections, and autoimmune diseases.

3.0.0 Pharmaceutical Compositions

The present invention relates to pharmaceutical liposomal compositions comprising peptide epoxyketone compounds (e.g., carfilzomib) and prodrugs thereof, dry pharmaceutical compositions comprising peptide epoxyketone compounds (e.g., carfilzomib) and prodrugs thereof, and methods of making and using such compositions.

3.1.0 Peptide Epoxyketone Compounds

Examples of peptide epoxyketone compounds useful in the practice of the present invention are described in U.S. Pat. No. 7,417,042, and include, but are not limited to, a peptide epoxyketone compound having the structure of formula I:

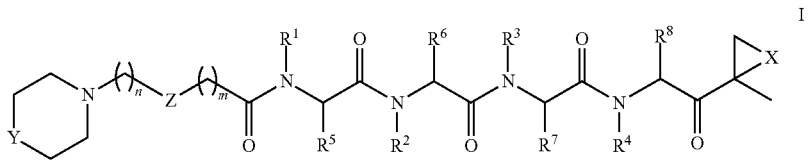

wherein X is O, NH, or N-alkyl; Y is NH, N-alkyl, O, or $C(R^9)_2$; Z is O or $C(R^9)_2$; $R^1$, $R^2$, $R^3$, and $R^4$ are all hydrogen; each $R^5$, $R^6$, $R^7$, $R^8$, and $R^9$ is independently selected from hydrogen, $C_{1-6}$alkyl, $C_{1-6}$hydroxyalkyl, $C_{1-6}$alkoxyalkyl, aryl, and $C_{1-6}$aralkyl, each of which is optionally substituted with a group selected from alkyl, amide, amine, carboxylic acid or a pharmaceutically acceptable salt thereof, carboxyl ester, thiol, and thioether; m is an integer from 0 to 2; and n is an integer from 0 to 2. Terms used to describe these compounds are further set forth in the "Definitions" section.

Examples of specific peptide epoxyketone compounds useful in the practice of the present invention include the following compounds having formulas II, III, and IV ("Ph" in the following compounds represents a phenyl group):

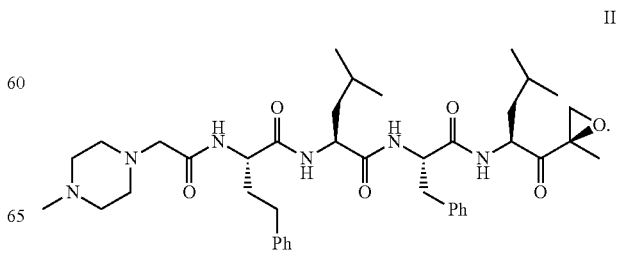

-continued

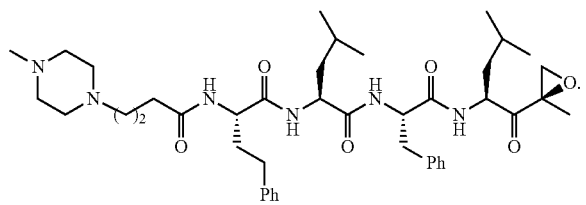

III

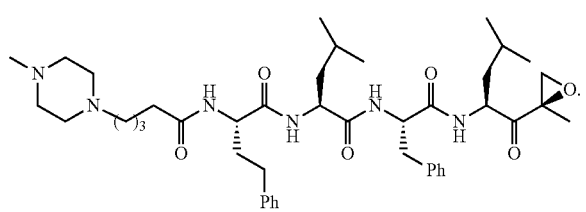

IV

In a preferred embodiment of the present invention, the peptide epoxyketone compound is carfilzomib having formula V:

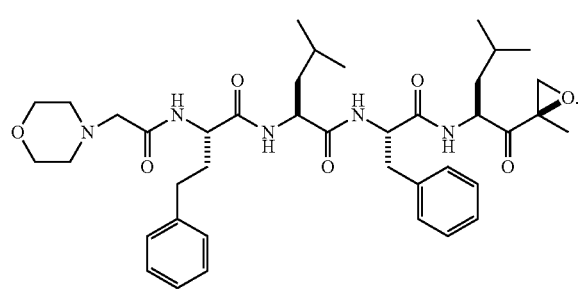

V

In the liposomal compositions of the present invention, the weight ratio of peptide epoxyketone compound:total lipid (wt. drug:wt. total lipid) is typically between about 0.005:0.995 and about 0.5:0.5 (in weight percent (wt. %) between about 0.5 wt. % and about 50 wt. % drug and between about 99.5 wt. % and about 50 wt. % total lipids). In preferred embodiments, the weight ratio of peptide epoxyketone compound:total lipid is between about 0.005: 0.995 and about 0.35:0.65 (in weight percent, between about 0.5 wt. % and about 35 wt. % drug and between about 99.5 wt. % and about 65 wt. % total lipids), preferably between about 0.01:0.99 and about 0.30:0.70 (in weight percent, between about 1 wt. % and about 30 wt. % drug and between about 99 wt. % and about 70 wt. % total lipids), and more preferably between about 0.01:0.99 and about 0.25:0.75 (in weight percent, between about 1 wt. % and about 25 wt. % drug and between about 99 wt. % and about 75 wt. % total lipids).

3.2.0 Liposome Components

Types of lipids used in the practice of the present invention include, but are not limited to phospholipids, sterols, and modifications and derivatives thereof. Additional amphipathic lipids can also be used in the practice of the present invention.

Preferred vesicle forming amphipathic lipids for use in the practice of the present invention include phospholipids and derivatives thereof. Phospholipids fall generally into three classes, neutral, cationic, and anionic.

Examples of phospholipids useful in the practice of the present invention include, but are not limited to, the following: phosphatidylcholine; L-α-phosphatidylcholine (egg phosphatidylcholine (EPC), or hydrogenated soy phosphatidylcholine (HSPC)); 1,2-distearoyl-sn-glycero-3-phosphocholine (DSPC); 1,2-dipalmitoyl-sn-glycero-3-phosphocholine (DPPC); phosphatidylserine (PS); phosphatidylinositol (PI); phosphatidylglycerol (PG); phosphatidylethanolamine (PE); dioleoyl phosphatidylglycerol (DOPG); 1,2-Dioleoyl-sn-glycero-3-phosphocholine (or dioleoyl phosphatidylcholine) (DOPC); dioleoyl phosphatidylserine (DOPS); 1,2-dileoyl-sn-glycero-3-phosphoethanolamine (DOPE); 1,2-Dioleoyl-sn-glycero-3-phosphate (DOPA); 1-Myristoyl-2-stearoyl-sn-glycero-3-phosphocholine (MSPC); 1,2-Dipalmitoyl-sn-glycero-3-phospho-rac-(1-glycerol) (DPPG); 1,2-Dimyristoyl-sn-glycero-3-phospho-rac-(1-glycerol) (DMPG); 1,2-Dimyristoyl-sn-glycero-3-phosphocholine (DMPC); 1,2-Distearoyl-sn-glycero-3-phospho-rac-(1-glycerol) (DSPG); 1-Palmitoyl-2-oleoyl-sn-glycero-3-phosphocholine (POPC); diacylphosphatidylcholine; diacylphosphatidic acid; N-dodecanoyl phosphatidylethanolamine: N-succinyl phosphatidylethanolamine: N-glutaryl phosphatidylethanolamine: lysylphosphatidylglycerol; sphingolipids (e.g., sphingomyelin); and mixtures thereof.

Further vesicle forming lipids useful in the practice of the present invention include, for example, N,N-dioleyl-N,N-dimethylammonium chloride (DODAC); N-(2,3-dioleyloxyl)propyl-N,N—N-triethylammonium chloride (DOTMA); N,N-distearyl-N,N-dimethylammonium bromide (DDAB); N-(2,3-dioleoyloxy)propyl)-N,N,N-trimethylammonium chloride (DOTAP); N-(1-(2,3-dioleyloxyl)propyl)-N-2-(sperminecarboxamido)ethyl)-N,N-dimethylammonium trifluoracetate (DOSPA); dioctadecylamidoglycylcarboxyspermine (DOGS); N-(1,2-dimyristyloxyprop-3-yl)-N,N-dimethyl-N-hydroxyethyl ammonium bromide (DMRIE); stearylamine; dicetyl phosphate; 0-oleoyl-γ-palmitoyl; and mixtures thereof.

Preferred lipids for use in the practice of the present invention include, but are not limited to: L-α-phosphatidylcholine (e.g., egg phosphatidylcholine (EPC), or hydrogenated soy phosphatidylcholine (HSPC)); 1,2-distearoyl-sn-glycero-3-phosphocholine (DSPC); 1,2-dipalmitoyl-sn-glycero-3-phosphocholine (DPPC); 1,2-Distearoyl-sn-glycero-3-phospho-rac-(1-glycerol) (DSPG); 1-Palmitoyl-2-oleoyl-sn-glycero-3-phosphocholine (POPC); sphingomyelin (SPH); 1,2-distearoyl-sn-glycero-3-phosphoethanolamine (DSPE); and combinations thereof. In some embodiments, the lipids of the liposomes comprise between about 20 to about 100 weight percent phospholipid, between about 30 and about 90 weight percent phospholipid, preferably between about 50 and about 75 weight percent phospholipid.

A variety of sterols and derivatives thereof (e.g., cholesterol) can be used to stabilize liposomes. Sterol-modified amphiphilic lipids are known in the art (see, e.g., U.S. Patent Application Publication No. 2011/0177156). Sterols for use in the practice of the present invention, such as cholesterol, also can be derivatized with a variety of hydrophilic polymers (PEG-cholesterol derivatives; see, e.g., U.S. Pat. No. 6,270,806). In an embodiment of the present invention, sterols or derivatives thereof can be added to the liposomal composition to stabilize the lipid bilayer. Preferred sterols for use in the practice of the present invention are cholesterol and its derivatives (e.g., cholesterol hemisuccinates; hydroxycholesterols; cholestens; ketocholestanols; cholesteryl acetates; cholesteryl linoleates; cholesteryl dodecanoates; cholesteryl palmitates; thiocholesterols; lysine-based cholesterols; hydroxyethylated cationic cholesterols). For example, the lipids of the liposomes of the liposomal compositions of the present invention can comprise between about 10 and about 50 weight percent cholesterol, between about 15 and about 40 weight percent cholesterol, preferably between about 15 and about 30 weight percent cholesterol.

In other embodiments, cholesterol is chemically modified with a ligand designed to be recognized by a particular organ or cell type such as a long chain fatty acid, an amino acid, an oligosaccharide, a hormone, an amino acid derivative, a protein, glycoprotein, modified protein, or the like. The resultant liposome is suitable for being targeted to a specific organ or cell type (see, e.g., U.S. Pat. No. 4,544,545).

Additional examples of liposomal compositions including targeting factors that can be used, in view of the teachings of the present specification, include U.S. Pat. Nos. 5,049, 390; 5,780,052; 5,786,214; 5,830,686; 6,056,973; 6,110, 666; 6,177,059; 6,245,427; 6,316,024; 6,524,613; 6,530, 944; 6,749,863; 6,803,360; 6,960,560; 7,060,291; 7,101, 985; and U.S. Patent Application Nos. 2002/0198164; 2003/ 0027779; 2003/0220284; 2003/0224037; 2003/0228285; 2003/143742; and 2004/0022842.

Steric stabilization refers to the colloidal stability conferred on the liposome by a variety of hydrophilic polymers or hydrophilic glycolipids, for example, polyethylene glycol and the ganglioside GM1. Liposomes can contain PEG-PE, GM1, or another such glycolipid or polymer that demonstrates a relatively long half-life in the general circulation. Hydrophilic polymers such as PEG and other polyethoxylated polymers can be used to shield liposomes to enhance the circulatory half-life of the liposome. Such hydrophilic polymers can be associated non-covalently with the liposomes or conjugated or covalently linked to a particular component of the liposome (e.g., PEG-derivatized lipids; such as 1,2-distearoyl-sn-glycero-3-phosphoethanolamine-N-[methoxy(polyethylene glycol)-2000] (ammonium salt) (mPEG-DSPE)). Additional exemplary hydrophilic polymers include, but are not limited to, polyvinyl alcohols, polylactic acids, polyglycolic acids, polyvinylpyrrolidones, polyacrylamides, polyglycerols, polyaxozlines, polyaminoacids (PAAs), and mixtures thereof.

In some embodiments of the liposomal compositions described herein, the lipids of the liposomes can comprise between about 0.1 and about 30 weight percent of a hydrophilic polymer-derivatized lipid, between about 5 and about 25 weight percent of a hydrophilic polymer-derivatized lipid, preferably between about 8 and about 20 weight percent of a hydrophilic polymer-derivatized lipid. Preferred hydrophilic polymers for use in the practice of the present invention are polyethylene glycols (e.g., phospholipids conjugated to monomethoxy polyethylene glycol, for example, 1,2-distearoyl-sn-glycero-3-phosphoethanolamine-N-[methoxy(polyethylene glycol)-2000] (mPEG-DSPE)).

Additional examples of liposomal compositions that can be used, in view of the teachings of the present specification, include: U.S. Pat. Nos. 4,789,633; 4,925,661; 4,983,397; 5,013,556; 5,534,241; 5,593,622; 5,648,478; 5,676,971; 5,756,069; 5,834,012; 5,846,458; 5,891,468; 5,945,122; 6,056,973; 6,057,299; 6,077,834; 6,126,966; 6,153,596; 6,287,593; 6,316,024; 6,387,397; 6,476,068; 6,586,559; 6,627,218; 6,723,338; 6,897,196; 6,936,272; 6,960,560; 7,122,202; 7,311,924; 7,361,640; and 7,901,708; and U.S. Patent Application Publication Nos. 2003/0072794; 2003/ 0082228; 2003/0166601; 2003/0203865 2003/0215490; 2003/0224037; 2004/0022842; 2004/0234588; and 2005/ 0136064.

The liposomal compositions typically comprise liposome entrapped peptide epoxyketone compounds and an aqueous carrier.

Typical excipients useful in the practice of the present invention include, but are not limited to, the following: carrier or vehicle (e.g., water or buffered aqueous solutions); pH adjusting agents; antioxidants (e.g., α-tocopherol, methionine, ascorbic acid, sodium thiosulfate, ethylenediaminetetraacetic acid, citric acid, cysteins, thioglycerol, thioglycolic acid, thiosorbitol, butylated hydroxanisol, butylated hydroxyltoluene, and propyl gallate, and mixtures thereof); agents to maintain isotonicity (e.g., sodium chloride, sugars, polyols (sugar alcohols), boric acid, sodium tartrate, propylene glycol, and mixtures thereof); one or more sugars (e.g., trehalose, maltose, sucrose, lactose, mannose, dextrose, fructose, etc.) or sugar alcohol (e.g., sorbitol, maltitol, lactitol, mannitol, glycerol, etc.); alcohol (e.g., ethanol, t-butanol, etc.); and preservatives (alcohols, benzoic acid, salicylic acid, phenol and its derivatives (e.g., cresol, p-cresol, m-cresol and o-cresol), cetrimide, BHA (butylated hydroxytoluene), BHA (butylated hydroxyanisole); and mixtures thereof).

pH adjusting agents useful in the practice of the present invention include, but are not limited to hydrochloric acid, sodium hydroxide, citric acid, phthalic acid, acetic acid, ascorbic acid, phosphate, glutamate, sodium or potassium succinate, tartrate, histidine, sodium or potassium phosphate, Tris (tris (hydroxymethyl)aminomethane), diethanolamine, sulfuric acid, and phosphoric acid. Buffers comprising both acids and bases/salts can also be used. Preferred pH adjusting agents comprise sulfuric acid and phosphoric acid.

In a preferred embodiment of the present invention, the liposomes can be rehydrated using buffered aqueous solutions (e.g., phosphate buffer saline (PBS)), 0.9% Saline, 5% Dextrose, 10% Sucrose, or water for injection (WFI) as the rehydration medium). In some embodiments, the pH of the aqueous phase of the liposomal compositions is adjusted, for example, to approximately human physiological pH (i.e., between about pH 6.5 and about pH 7.5). Excipients typically present in the aqueous phase include, but are not limited to, buffer systems, agents to maintain isotonicity, sugars, sugar alcohols, and/or preservatives.

Exemplary embodiments of liposomal compositions of peptide epoxyketones include, but are not limited to, the following: carfilzomib-EPC; carfilzomib-EPC-cholesterol; carfilzomib-DSPC; carfilzomib-DSPC-cholesterol; carfilzomib-DPPC; carfilzomib-DPPC-cholesterol; carfilzomib-sphingomyelin; carfilzomib-sphingomyelin-cholesterol.

Further examples comprise PEGylated liposomal compositions of peptide epoxyketones that include, but are not limited to, the following: carfilzomib-EPC-mPEG2000DSPE; carfilzomib-EPC-mPEG2000DSPE-cholesterol; carfilzomib-DSPC-mPEG2000DSPE; carfilzomib-DSPC-mPEG2000DSPE-cholesterol; carfilzomib-sphingomyelin-mPEG2000DSPE; and carfilzomib-sphingomyelin-mPEG2000DSPE-cholesterol.

Preferred embodiments of liposomal compositions of peptide epoxyketones include, but are not limited to, the following: carfilzomib-EPC-mPEG2000DSPE-cholesterol; carfilzomib-sphingomyelin-mPEG2000DSPE-cholesterol; and carfilzomib-HSPC-mPEG2000DSPE-cholesterol.

Examples of embodiments of liposomal compositions of the present invention are set forth in Examples 1, 7, 10, and 11. Further, examples of ranges of weight percents and ratios for drug:total lipid are presented in Table I; and examples of ranges of total lipid weight percents and total lipid weight ratios are presented in Table II. Accordingly, additional examples of preferred embodiments of liposomal compositions of the present invention include selecting a drug:total lipid combination from Table I and combining it with a total lipid combination from Table II (see, e.g., Example 1, Table 3).

TABLE I

Examples of Drug:Total Lipid Combinations

| Drug Weight Percent Range<br>Total Lipid Weight Percent Range | Drug:Total Lipid<br>Weight Ratio Range |
|---|---|
| between about 0.5 wt. % and about 50 wt. % peptide epoxyketone compound<br>between about 99.5 wt. % and about 50 wt. % total lipid | about 0.005:0.995 to about 0.5:0.5 |
| between about 0.5 wt. % and about 35 wt. % peptide epoxyketone compound<br>between about 99.5 wt. % and about 65 wt. % total lipid | about 0.005:0.995 to about 0.35:0.65 |
| between about 1 wt. % and about 30 wt. % peptide epoxyketone compound<br>between about 99 wt. % and about 70 wt. % total lipid | about 0.01:0.99 to about 0.30:0.70 |
| between about 1 wt. % and about 25 wt. % peptide epoxyketone compound<br>between about 99 wt. % and about 75 wt. % total lipid | about 0.01:0.99 to about 0.25:0.75 |

TABLE II

Examples of Total Lipid Combinations

| Lipid | Weight Percent Range | Total Lipid Weight Ratio Range (Phospholipid:Hydrophilic Polymer-derivatized Lipid:{Cholesterol or Cholesterol Derivative}) |
|---|---|---|
| Phospholipid | 100 wt. % | 1:0:0 |
| Phospholipid & {Cholesterol or Cholesterol Derivative} | between about 90 wt. % phospholipid & about 50 wt. % phospholipid<br>between about 10 wt. % cholesterol or derivative and about 50 wt. % cholesterol or derivative | about 0.9:0:0.1 to about 0.5:0:0.5 |
| Phospholipid & Hydrophilic Polymer-derivatized Lipid | between about 90 wt. % phospholipid & about 75 wt. % phospholipid<br>between about 10 wt. % hydrophilic polymer-derivatized lipid & about 25 wt. % hydrophilic polymer-derivatized lipid | about 0.9:0.1:0 to about 0.75:0.25:0 |
| Phospholipid, Hydrophilic Polymer-derivatized Lipid, & {Cholesterol or Cholesterol Derivative} | between about 83.3 wt. % phospholipid & about 57 wt. % phospholipid<br>between about 8.33 wt. % hydrophilic polymer-derivatized lipid & about 14 wt. % hydrophilic polymer-derivatized lipid<br>between about 8.33 wt. % cholesterol or derivative & about 29 wt. % cholesterol or derivative | about 0.833:0.0833:0.0833 to about 0.57:0.14:0.29 |

4.0.0 Preparing Liposomal Compositions

Liposomes can be prepared by a variety of techniques (e.g., Szoka, F., Jr., et al., "Comparative Properties and Methods of Preparation of Lipid Vesicles (Liposomes)," *Annual Review of Biophysics and Bioengineering*, June 1980, 9:467-508; U.S. Pat. No. 4,235,871) including reverse phase evaporation methods. The reverse phase evaporation vesicles initially have typical average sizes between about 2-4 microns.

In some embodiments, liposomes are formed by simple lipid-film hydration techniques (see, e.g., Examples 1 and 2). In this procedure, a mixture of liposome-forming lipids of the type described herein and peptide expoxyketone compounds are dissolved in a suitable organic solvent and evaporated in a vessel to form a thin film, which is then covered by an aqueous medium. The lipid film hydrates to form vesicles typically with sizes between about 0.1 to 10 microns.

Other embodiments of the present invention include, a method of passively encapsulating a hydrophobic, water-insoluble, peptide expoxyketone compound into the internal aqueous core of the liposome. Such encapsulation in the aqueous core can be facilitated using one or more solubilizing agent. Solubilizing agents increase the solubility of a peptide expoxyketone compound in an aqueous solution. Solubilizing agents include, for example, compounds to facilitate solubilization (e.g., cyclodextrin), pH adjusting agents, cosolvents, and combinations thereof. Advantages of encapsulating peptide expoxyketone compounds in the interior aqueous core of liposomes include greater protection from chemical and biological degradation, slower diffusion, and extended drug release profiles. Further, as described below in the Experimental Section, the liposomal compositions comprising peptide epoxyketone compounds of the present invention enhance the therapeutic window of peptide epoxyketone compounds by: improving in vivo half-life relative to non-liposomal compositions comprising peptide epoxyketone compounds; providing desirable pharmacodynamic profiles; and providing anti-tumor activity in a human tumor xenograft model greater than or equal to non-liposomal compositions comprising peptide epoxyketone compounds. Further, the liposomal compositions of the present invention demonstrated improved tolerability of liposomal compositions comprising peptide epoxyketone compounds relative to non-liposomal compositions comprising peptide epoxyketone compounds.

Cyclodextrins are an example of compounds to facilitate solubilization of peptide expoxyketone compounds in aqueous solution. Cyclodextrins can be charged or neutral, native (cyclodextrins α, β, γ, δ, ε), branched or polymerized. In certain aspects, cyclodextrins can be chemically modified, for example, by substitution of one or more hydroxypropyls by groups such as alkyls, aryls, arylalkyls, glycosidics, or by etherification, esterification with alcohols or aliphatic acids. From these groups, particular preference is given to those from hydroxypropyl, methyl, and sulfobutylether groups (see, e.g., Stella V. J., et al., *Toxicol. Pathol.* 36(1):30-42 (2008)). In certain aspects, cyclodextrins comprise six, seven, or eight glucopyranose units.

Cyclodextrins include α-cyclodextrin, β-cyclodextrin, and γ-cylcodextrin. Suitable α-cyclodextrins include but are not limited to hydroxypropyl-α-cyclodextrin and hydroxyethyl-α-cyclodextrin. Suitable β-cyclodextrins include but are not limited to hydroxypropyl-β-cyclodextrin (e.g., 2-hydroxypropyl cyclodextrin), carboxymethyl-β-cyclodextrin, dihydroxypropyl-β-cyclodextrin, hydroxyethyl-β-cyclodextrin, 2,6-di-O-methyl-β-cyclodextrin, methyl-β-cyclodextrin, randomly methylated cylcodextrin, and sulfated-β-cyclodextrin. Suitable γ-cyclodextrins include hydroxypropyl γ-cyclodextrin, dihydroxypropyl-γ-cyclodextrin, hydroxyethyl γ-cyclodextrin, and sulfated-γ-cyclodextrin.

Preferred cyclodextrins for use in the practice of the present invention include β-cyclodextrins (such as sulfobutyl ether-β-cyclodextrins (abbreviated as SBE-β-CD or SBE-B-CD; e.g., CAPTISOL® (Ligand Pharmaceuticals, Inc., La Jolla, Calif.), see also U.S. Pat. Nos. 4,535,152; 4,727,064; 5,134,127; 5,173,481); or hydroxypropyl-beta-cyclodextrin (HP-13-CD; Janssen, Titusville N.J.; see also Gould S, et al., *Food Chem. Toxicol.* 43(10):1451-9 (2005)); see also U.S. Pat. Nos. 4,920,214; 5,385,891; 5,718,905; and 6,046,177).

Peptide expoxyketone compounds are often hydrophobic and have low solubility in water. Peptide expoxyketone compounds have increased aqueous solubility in acidic solutions. Accordingly, lowering the pH of the aqueous solution in which a peptide expoxyketone compound is being dissolved can enhance aqueous solubilization. For example, the pH of the aqueous solution can be lowered using a pH adjusting agent to a pH of between about pH 0.5 and about pH 3, preferably to a pH of between about pH 0.5 and about pH 2 using an acid, for example, hydrochloric acid. Examples of pH adjusting agents are listed above. Preferred pH adjusting agents for solubilization of peptide epoxyketone compounds include, but are not limited to, hydrochloric acid, citric acid, methanesulfonic acid, sulfuric acid, tartaric acid, acetic acid, phosphoric acid, and/or maleic acid. A preferred pH for solubilization is typically between about pH 1 and about pH 2.

Further, solubility of peptide expoxyketone compounds in aqueous solutions can be increased by the use of cosolvent solubilization. Examples of cosolvents as solubilizing agents include, but are not limited to, dimethylsulfoxide, methylpyrrolidone, dimethylimidazolidinone, tetrahydrofuran, N,N-dimethylacetamide, propylene glycol, benzyl alcohol, polyethylene glycol, ethanol, methanol, isopropyl alcohol, dimethylformamide, and combinations thereof. Preferred cosolvents include dimethylsulfoxide, methylpyrrolidone, propylene glycol, polyethylene glycol, ethanol, methanol, isopropyl alcohol, dimethylformamide, and combinations thereof.

As noted above, solubility of peptide expoxyketone compounds in aqueous solutions can be increased by use of solubilizing agents, including, but not limited to, compounds, pH adjusting agents, cosolvents, and combinations thereof.

Metals and metal ions can also be used to facilitate loading of drug into liposomes (see, e.g., WO/2003/028697 and U.S. Pat. Nos. 5,466,467; 5,663,387; and 5,837,282). Such metals and metal ions include, but are not limited to, divalent metal cations and transition metals (e.g., Mn, Ca, Fe, Co, Ni, Cu, Zn, V, Ti, Cr, Rh, Ru, Mo, and Pd). Drug can be stably entrapped within transition metal-containing liposomes, typically as a result of metal/drug complexation (see, e.g., Ramsay E., et al., *Pharm Res.* 23(12):2799-808 (2006)).

In some embodiments, liposomes are formed by a thin film hydration method followed by rehydration using an aqueous solution comprising a peptide expoxyketone compound and solubilizing agent. In such a method, a lipid film is formed wherein the lipid film comprises, for example, any one or combination of lipids, including but not limited to the following: L-α-phosphatidylcholine (e.g., egg phosphatidylcholine (EPC), or hydrogenated soy phosphatidylcholine (HSPC)); 1,2-distearoyl-sn-glycero-3-phosphocholine (DSPC); 1,2-dipalmitoyl-sn-glycero-3-phosphocholine (DPPC); 1,2-Distearoyl-sn-glycero-3-phospho-rac-(1-glycerol) (DSPG); 1-Palmitoyl-2-oleoyl-sn-glycero-3-phosphocholine (POPC); sphingomyelin (SPH); 1,2-distearoyl-sn-glycero-3-phosphoethanolamine (DSPE); phospholipids conjugated to monomethoxy polyethylene glycol (mPEG); and cholesterol. The lipids are typically dissolved in an organic solvent (e.g., Methanol:Chloroform) followed by solvent removal to form a lipid film.

The peptide expoxyketone compound is solubilized in an aqueous solution comprising, for example, about 1% to about 60% (w/w), preferably about 5% to about 40% of a solubilizing agent (e.g., sulfobutylether-betacyclodextrin or hydroxypropyl-betacyclodextrin). The aqueous solution can also include, for example, a pH adjusting agent (e.g., citrate buffer, ~pH 3, or Glycine-HCl; ~pH 2) and/or a cosolvent for solubilization of the peptide expoxyketone compound. The aqueous drug solution is used to rehydrate the lipid film. Upon rehydration, self-assembling vesicles form concentric lipid bilayers encapsulating an internal aqueous volume (i.e., aqueous core) of the aqueous solution comprising the peptide expoxyketone compound. The unencapsulated free drug can be removed, for example, by centrifugation and the liposomal composition washed, for example, with phosphate buffer saline. Example 7 describes making liposomal compositions following this method.

In other embodiments, liposomes are formed by a lipid solution injection method wherein a lipid solution is injected into an aqueous solution comprising a peptide expoxyketone compound. This method typically comprises solubilizing a peptide expoxyketone compound (e.g., in different solid states, such as crystalline or amorphous), using a solubilizing agent (e.g., pH control, with or without, cosolvent solubilization) in an aqueous solution. The lipids are dissolved in a solvent, for example, an organic solvent (such as an alcohol (e.g., ethanol) or an ether), followed by injection into the aqueous solution comprising the peptide expoxyketone compound while stirring. Liposome vesicles are formed upon injection into the aqueous solution trapping small amounts of aqueous solution in the internal aqueous compartment(s) of the vesicles. Example 10 describes making liposomal compositions following this method. One advantage of this method is that it is scalable.

In some embodiments, for example for pH adjustment and/or removal of solvent and/or a cosolvent, the methods of the invention further comprise processing the liposomal composition using dialysis, desalting, buffer exchange, and/or gel filtration.

A liposomal composition of the present invention generally contains a non-homogenous mixture of lipids, peptide epoxyketone compound, and aqueous solution, wherein the liposomes are of substantially homogenous size, with an average size of less than about 1 micron, preferably between about 0.01 microns to about 1.0 micron, preferably between about 0.05 microns and about 0.5 microns, between about 0.05 microns and about 0.20 microns, between about 0.05 microns and about 0.15 microns, and preferably between about 0.05 microns and about 0.10 microns. In some embodiments, liposomes of the liposomal compositions of the present invention have average diameters of less than about 0.2 microns. Sizing serves to eliminate larger liposomes and to produce a defined size range having optimal pharmacokinetic properties.

One effective sizing method for vesicles involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. The liposomes can be extruded through successively smaller-pore membranes, to achieve a gradual reduction in liposome size. This method of liposome sizing is used in preparing homogeneous-size vesicle compositions. A more recent method involves extrusion through an asymmetric ceramic filter (see, e.g., U.S. Pat. No. 4,737,323). Homogenization methods are also useful for down-sizing liposomes to sizes of 0.1 micron or less.

Sonicating a liposome suspension either by bath or probe sonication can be used to produce progressive size reduction down to small unilamellar vesicles (SUVs) less than about 0.05 microns in size. Homogenization is another method that relies on shearing energy to fragment large liposomes into smaller ones. In a typical homogenization procedure, vesicles are recirculated through a standard emulsion homogenizer until selected liposome sizes, typically between about 0.1 and 0.5 microns, are observed. In both methods, the particle size distribution can be monitored by conventional laser-beam particle size discrimination. A further sizing method includes use of a microfluidizer.

Centrifugation and molecular sieve chromatography are other methods available for producing a liposome suspension with particle sizes below a selected threshold less than 1 micron. These two methods both involve preferential removal of larger liposomes, rather than conversion of large particles to smaller ones.

Examples of preparation, rehydration, and characterization of liposomal compositions of the present invention are presented in Example 1, Example 2, Example 3, Example 7, Example 10, and Example 11 herein.

In one aspect, the present invention includes methods for the preparation of the liposomal compositions described herein. In one embodiment, a method of making a liposomal composition comprises mixing (typically dissolving) lipid and peptide epoxyketone compound in a suitable solvent, evaporating the solvent to produce a dried film, rehydrating the dried film (which in this embodiment comprises lipid and peptide epoxyketone compound) to form liposomes, and sizing the liposomes. In another embodiment, a method of making a liposomal composition comprises a thin film hydration method which produces a dried film comprising liposomal components followed by rehydration using an aqueous solution comprising a peptide expoxyketone compound as well as a solubilizing agent (e.g., a pH adjusting agent, and/or a cosolvent). In yet another embodiment, a method of making a liposomal composition comprises dissolving lipid(s) in solvent(s) and injecting the resulting lipid solution into an aqueous solution comprising a peptide expoxyketone compound as well as a solubilizing agent (e.g., a pH adjusting agent, and/or a cosolvent). In yet another embodiment, a remote loading method (using, e.g., pH-gradient loading; see, e.g., Avnir, Y., et al., *Arthritis & Rheumatism*, 58(1):119-129 (2008); Čeh, B., et al., *Journal of Colloid and Interface Science*, 185(1): 9-18 (1997); Vemuri S, et al., *J. Pharm. Pharmacol.*, 46(10):778-83 (1994); Dos Santos, N., et al., *Biochimica et Biophysica Acta*, 1661:47-60 (2004)) for loading drug into liposomes is used to prepare the liposomal compositions described herein. Remote loading methods typically produce higher drug loading into liposomes compared to thin-film rehydration methods.

The present invention also includes liposomal compositions comprising peptide expoxyketone compounds made by the methods described herein.

Dry pharmaceutical compositions comprising one or more lipids and a peptide epoxyketone compound can be formed by drying the liposomal compositions described herein, for example, by lyophilization, desiccation, freeze-drying, spray-drying, or similar method. In some embodiments, dry pharmaceutical compositions further comprise additional excipients, for example cryoprotectant agents (e.g., glycerol, dimethylamine, dimethylsulfoxide), glass transition modifying agents (e.g. sugars, polyols, polymers, amino acids), and/or other stabilizing excipients. Such dry pharmaceutical compositions can be rehydrated for use in the methods of the present invention. The rehydration media used for reconstitution of such dry pharmaceutical compositions can include excipients including, but not limited to, a pH adjusting agent, an antioxidant, an agent to maintain isotonicity, a sugar, a sugar alcohol, an alcohol, and/or a preservative.

5.0.0 Uses of the Liposomal Compositions of the Present Invention

The biological consequences of proteasome inhibition are numerous. Proteasome inhibition has been suggested as a prevention and/or treatment of a multitude of diseases including, but not limited to, proliferative diseases, neurotoxic/degenerative diseases, Alzheimer's, ischemic conditions, inflammation, auto-immune diseases, HIV, cancers, organ graft rejection, septic shock, inhibition of antigen presentation, decreasing viral gene expression, parasitic infections, conditions associated with acidosis, macular degeneration, pulmonary conditions, muscle wasting diseases, fibrotic diseases, bone and hair growth diseases. Therefore, pharmaceutical formulations for very potent, proteasome-specific compounds, such as the epoxy ketone class of molecules, provide a means of administering a drug to a subject and treating these conditions.

At the cellular level, the accumulation of polyubiquitinated proteins, cell morphological changes, and apoptosis have been reported upon treatment of cells with various proteasome inhibitors. Proteasome inhibition has also been suggested as a possible antitumor therapeutic strategy. The fact that epoxomicin was initially identified in a screen for antitumor compounds validates the proteasome as an antitumor chemotherapeutic target. Accordingly, these liposomal compositions are useful for treating cancer.

Both in vitro and in vivo models have shown that malignant cells, in general, are susceptible to proteasome inhibition. In fact, proteasome inhibition has already been validated as a therapeutic strategy for the treatment of multiple myeloma. This could be due, in part, to the highly proliferative malignant cell's dependency on the proteasome system to rapidly remove proteins (Rolfe, et al., *J. Mol. Med.* 75:5-17 (1997); Adams, *Nature* 4: 349-360 (2004)). Therefore, provided herein is a method of treating cancers comprising administering to a subject in need of such treatment a therapeutically effective amount of a liposomal composition of a peptide expoxyketone compound as provided herein.

Cancer refers to diseases of blood, bone, organs, skin tissue and the vascular system, including, but not limited to, cancers of the bladder, blood, bone, brain, breast, cervix, chest, colon, endrometrium, esophagus, eye, head, kidney, liver, lung, lymph nodes, mouth, neck, ovaries, pancreas, prostate, rectum, renal, skin, stomach, testis, throat, and uterus. Specific cancers include, but are not limited to, leukemia (acute lymphocytic leukemia (ALL), acute myelogenous leukemia (AML), chronic lymphocytic leukemia (CLL), chronic myelogenous leukemia (CML), hairy cell leukemia, mature B cell neoplasms (small lymphocytic lymphoma, B cell prolymphocytic leukemia, lymphoplasmacytic lymphoma (such as Waldenström's macroglobulinemia), splenic marginal zone lymphoma, plasma cell myeloma, plasmacytoma, monoclonal immunoglobulin deposition diseases, heavy chain diseases, extranodal marginal zone B cell lymphoma (MALT lymphoma), nodal marginal zone B cell lymphoma (NMZL), follicular lymphoma, mantle cell lymphoma, diffuse B cell lymphoma, mediastinal (thymic) large B cell lymphoma, intravascular large B cell lymphoma, primary effusion lymphoma and Burkitt lymphoma/leukemia), mature T cell and natural killer (NK) cell neoplasms (T cell prolymphocytic leukemia, T cell large granular lymphocytic leukemia, aggressive NK cell leukemia, adult T cell leukemia/lymphoma, extranodal NK/T cell lymphoma, enteropathy-type T cell lymphoma, hepatosplenic T cell lymphoma, blastic NK cell lymphoma, mycosis fungoides (Sezary syndrome), primary cutaneous anaplastic large cell lymphoma, lymphomatoid papulosis, angioimmunoblastic T cell lymphoma, unspecified peripheral T cell lymphoma and anaplastic large cell lymphoma), Hodgkin lymphoma (nodular sclerosis, mixed celluarity, lymphocyte-rich, lymphocyte depleted or not depleted, nodular lymphocyte-predominant), myeloma (multiple myeloma, indolent myeloma, smoldering myeloma), chronic myeloproliferative disease, myelodysplastic/myeloproliferative disease, myelodysplastic syndromes, immunodeficiency-associated lymphoproliferative disorders, histiocytic and dendritic cell neoplasms, mastocytosis, chondrosarcoma, Ewing sarcoma, fibrosarcoma, malignant giant cell tumor, myeloma bone disease, osteosarcoma, breast cancer (hormone dependent, hormone independent), gynecological cancers (cervical, endometrial, fallopian tube, gestational trophoblastic disease, ovarian, peritoneal, uterine, vaginal and vulvar), basal cell carcinoma (BCC), squamous cell carcinoma (SCC), malignant melanoma, dermatofibrosarcoma protuberans, Merkel cell carcinoma, Kaposi's sarcoma, astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, teratoma, malignant mesothelioma (peritoneal mesothelioma, pericardial mesothelioma, pleural mesothelioma), gastro-entero-pancreatic or gastroenteropancreatic neuroendocrine tumor (GEP-NET), carcinoid, pancreatic endocrine tumor (PET), colorectal adenocarcinoma, colorectal carcinoma, aggressive neuroendocrine tumor, leiomyosarcomamucinous adenocarcinoma, Signet Ring cell adenocarcinoma, hepatocellular carcinoma, cholangiocarcinoma, hepatoblastoma, hemangioma, hepatic adenoma, focal nodular hyperplasia (nodular regenerative hyperplasia, hamartoma), non-small cell lung carcinoma (NSCLC) (squamous cell lung carcinoma, adenocarcinoma, large cell lung carcinoma), small cell lung carcinoma, thyroid carcinoma, prostate cancer (hormone refractory, androgen independent, androgen dependent, hormone-insensitive), and soft tissue sarcomas (fibrosarcoma, malignant fibrous hystiocytoma, dermatofibrosarcoma, liposarcoma, rhabdomyosarcoma leiomyosarcoma, hemangiosarcoma, synovial sarcoma, malignant peripheral nerve sheath tumor/neurofibrosarcoma, extraskeletal osteosarcoma).

In some embodiments, a liposomal composition comprising a peptide expoxyketone compound as provided herein, or a pharmaceutical composition comprising the same, can be administered to treat multiple myeloma in a subject. For example, multiple myeloma can include refractory and/or refractory multiple myeloma.

Many tumors of the haematopoietic and lymphoid tissues are characterized by an increase in cell proliferation, or a particular type of cell. The chronic myeloproliferative diseases (CMPDs) are clonal haematopoietic stem cell disorders characterized by proliferation in the bone marrow of one or more of the myeloid lineages, resulting in increased numbers of granulocytes, red blood cells and/or platelets in the peripheral blood. As such, use of a proteasome inhibitor for the treatment of such diseases is attractive and being examined (Cilloni, et al., *Haematologica* 92: 1124-1229 (2007)). CMPD can include chronic myelogenous leukemia, chronic neutrophilic leukemia, chronic eosinophilic leukemia, polycythaemia vera, chronic idiopathic myelofibrosis, essential thrombocythaemia and unclassifiable chronic myeloproliferative disease. Provided herein is a method of treating CMPD comprising administering to a subject in need of such treatment a therapeutically effective amount of the liposomal compositions comprising peptide epoxyketone compounds disclosed herein.

Myelodisplastic/myeloproliferative diseases, such as chronic myelomonocytic leukemia, atypical chronic myeloid leukemia, juvenile myelomonocytic leukemia and unclassifiable myelodysplastic/myeloproliferative disease, are characterized by hypercellularity of the bone marrow due to proliferation in one or more of the myeloid lineages. Inhibiting the proteasome with a liposomal composition comprising a peptide epoxyketone compound described herein, can serve to treat these myelodisplatic/myeloproliferative diseases by providing a subject in need of such treatment a therapeutically effective amount of the liposomal composition.

Myelodysplastic syndromes (MDS) refer to a group of hematopoietic stem cell disorders characterized by dysplasia and ineffective haematopoiesis in one or more of the major myeloid cell lines. Targeting NF-kB with a proteasome inhibitor in these hematologic malignancies induces apoptosis, thereby killing the malignant cell (Braun, et al., *Cell Death and Differentiation* 13:748-758 (2006)). Further provided herein is a method to treat MDS comprising administering to a subject in need of such treatment a therapeutically effective amount of a liposomal composition comprising a peptide epoxyketone compound provided herein. MDS includes refractory anemia, refractory anemia with ringed sideroblasts, refractory cytopenia with multilineage dysplasia, refractory anemia with excess blasts, unclassifiable myelodysplastic syndrome, and myelodysplastic syndrome associated with isolated del (5q) chromosome abnormality.

Mastocytosis is a proliferation of mast cells and their subsequent accumulation in one or more organ systems. Mastocytosis includes, but is not limited to, cutaneous mastocytosis, indolent systemic mastocytosis (ISM), systemic mastocytosis with associated clonal haematological non-mast-cell-lineage disease (SM-AHNMD), aggressive systemic mastocytosis (ASM), mast cell leukemia (MCL), mast cell sarcoma (MCS) and extracutaneous mastocytoma. Further provided herein is a method to treat mastocytosis comprising administering a therapeutically effective amount of the compound disclosed herein to a subject diagnosed with mastocytosis.

The proteasome regulates NF-κB, which in turn regulates genes involved in the immune and inflammatory response. For example, NF-κB is required for the expression of the immunoglobulin light chain κ gene, the IL-2 receptor α-chain gene, the class I major histocompatibility complex gene, and a number of cytokine genes encoding, for example, IL-2, IL-6, granulocyte colony-stimulating factor, and IFN-β (Palombella, et al., *Cell* 78:773-785 (1994)). Thus, provided herein are methods of affecting the level of expression of IL-2, MHC-I, IL-6, TNFα, IFN-β or any of the other previously-mentioned proteins, each method comprising administering to a subject a therapeutically effective amount of a liposomal composition comprising a peptide expoxyketone compound as disclosed herein.

Also provided herein is a method of treating an autoimmune disease in a subject comprising administering a therapeutically effective amount of a liposomal composition of a peptide expoxyketone compound described herein. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome (ARDS)); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitus); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; antiglomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Beheet disease; giant cell arteritis; immune complex nephritis; IgA nephropathy; IgM polyneuropathies; and immune thrombocytopenic purpura (ITP) or autoimmune thrombocytopenia.

The immune system screens for autologous cells that are virally infected, have undergone oncogenic transformation, or present unfamiliar peptides on their surface. Intracellular proteolysis generates small peptides for presentation to T-lymphocytes to induce MHC class I-mediated immune responses. Thus, provided herein is a method of using a liposomal composition comprising a peptide epoxyketone compound provided herein as an immunomodulatory agent for inhibiting or altering antigen presentation in a cell, comprising exposing the cell (or administering to a subject) to the compound described herein. Specific embodiments include a method of treating graft or transplant-related diseases, such as graft-versus-host disease or host versus-graft disease in a subject, comprising administering a therapeutically effective amount of the compound described herein. Grafts include such diverse material as, for example, isolated cells such as islet cells; tissue such as the amniotic membrane of a newborn, bone marrow, hematopoietic precursor cells, and ocular tissue, such as corneal tissue; and organs such as skin, heart, liver, spleen, pancreas, thyroid lobe, lung, kidney, tubular organs (e.g., intestine, blood vessels, or esophagus). The tubular organs can be used to replace damaged portions of esophagus, blood vessels, or bile duct. The skin grafts can be used not only for burns, but also as a dressing to damaged intestine or to close certain defects such as diaphragmatic hernia. The graft is derived from any mammalian source, including human, whether from cadavers or living donors. In some cases, the donor and recipient is the same subject. In some embodiments, the graft is bone marrow or an organ such as heart and the donor of the graft and the host are matched for HLA class II antigens.

Histiocytic and dendritic cell neoplasms are derived from phagocytes and accessory cells, which have major roles in the processing and presentation of antigens to lymphocytes. Depleting the proteasome content in dendritic cells has been shown to alter their antigen-induced responses (Chapatte, et al., *Cancer Res.* (2006) 66:5461-5468). In some embodiments, a liposomal composition comprising a peptide expoxyketone compound provided herein can be administered to a subject with histiocytic or dendritic cell neoplasm. Histiocytic and dendritic cell neoplasms include histiocytic sarcoma, Langerhans cell histiocytosis, Langerhans cell sarcoma, interdigitating dendritic cell sarcoma/tumor, follicular dendritic cell sarcoma/tumor and non-specified dendritic cell sarcoma.

Inhibition of the proteasome has been shown to be beneficial to treat diseases whereby a cell type is proliferating and immune disorders; thus, in some embodiments, the treatment of lymphoproliferative diseases (LPD) associated with primary immune disorders (PID) is provided comprising administering a therapeutically effective amount of a liposomal composition comprising a peptide epoxyketone compound to a subject in need thereof. The most common clinical settings of immunodeficiency associated with an increased incidence of lymphoproliferative disorders, including B-cell and T-cell neoplasms and lymphomas, are primary immunodeficiency syndromes and other primary immune disorders, infection with the human immunodeficiency virus (HIV), iatrogenic immunosuppression in subjects who have received solid organ or bone marrow allografts, and iatrogenis immunosuppression associated with methotrexate treatment. Other PIDs commonly associated with LPDs, but not limited to, are ataxia telangiectasia (AT), Wiskott-Aldrich syndrome (WAS), common variable immunodeficiency (CVID), severe combined immunodeficiency (SCID), X-linked lymphoproliferative disorder (XLP), Nijmegen breakage syndrome (NBS), hyper-IgM syndrome, and autoimmune lymphoproliferative syndrome (ALPS).

Proteasome inhibition has also been associated with inhibition of NF-κB activation and stabilization of p53 levels. Thus, compositions provided herein may also be used to inhibit NF-κB activation, and stabilize p53 levels in cell culture. Since NF-κB is a key regulator of inflammation, it is an attractive target for anti-inflammatory therapeutic intervention. Thus, liposomal compositions comprising peptide epoxyketone compounds provided herein may be useful for the treatment of conditions associated with inflammation, including, but not limited to COPD, psoriasis, asthma, bronchitis, emphysema, and cystic fibrosis.

The disclosed liposomal compositions comprising peptide epoxyketone compounds can be used to treat conditions mediated directly by the proteolytic function of the proteasome such as muscle wasting, or mediated indirectly via proteins that are processed by the proteasome such as NF-κB. The proteasome participates in the rapid elimination and post-translational processing of proteins (e.g., enzymes) involved in cellular regulation (e.g., cell cycle, gene transcription, and metabolic pathways), intercellular communication, and the immune response (e.g., antigen presentation). Specific examples discussed below include β-amyloid protein and regulatory proteins such as cyclins and transcription factor NF-κB.

In one embodiment of the present invention, the liposomal compositions comprising peptide epoxyketone compounds are useful for the treatment of cancer. Compounds of the invention also can be used to inhibit NF-κB activation, and stabilize p53 levels in cell culture.

In one embodiment of the present invention, the liposomal compositions can be used for anti-inflammatory therapeutic intervention in treating conditions associated with chronic inflammation, including, but not limited to COPD, psoriasis, bronchitis, emphysema, and cystic fibrosis.

In another embodiment of the present invention, the liposomal compositions can be used to treat neurodegenerative diseases and conditions, including, but not limited to: stroke; ischemic damage to the nervous system; neural trauma (e.g., percussive brain damage, spinal cord injury, and traumatic damage to the nervous system); multiple sclerosis and other immune-mediated neuropathies (e.g., Guillain-Barre syndrome and its variants, acute motor axonal neuropathy, acute inflammatory demyelinating polyneuropathy, and Fisher Syndrome); HIV/AIDS dementia complex; axonomy; diabetic neuropathy; Parkinson's disease; Huntington's disease; multiple sclerosis; bacterial, parasitic, fungal, and viral meningitis; encephalitis; vascular dementia; multi-infarct dementia; Lewy body dementia; frontal lobe dementia such as Pick's disease; subcortical dementias (such as Huntington or progressive supranuclear palsy); focal cortical atrophy syndromes (such as primary aphasia); metabolic-toxic dementias (such as chronic hypothyroidism or B12 deficiency); and dementias caused by infections (such as syphilis or chronic meningitis).

Alzheimer's disease is characterized by extracellular deposits of β-amyloid protein (β-AP) in senile plaques and cerebral vessels. β-AP is a peptide fragment of 39 to 42 amino acids derived from an amyloid protein precursor (APP). At least three isoforms of APP are known (695, 751, and 770 amino acids). Alternative splicing of mRNA generates the isoforms; normal processing affects a portion of the β-AP sequence, thereby preventing the generation of β-AP. It is believed that abnormal protein processing by the proteasome contributes to the abundance of β-AP in the Alzheimer brain. The APP-processing enzyme in rats contains about ten different subunits (22 kDa-32 kDa). The 25 kDa subunit has an N-terminal sequence of X-Gln-Asn-Pro-Met-X-Thr-Gly-Thr-Ser, which is identical to the β-subunit of human macropain (Kojima, S., et al., Fed. Eur. Biochem. Soc. 304:57-60 (1992)). The APP-processing enzyme cleaves at the Gln15-Lys16 bond; in the presence of calcium ion, the enzyme also cleaves at the Met-1-Asp1 bond, and the Asp1-Ala2 bonds to release the extracellular domain of β-AP.

In yet another embodiment of the present invention, the liposomal compositions can be used as a treatment for Alzheimer's disease, comprising administering to a subject an effective amount of peptide epoxyketone-containing liposomal compositions disclosed herein. In such cases, the liposomal compositions reduce the rate of β-AP processing, reduce the rate of β-AP plaque formation, reduce the rate of β-AP generation, and reduce the clinical signs of Alzheimer's disease.

The proteasome degrades many proteins in maturing reticulocytes and growing fibroblasts. In cells deprived of insulin or serum, the rate of proteolysis nearly doubles. Inhibiting the proteasome reduces proteolysis, thereby reducing both muscle protein loss and the nitrogenous load on kidneys or liver. Liposomal compositions comprising peptide epoxyketone compounds as provided herein are useful for treating conditions such as cancer, chronic infectious diseases, fever, muscle disuse (atrophy) and denervation, nerve injury, fasting, renal failure associated with acidosis, and hepatic failure. See, e.g., U.S. Pat. No. 5,340,736. Methods of treatment include: reducing the rate of muscle protein degradation in a cell; reducing the rate of intracellular protein degradation; reducing the rate of degradation of p53 protein in a cell; and inhibiting the growth of p53-related cancers. Each of these methods includes contacting a cell (in vivo or in vitro, e.g., a muscle in a subject) with an effective amount of a pharmaceutical liposomal composition disclosed herein.

Other embodiments of the present invention relate to methods for treating cachexia and muscle-wasting diseases, cancers, chronic infectious diseases, fever, muscle disuse (atrophy) and denervation, nerve injury, fasting, renal failure associated with acidosis, diabetes, and hepatic failure. Embodiments of the invention encompass methods for: reducing the rate of muscle protein degradation in a cell; reducing the rate of intracellular protein degradation; reducing the rate of degradation of p53 protein in a cell; and inhibiting the growth of p53-related cancers.

Fibrosis is the excessive and persistent formation of scar tissue resulting from the hyperproliferative growth of fibroblasts and is associated with activation of the TGF-β signaling pathway. Fibrosis involves extensive deposition of extracellular matrix and can occur within virtually any tissue or across several different tissues. Normally, the level of intracellular signaling protein (Smad) that activate transcription of target genes upon TGF-β stimulation is regulated by proteasome activity. However, accelerated degradation of the TGF-β signaling components has been observed in cancers and other hyperproliferative conditions.

Another protein processed by the proteasome is NF-κB, a member of the Rel protein family. The Rel family of transcriptional activator proteins can be divided into two groups. The first group requires proteolytic processing, and includes p50 (NF-κB1, 105 kDa) and p52 (NF-κ2, 100 kDa). The second group does not require proteolytic processing, and includes p65 (RelA, Rel (c-Rel), and RelB). Both homo- and heterodimers can be formed by Rel family members; NF-κB, for example, is a p50-p65 heterodimer. After phosphorylation and ubiquitination of IκB and p105, the two proteins are degraded and processed, respectively, to produce active NF-κB which translocates from the cytoplasm to the nucleus. Ubiquitinated p105 is also processed by purified proteasomes (Palombella, et al., Cell 78:773-785 (1994)). Active NF-κB forms a stereospecific enhancer complex with other transcriptional activators and, e.g., HMG I(Y), inducing selective expression of a particular gene.

NF-κB regulates genes involved in the immune and inflammatory response, and mitotic events. For example, NF-κB is required for the expression of the immunoglobulin light chain κ gene, the IL-2 receptor α-chain gene, the class I major histocompatibility complex gene, and a number of cytokine genes encoding, for example, IL-2, IL-6, granulocyte colony-stimulating factor, and IFN-β (Palombella, et al., Cell 78:773-785 (1994)). Some embodiments include methods of affecting the level of expression of IL-2, MHC-I, IL-6, TNFα, IFN-β, or any of the other previously-mentioned proteins, each method including administering to a subject a therapeutically effective amount of a liposomal composition comprising a peptide epoxyketone compound as disclosed herein. Complexes including p50 are rapid mediators of acute inflammatory and immune responses (Thanos, D. and Maniatis, T., Cell 80:529-532 (1995)).

NF-κB also participates in the expression of the cell adhesion genes that encode E-selectin, P-selectin, ICAM, and VCAM-1 (Collins, T., Lab. Invest. 68:499-508 (1993)). In some embodiments, a method for inhibiting cell adhesion (e.g., cell adhesion mediated by E-selectin, P-selectin, ICAM, or VCAM-1) is provided, including contacting a cell with (or administering to a subject) an effective amount of a liposomal composition comprising a peptide expoxyketone compound disclosed herein.

Certain embodiments of the present invention relate to a method for treating hyperproliferative conditions such as diabetic retinopathy, macular degeneration, diabetic nephropathy, glomerulosclerosis, IgA nephropathy, cirrhosis, biliary atresia, congestive heart failure, scleroderma, radiation-induced fibrosis, and lung fibrosis (idiopathic pulmonary fibrosis, collagen vascular disease, sarcoidosis, interstitial lung diseases, and extrinsic lung disorders). The treatment of burn victims often is hampered by fibrosis; thus, an additional embodiment of the invention is the topical or systemic administration of the peptide epoxyketone-containing liposomal composition for burn treatment. Wound closure following surgery often is associated with disfiguring scars, which can be prevented by inhibition of fibrosis. Thus, in certain embodiments, the invention relates to a method for prevention or reduction of scarring.

Ischemia and reperfusion injury results in hypoxia, a condition in which there is a deficiency of oxygen reaching the tissues of the body. This condition causes increased degradation of Iκ-Bα, thereby resulting in the activation of NF-κB. It has been demonstrated that the severity of injury resulting in hypoxia can be reduced with the administration of a proteasome inhibitor. Thus, provided herein is a method of treating an ischemic condition or reperfusion injury comprising administering to a subject in need of such treatment a therapeutically effective amount of a liposomal composition comprising a peptide epoxyketone compound as disclosed herein.

Certain embodiments of the present invention relate to a method of treating ischemia and reperfusion injury, which are associated with hypoxia, a deficiency of oxygen reaching the tissues of the body. Examples of such injuries or conditions include, but are not limited to, acute coronary syndrome (vulnerable plaques), arterial occlusive disease (cardiac, cerebral, peripheral arterial and vascular occlusions), atherosclerosis (coronary sclerosis, coronary artery disease), infarctions, heart failure, pancreatitis, myocardial hypertrophy, stenosis, and restenosis.

NF-κB also binds specifically to the HIV-enhancer/promoter. When compared to the Nef of mac239, the HIV regulatory protein Nef of pbj14 differs by two amino acids in the region which controls protein kinase binding. It is believed that the protein kinase signals the phosphorylation of IκB, triggering IκB degradation through the ubiquitin-proteasome pathway. After degradation, NF-κB is released into the nucleus, thus enhancing the transcription of HIV (Cohen, J., Science, 267:960 (1995)). Provided herein is a method for inhibiting or reducing HIV infection in a subject, and a method for decreasing the level of viral gene expression, each method including administering to the subject a therapeutically effective amount of a liposomal composition comprising a peptide epoxyketone compound as disclosed herein.

Two further embodiments of the present invention are a method for inhibiting or reducing HIV infection in a subject, and a method for decreasing the level of viral gene expression.

Viral infections contribute to the pathology of many diseases. Heart conditions such as ongoing myocarditis and dilated cardiomyopathy have been linked to the coxsackievirus B3. In a comparative whole-genome microarray analyses of infected mouse hearts, specific proteasome subunits were uniformly up-regulated in hearts of mice that developed chronic myocarditis (Szalay, et al., Am J Pathol 168:1542-52 (2006)). Some viruses utilize the ubiquitin-proteasome system in the viral entry step where the virus is released from the endosome into the cytosol. The mouse hepatitis virus (MHV) belongs to the Coronaviridae family, which also includes the severe acute respiratory syndrome (SARS) coronvirus. Yu and Lai (J Virol 79:644-648 (2005)) demonstrated that treatment of cells infected with MHV with a proteasome inhibitor resulted in a decrease in viral replication, correlating with reduced viral titer as compared to that of untreated cells. The human hepatitis B virus (HBV), a member of the Hepadnaviridae virus family, likewise requires virally encoded envelop proteins to propagate. Inhibiting the proteasome degradation pathway causes a significant reduction in the amount of secreted envelope proteins (Simsek, et al., J Virol 79:12914-12920 (2005)). In addition to HBV, other hepatitis viruses (A, C, D and E) may also utilize the ubiquitin-proteasome degradation pathway for secretion, morphogenesis and pathogenesis. Accordingly, in certain embodiments, a method for treating viral infection, such as SARS or hepatitis A, B, C, D and E, is provided comprising contacting a cell with (or administering to a subject) an effective amount of a liposomal composition comprising a peptide epoxyketone compound as disclosed herein.

Overproduction of lipopolysaccharide (LPS)-induced cytokines such as TNFα is considered to be central to the processes associated with septic shock. Furthermore, it is generally accepted that the first step in the activation of cells by LPS is the binding of LPS to specific membrane receptors. The α- and β-subunits of the 20S proteasome complex have been identified as LPS-binding proteins, suggesting that the LPS-induced signal transduction may be an important therapeutic target in the treatment or prevention of sepsis (Qureshi, N., et al., *J. Immun.* 171: 1515-1525 (2003)).

In certain embodiments, compounds of the present invention can be used for the inhibition of TNFα to prevent and/or treat septic shock.

Intracellular proteolysis generates small peptides for presentation to T-lymphocytes to induce MHC class I-mediated immune responses. The immune system screens for autologous cells that are virally infected or have undergone oncogenic transformation. One embodiment is a method for inhibiting antigen presentation in a cell, including exposing the cell to a liposomal composition comprising a peptide epoxyketone compound as described herein. A further embodiment is a method for suppressing the immune system of a subject (e.g., inhibiting transplant rejection, allergy, asthma), including administering to the subject a therapeutically effective amount of a liposomal composition comprising a peptide epoxyketone compound as described herein. Liposomal compositions provided herein can also be used to treat autoimmune diseases such as lupus, rheumatoid arthritis, multiple sclerosis, and inflammatory bowel diseases such as ulcerative colitis and Crohn's disease.

Another embodiment is a method for altering the repertoire of antigenic peptides produced by the proteasome or other Ntn with multicatalytic activity. For example, if the PGPH activity of 20S proteasome is selectively inhibited, a different set of antigenic peptides will be produced by the proteasome and presented in MHC molecules on the surfaces of cells than would be produced and presented either without any enzyme inhibition, or with, for example, selective inhibition of chymotrypsin-like activity of the proteasome.

An additional embodiment of the present invention is a method for inhibiting antigen presentation in a cell. In such method, the liposomal composition is used to treat immune-related conditions such as allergy, asthma, organ/tissue rejection (graft-versus-host disease), and auto-immune diseases, including, but not limited to, lupus, rheumatoid arthritis, psoriasis, multiple sclerosis, and inflammatory bowel diseases (such as ulcerative colitis and Crohn's disease). Thus, a further embodiment is a method for suppressing the immune system of a subject (e.g., inhibiting transplant rejection, allergies, auto-immune diseases, and asthma), including administering to the subject an effective amount of a liposomal composition comprising a peptide epoxyketone compound described herein.

Certain proteasome inhibitors block both degradation and processing of ubiquitinated NF-κB in vitro and in vivo. Proteasome inhibitors also block IκB-α degradation and NF-κB activation (Palombella, et al. *Cell* 78:773-785 (1994); and Traenckner, et al., *EMBO J.* 13:5433-5441 (1994)). In some embodiments, a method for inhibiting IκB-α degradation is provided, including contacting the cell with a liposomal composition comprising a peptide epoxyketone compound as described herein. A further embodiment is a method for reducing the cellular content of NF-κB in a cell, muscle, organ, or subject, including contacting the cell, muscle, organ, or subject with a liposomal composition comprising a peptide epoxyketone compound as described herein.

Other eukaryotic transcription factors that require proteolytic processing include the general transcription factor TFIIA, herpes simplex virus VP16 accessory protein (host cell factor), virus-inducible IFN regulatory factor 2 protein, and the membrane-bound sterol regulatory element-binding protein 1.

Further provided herein are methods for affecting cyclin-dependent eukaryotic cell cycles, including exposing a cell (in vitro or in vivo) to a liposomal composition comprising a peptide epoxyketone compound disclosed herein. Cyclins are proteins involved in cell cycle control. The proteasome participates in the degradation of cyclins. Examples of cyclins include mitotic cyclins, G1 cyclins, and cyclin B. Degradation of cyclins enables a cell to exit one cell cycle stage (e.g., mitosis) and enter another (e.g., division). It is believed all cyclins are associated with p34cdc2 protein kinase or related kinases. The proteolysis targeting signal is localized to amino acids 42-RAALGNISEN-50 (destruction box). There is evidence that cyclin is converted to a form vulnerable to a ubiquitin ligase or that a cyclin-specific ligase is activated during mitosis (Ciechanover, A., *Cell*, 79:13-21 (1994)). Inhibition of the proteasome inhibits cyclin degradation, and therefore inhibits cell proliferation, for example, in cyclin-related cancers (Kumatori, et al., *Proc. Natl. Acad. Sci. USA* 87:7071-7075 (1990)). Provided herein is a method for treating a proliferative disease in a subject (e.g., cancer, psoriasis, or restenosis), including administering to the subject a therapeutically effective amount of a composition disclosed herein. Also provided herein is a method for treating cyclin-related inflammation in a subject, including administering to a subject a therapeutically effective amount of a liposomal composition comprising a peptide epoxyketone compound as described herein.

Additional embodiments include methods for affecting the proteasome-dependent regulation of oncoproteins and methods of treating or inhibiting cancer growth, each method including exposing a cell (in vivo, e.g., in a subject, or in vitro) to a liposomal composition comprising a peptide epoxyketone compound as disclosed herein. HPV-16 and HPV-18-derived E6 proteins stimulate ATP- and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. One embodiment is a method for treating p53-related apoptosis, including administering to a subject a therapeutically effective amount of a liposomal composition comprising a peptide epoxyketone compound as disclosed herein.

One embodiment of the invention is a method for inhibiting IκB-α degradation, including contacting the cell with the liposomal composition. A further embodiment is a method for reducing the cellular content of NF-κB in a cell, muscle, organ, or subject, including contacting the cell, muscle, organ, or subject with a liposomal composition comprising a peptide epoxyketone compound.

A further embodiment of the invention is a method for treating a proliferative disease in a subject (e.g., cancer, psoriasis, or restenosis), including administering to the subject an effective amount of the liposomal composition. The invention also encompasses a method for treating cyclin-related inflammation in a subject.

Another embodiment of the present invention is a method for treating p53-related apoptosis.

The proteasome of these parasites is considered to be involved primarily in cell differentiation and replication activities (Paugam, et al., *Trends Parasitol.* 19(2): 55-59 (2003)). Furthermore, entamoeba species have been shown to lose encystation capacity when exposed to proteasome inhibitors (Gonzales, et al., *Arch. Med. Res.* 28, Spec No: 139-140 (1997)). Other compounds useful as proteasome inhibitors in the treatment of parasitic diseases are described in WO 98/10779.

In certain embodiments, the disclosed compositions inhibit proteasome activity irreversibly in a parasite. Such irreversible inhibition has been shown to induce shutdown in enzyme activity without recovery in red blood cells and white blood cells. In certain such embodiments, the long half-life of blood cells may provide prolonged protection with regard to therapy against recurring exposures to parasites. In certain embodiments, the long half-life of blood cells may provide prolonged protection with regard to chemoprophylaxis against future infection.

In a certain embodiments, the invention's liposomal compositions are useful for the treatment of a parasitic infection, such as infections in humans caused by a protozoan parasite selected from *Plasmodium* sps. (including *P. falciparum, P. vivax, P. malariae*, and *P. ovale*, which cause malaria), *Trypanosoma* sps. (including *T. cruzi*, which causes Chagas' disease, and *T. brucei* which causes African sleeping sickness), *Leishmania* sps. (including *L. amazonensis, L. donovani, L. infantum, L. mexicana*, etc.), *Pneumocystis carinii* (a protozoan known to cause pneumonia in AIDS and other immunosuppressed patients), *Toxoplasma gondii, Entamoeba histolytica, Entamoeba invadens*, and *Giardia lamblia*. In certain embodiments, the disclosed liposomal compositions comprising peptide epoxyketone compounds are useful for the treatment of parasitic infections in animals and livestock caused by a protozoan parasite selected from *Plasmodium hermani, Cryptosporidium* sps., *Echinococcus granulosus, Eimeria tenella, Sarcocystis neurona*, and *Neurospora crassa*.

Prokaryotes have what is equivalent to the eukaryote 20S proteasome particle. Albeit, the subunit composition of the prokaryote 20S particle is simpler than that of eukaryotes, it has the ability to hydrolyze peptide bonds in a similar manner. For example, the nucleophilic attack on the peptide bond occurs through the threonine residue on the N-terminus of the β-subunits. In some embodiments, a method of treating prokaryotic infections is provided, comprising administering to a subject a therapeutically effective amount of a liposomal composition comprising a peptide epoxyketone compound as disclosed herein. Prokaryotic infections may include diseases caused by either mycobacteria (such as tuberculosis, leprosy or Buruli Ulcer) or archaebacteria.

It has also been demonstrated that inhibitors that bind to the 20S proteasome stimulate bone formation in bone organ cultures. Furthermore, when such inhibitors have been administered systemically to mice, certain proteasome inhibitors increased bone volume and bone formation rates over 70% (Garrett, I. R., et al., *J. Clin. Invest.* 111: 1771-1782 (2003)), therefore suggesting that the ubiquitin-proteasome machinery regulates osteoblast differentiation and bone formation. Therefore, the disclosed liposomal compositions comprising peptide epoxyketone compounds may be useful in the treatment and/or prevention of diseases associated with bone loss, such as osteoporosis.

Provided herein is a method for treating a disease or condition selected from cancer, autoimmune disease, graft or transplant-related condition, neurodegenerative disease, fibrotic-associated condition, ischemic-related conditions, infection (viral, parasitic or prokaryotic) and diseases associated with bone loss, comprising administering a therapeutically effective amount of a liposomal composition comprising a peptide epoxyketone compound as provided herein.

Bone tissue is an excellent source for factors which have the capacity for stimulating bone cells. Thus, extracts of bovine bone tissue contain not only structural proteins that are responsible for maintaining the structural integrity of bone, but also biologically active bone growth factors that can stimulate bone cells to proliferate. Among these latter factors is a recently described family of proteins called bone morphogenetic proteins (BMPs). All of these growth factors have effects on other types of cells, as well as on bone cells (see e.g., Hardy, M. H., et al., *Trans Genet* 8:55-61 (1992), which describes evidence that bone morphogenetic proteins (BMPs) are differentially expressed in hair follicles during development; BMP-2 expression in mature follicles also occurs during maturation and after the period of cell proliferation (Hardy, M. H., et al., (1992, supra); Harris, S. E., et al., *J Bone Miner Res* 9:855-863 (1994), which describes the effects of TGF-β on expression of BMP-2 and other substances in bone cells). Thus, liposomal compositions comprising peptide epoxyketone compounds as provided herein may also be useful for hair follicle growth stimulation.

In one embodiment of the present invention, the liposomal compositions can be useful in the treatment and/or prevention of diseases associated with bone loss, such as osteoporosis.

Finally, the disclosed liposomal compositions comprising peptide epoxyketone compounds are also useful as diagnostic agents (e.g., in diagnostic kits or for use in clinical laboratories) for screening for proteins (e.g., enzymes, transcription factors) processed by Ntn hydrolases, including the proteasome. The disclosed liposomal compositions are also useful as research reagents for specifically binding the X/MB1 subunit or α-chain and inhibiting the proteolytic activities associated with it. For example, the activity of (and specific inhibitors of) other subunits of the proteasome can be determined.

Actual dosage levels of peptide epoxyketone compounds in pharmaceutical compositions of this invention can be varied so as to obtain an amount of the peptide epoxyketone compound that is effective to achieve the desired therapeutic response for a particular subject, composition, and mode of administration, without being toxic to the subject.

The concentration of peptide epoxyketone compound in a pharmaceutically acceptable mixture will vary depending on several factors, including dosage of the compound to be administered, pharmacokinetic characteristics of the compound(s) employed, and route of administration. In general, the liposomal compositions of this invention can be provided in an aqueous solution for parenteral administration. Typical dose ranges are from about 0.01 mg/kg to about 50 mg/kg of body weight per day of peptide epoxyketone compound. Exemplary dose ranges include between about 10 mg/m$^2$ and about 150 mg/m$^2$ (mg/m$^2$, milligrams per square meter of body surface of the subject to whom the liposomal composition is administered) of peptide epoxyketone compound, preferably between about 15 mg/m$^2$ and about 70 mg/m$^2$, more preferably between about 15 mg/m$^2$ and about 56 mg/m$^2$. Administration of the liposomal compositions of the present invention is typically intravenously, once or twice weekly, and can be administered in single or divided doses. Each divided dose may contain the same or different peptide epoxyketone compounds. The dosage will be an effective amount depending on several factors including the overall health of a patient, and the composition and route of administration of the selected peptide epoxyketone compound(s). Dosage forms (also called unit doses) of liposomal compositions of the present invention are typically single-use vials comprising between about 20 mg and about 300 mg of peptide epoxyketone compound, preferably between about 30 mg and about 140 mg, more preferably between about 30 mg and about 112 mg.

Another aspect of the present invention provides a combination treatment wherein one or more other therapeutic agents are administered with the peptide epoxyketone-containing liposomal composition. Such combination treatment can be achieved by simultaneous, sequential, or separate dosing of the individual components of the treatment.

In certain embodiments of the present invention, a peptide epoxyketone-containing liposomal composition described herein is used as part of a combination treatment that includes one or more other proteasome inhibitor(s).

In other embodiments, a liposomal composition of the invention is part of a combination treatment that includes a chemotherapeutic. Suitable chemotherapeutics may include natural products such as vinca alkaloids (i.e., vinblastine, vincristine, and vinorelbine), paclitaxel, epidipodophyllotoxins (i.e., etoposide, teniposide), antibiotics (dactinomycin (actinomycin D), daunorubicin, doxorubicin, and idarubicin), anthracyclines, mitoxantrone, bleomycins, plicamycin (mithramycin), and mitomycin, enzymes (L-asparaginase, which systemically metabolizes L-asparagine and deprives cells that do not have the capacity to synthesize their own asparagine); antiplatelet agents; antiproliferative/antimitotic alkylating agents such as nitrogen mustards (mechlorethamine, cyclophosphamide, and analogs, melphalan, chlorambucil), ethylenimines and methylmelamines (hexamethylmelamine and thiotepa), alkyl sulfonates (busulfan), nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin, and 2-chlorodeoxyadenosine); aromatase inhibitors (anastrozole, exemestane, and letrozole); and platinum coordination complexes (cisplatin, carboplatin), procarbazine, hydroxyurea, mitotane, aminoglutethimide; histone deacetylase (HDAC) inhibitors (trichostatin, sodium butyrate, apicidan, suberoyl anilide hydroamic acid); hormones (i.e., estrogen) and hormone agonists such as leutinizing hormone releasing hormone (LHRH) agonists (goserelin, leuprolide, and triptorelin). Other chemotherapeutic agents may include lenalidomide, mechlorethamine, camptothecin, ifosfamide, tamoxifen, raloxifene, gemcitabine, navelbine, or any analog or derivative variant of the foregoing.

In certain embodiments, a liposomal composition comprising a peptide epoxyketone compound as described herein is conjointly administered with one or more histone deacetylase (HDAC) inhibitors (e.g., trichostatin, sodium butyrate, apicidan, suberoyl anilide hydroamic acid ("SAHA" (Vorinostat)), trichostatin A, depsipeptide, apicidin, A-161906, scriptaid, PXD-101, CHAP, butyric acid, depudecin, oxamflatin, phenylbutyrate, valproic acid, MS275 (N-(2-Aminophenyl)-4-[N-(pyridine-3-ylmethoxycarbonyl)aminomethyl]benzamide), LAQ824/LBH589, CI994, MGCD0103, ACY-1215, Panobinostat; e.g., SAHA, ACY-1215, Panobinostat).

In certain embodiments, liposomal compositions comprising peptide epoxyketone compounds as described herein are conjointly administered with one or more DNA binding/Cytotoxic agents (e.g., Zalypsis).

In certain embodiments, a liposomal composition comprising a peptide epoxyketone compound as described herein is conjointly administered with one or more taxanes (e.g., docetaxel, and/or paclitaxel).

In certain embodiments, liposomal compositions comprising peptide epoxyketone compounds as described herein are conjointly administered with dexamethasone. For example, treatment may include pre-medicating with dexamethasone 4 mg orally or intravenously prior to all doses of liposomal compositions comprising peptide epoxyketone compounds during a first treatment cycle and prior to all doses of liposomal compositions comprising peptide epoxyketone compounds during a treatment cycle with dose escalation to reduce the incidence and severity of infusion reactions. Such dexamethasone premedication (e.g., 4 mg orally or intravenously) is administered if such reactions develop or reappear during subsequent treatment cycles.

In some embodiments, the present invention relates to a method of treating cancer (e.g., multiple myeloma or solid tumor) in a subject in need of treatment. The method typically comprises administering a therapeutically effective amount of a pharmaceutical liposomal composition of the present invention (e.g., comprising carfilzomib), and may further comprise simultaneous, sequential, or separate administration of a therapeutically effective amount of a chemotherapeutic agent.

In certain embodiments of the present invention, a liposomal composition described herein is used in a combination treatment that includes a cytokine. Cytokines include, but are not limited to, Interferon-γ, Interferon-α, and Interferon-β; Interleukins 1-8, 10, and 12; Granulocyte Monocyte Colony-Stimulating Factor (GM-CSF); TNF-α and TNF-β; and TGF-β.

Embodiments of the present invention include combination treatments incorporating a liposomal composition described herein and a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof.

In certain embodiments of the present invention, a liposomal composition described herein is part of a combination treatment that includes an immunotherapeutic agent. Suitable immunotherapeutic agents may include, but are not limited to, MDR modulators (verapamil, valspordar, biricodar, tariquidar, laniquidar), cyclosporine, thalidomide, and monoclonal antibodies). The monoclonal antibodies can be either naked or conjugated such as rituximab, tositumomab, alemtuzumab, epratuzumab, ibritumomab tiuxetan, gemtuzumab ozogamicin, bevacizumab, cetuximab, erlotinib, and trastuzumab. In certain embodiments, a liposomal composition of the present disclosure described herein is conjointly administered with lenalidomide (REVLIMID®, Celgene Corporation, Summit, N.J.).

In some embodiments, a liposomal composition comprising a peptide epoxyketone compound as described herein is conjointly administered with one or more topoisomerase inhibitors (e.g., irinotecan, topotecan, camptothecin, lamellarin D, etoposide).

In some embodiments, a liposomal composition comprising a peptide epoxyketone compound as described herein is conjointly administered with one or more m-TOR inhibitors (e.g., CCI-779, AP23573 and RAD-001).

In some embodiments, a liposomal composition comprising a peptide epoxyketone compound as described herein is conjointly administered with one or more protein kinase inhibitor (e.g., sorafenib, imatinib, dasatinib, sunitinib, pazopanib, and nilotinib; e.g., sorafenib).

In some embodiments, a liposomal composition comprising a peptide epoxyketone compound as described herein is conjointly administered with one or more CDK Inhibitors (e.g., Dinaciclib).

In some embodiments, a liposomal composition comprising a peptide epoxyketone compound as described herein is conjointly administered with one or more KSP(Eg5) Inhibitors (e.g., Array 520).

In some embodiments, a liposomal composition comprising a peptide epoxyketone compound as described herein is conjointly administered with one or more PI13 delta Inhibitors (e.g., GS-1101 PI3K).

In some embodiments, a liposomal composition comprising a peptide epoxyketone compound as described herein is conjointly administered with one or more Dual Inhibitor: PI3K delta and gamma Inhibitors (e.g., CAL-130).

In some embodiments, a liposomal composition comprising a peptide epoxyketone compound as described herein is conjointly administered with one or more multi-kinase Inhibitors (e.g., TG02).

In some embodiments, a liposomal composition comprising a peptide epoxyketone compound as described herein is conjointly administered with one or more PI3K delta Inhibitors (e.g., TGR-1202).

In some embodiments, a liposomal composition comprising a peptide epoxyketone compound as described herein is conjointly administered with:

(i) one or more of the following:
one or more second chemotherapeutic agents (e.g., one or more HDAC inhibitors (e.g., SAHA, ACY-1215, Panobinostat); one or more nitrogen mustards (e.g., melphalan); one or more DNA binding/cytotoxic agents (e.g., Zylapsis); one or more taxanes (e.g., docetaxel); one or more antibiotics (e.g., dactinomycin (actinomycin D), daunorubicin, doxorubicin and idarubicin; e.g., doxorubicin);

one or more other peptide epoxyketone compound (e.g., another compound of formulae (I)-(V));
one or more cytokines;
one or more immunotherapeutic agents (e.g., REVLIMID®);
one or more topoisomerase inhibitors;
one or more m-TOR inhibitors;
one or more protein kinase inhibitor (e.g., sorafenib);
one or more CDK Inhibitors (e.g., Dinaciclib);
one or more KSP(Eg5) Inhibitors (e.g., Array 520);
one or more PI13 delta Inhibitors (e.g., GS-1101 PI3K);
one or more Dual Inhibitor: PI3K delta and gamma Inhibitors (e.g., CAL-130);
one or more multi-kinase Inhibitors (e.g., TG02);
one or more PI3K delta Inhibitors (e.g., TGR-1202); and (ii) one or more steroids (e.g., dexamethasone).

In certain embodiments, a liposomal composition comprising a peptide epoxyketone compound as described herein is conjointly administered with:

(i) one of the following:
one or more second chemotherapeutic agents (e.g., one or more HDAC inhibitors, (e.g., SAHA, ACY-1215, Panobinostat); one or more nitrogen mustards (e.g., melphalan); one or more DNA binding/cytotoxic agents, (e.g., Zylapsis); one or more taxanes (e.g., docetaxel); one or more antibiotics (e.g., dactinomycin (actinomycin D), daunorubicin, doxorubicin and idarubicin; e.g., doxorubicin);

one or more other peptide epoxyketone compound (e.g., another compound of formulae (I)-(V));
one or more cytokines;
one or more immunotherapeutic agents (e.g., REVLIMID®);
one or more topoisomerase inhibitors;
one or more m-TOR inhibitors;
one or more protein kinase inhibitor (e.g., sorafenib);
one or more CDK Inhibitors (e.g., Dinaciclib);
one or more KSP(Eg5) Inhibitors (e.g., Array 520);
one or more PI13 delta Inhibitors (e.g., GS-1101 PI3K);
one or more Dual Inhibitor: PI3K delta and gamma Inhibitors (e.g., CAL-130);
one or more multi-kinase Inhibitors (e.g., TG02);
one or more PI3K delta Inhibitors (e.g., TGR-1202); and (ii) dexamethasone.

Experiments performed in support of the present invention demonstrated that liposomal compositions of the present invention provided increased maximum tolerated dose (MTD) relative to a non-liposomal composition comprising peptide epoxyketone compound. For example, in mice, a first liposomal composition resulted in a 2.5-fold increase in the MTD, and a second liposomal composition resulted in a 50% increase. In rats, both liposomal compositions resulted in increases in tolerability (Example 4). Biodistribution, as measured by proteasome inhibition in blood and tissues, was similar across the various compositions (Example 5, FIG. 2A-2D; Example 8, FIG. 3A-3D; Example 11, FIG. 5A-5D). Further, the liposomal peptide epoxyketone compound compositions of the present invention provided about 3 to 5 and 7-fold increased exposure (AUC) in mice and rats, respectively, compared to a non-liposomal composition comprising peptide epoxyketone compound. This increased exposure was the result of a decrease in plasma clearance (Example 6).

Further, liposomal compositions comprising a peptide epoxyketone compound entrapped in the liposomes' aqueous core demonstrated enhanced tolerability by increasing the maximum tolerated dose (MTD) of carfilzomib in mice by 50%, from 10 mg/kg to 15 mg/kg as compared to the injectable, non-liposomal, SBE-B-CD composition. These results indicate that liposomal compositions comprising a peptide epoxyketone compound entrapped in the liposomes' aqueous core release carfilzomib over a longer period of time with a lower maximum plasma concentration (Cmax) relative to the injectable, non-liposomal, SBE-B-CD composition.

The liposomal compositions comprising liposomes having a peptide epoxyketone compound entrapped in their aqueous core also resulted in delayed proteasome recovery at 24 hours in some mouse tissues whereas the current drug product (i.e., injectable, non-liposomal, CFZ SBE-B-CD) resulted in recovery from proteasome inhibition by 24 hours post-dose (Example 8, FIG. 3A, FIG. 3B, FIG. 3C, FIG. 3D). These results support that the liposomal compositions provide long-term exposure of peptide epoxyketone compounds.

Figure 6:
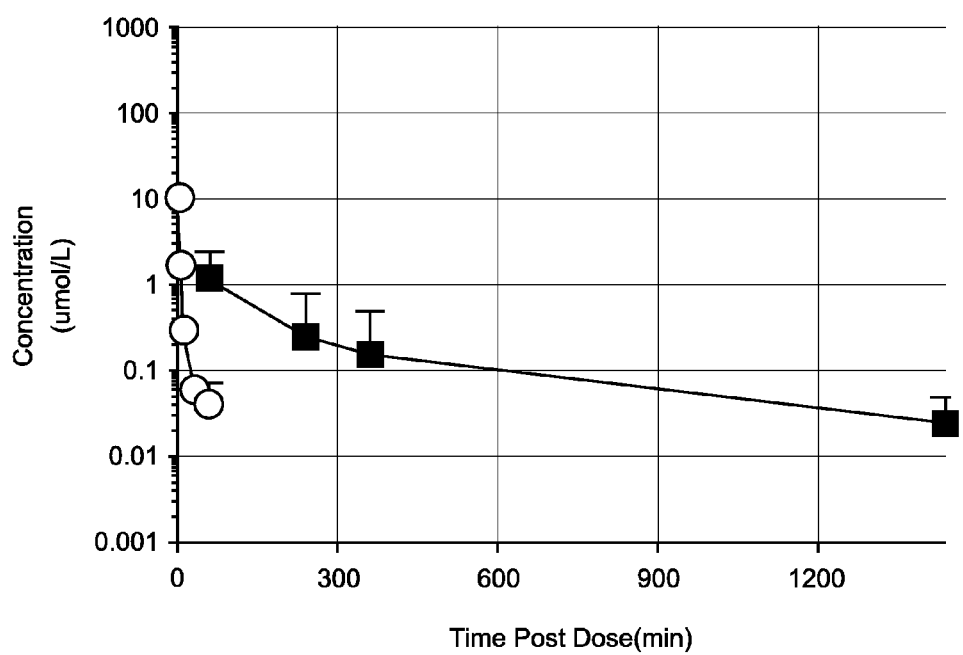
FIG. 6 presents data related to the circulation half-life in BALB/C mice of different compositions of carfilzomib. In the figure, the vertical axis is the concentration of carfilzomib in umol/L (Concentration (umol/L)), and the horizontal axis is the time post dose in minutes (Time Post Dose (min)). The line with open circles corresponds to administration of 5 mg/kg of an injectable carfilzomib SBE-B-CD composition (non-liposomal). The line with solid squares corresponds to administration of 15 mg/kg of a liposomal composition of carfilzomib comprising liposomes comprising entrapped carfilzomib (pL-6). Error bars are represented unidirectionally.

When delivered in the non-liposomal CFZ SBE-B-CD composition, the plasma concentration of carfilzomib declined rapidly and was not detectable after 1 hour post-dose (Example 11, FIG. 6). When carfilzomib was delivered as liposomal compositions comprising a peptide epoxyketone compound entrapped in the liposomes, systemic exposure was extended with detectable total drug (both encapsulated and released) for up to 24 hours post-dose (Example 11, FIG. 6). These data demonstrate that the liposomal compositions comprising a peptide epoxyketone compound entrapped in the liposomes resulted in greater exposure and longer circulation relative to a non-liposomal, peptide epoxyketone compound composition.

Figure 4:
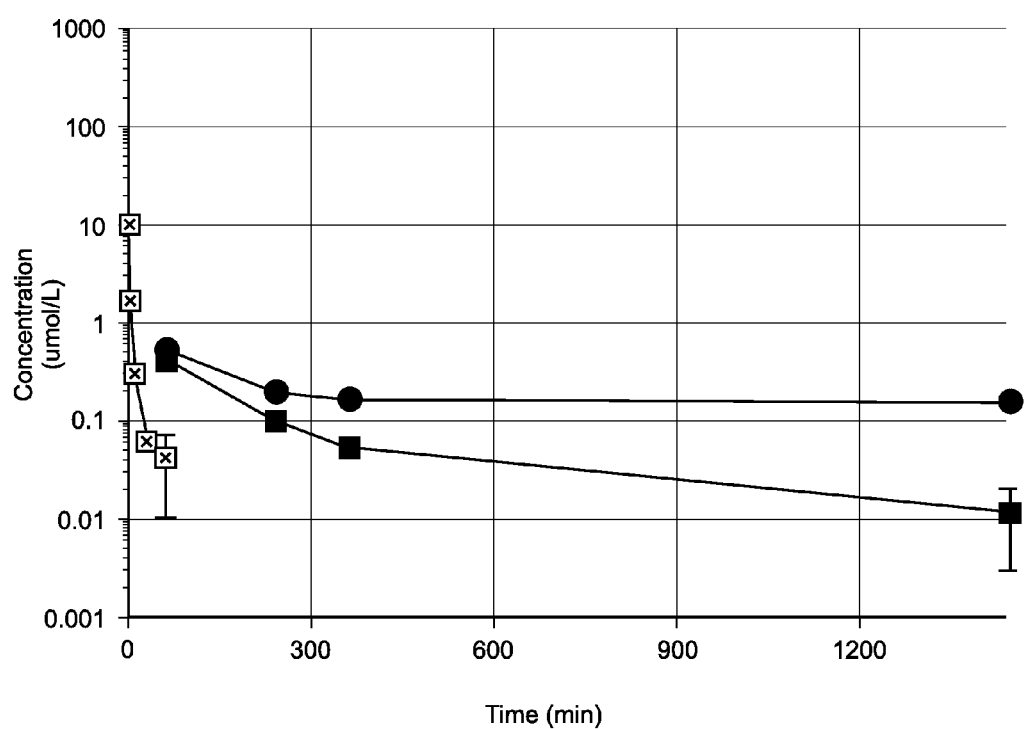
FIG. 4 presents data related to the circulation half-life in BALB/C mice of different compositions of carfilzomib. In the figure, the vertical axis is the concentration of carfilzomib in umol/L (Concentration (umol/L)), and the horizontal axis is the time in minutes (Time (min)). The line with open squares containing an X corresponds to administration of 5 mg/kg of an injectable carfilzomib SBE-B-CD composition (non-liposomal). The line with solid squares corresponds to administration of 5 mg/kg of apL11, a pegylated liposomal composition of carfilzomib wherein the aqueous core of the pegylated liposomes comprises carfilzomib and SBE-B-CD. The line with solid circles corresponds to administration of 15 mg/kg of apL11, a pegylated liposomal composition of carfilzomib wherein the aqueous core of the pegylated liposomes comprises carfilzomib and SBE-B-CD. Error bars are represented bidirectionally.

In addition, when delivered in the non-liposomal CFZ SBE-B-CD composition, the plasma concentration of carfilzomib declined rapidly and was not detectable after 1 hour post-dose (Example 9, FIG. 4). When carfilzomib was delivered as liposomal compositions comprising a peptide epoxyketone compound entrapped in the liposomes' aqueous core, systemic exposure was extended with detectable total drug (both encapsulated and released) for up to 24 hours post-dose (Example 9, FIG. 4). These data demonstrate that the liposomal compositions comprising a peptide epoxyketone compound entrapped in the liposomes' aqueous core resulted in significantly greater exposure and longer circulation relative to an injectable, non-liposomal, peptide epoxyketone compound composition.

Figure 7:
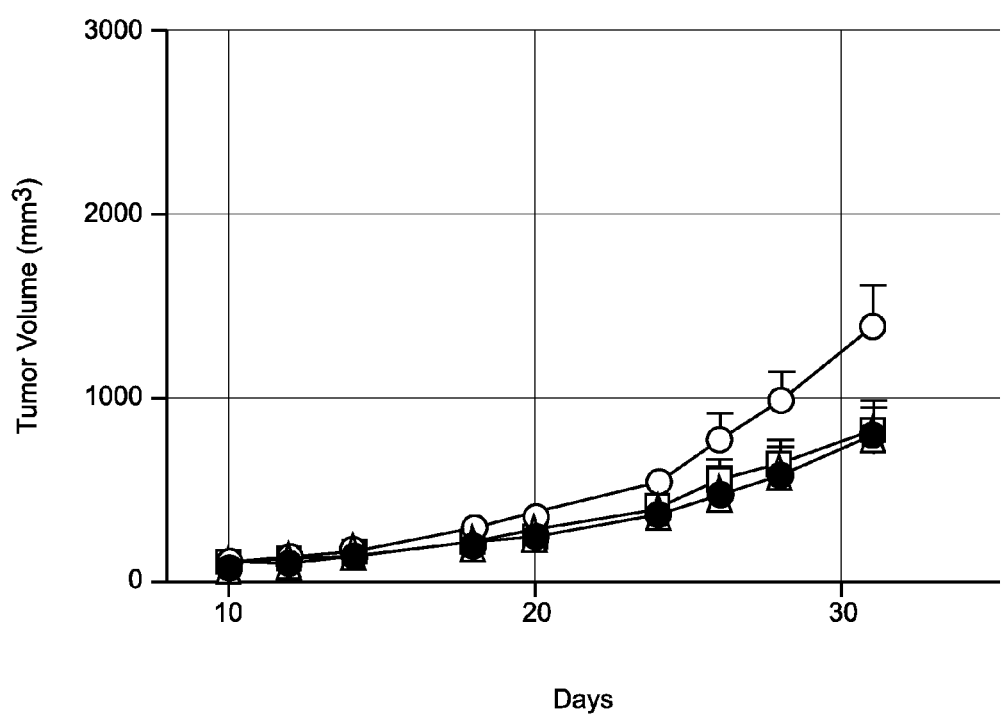
FIG. 7 presents data related to the dosing frequency of different compositions of carfilzomib in a mouse xenograft tumor model. In the figure, the vertical axis is tumor volume in $mm^3$ (Tumor Volume ($mm^3$)), and the horizontal axis is days post-tumor challenge (Days). The line (top line in the figure at 30 days) with open circles correspond to once-weekly administration of vehicle (liposomes comprising 12.5 mg/mL EPC, 3.1 mg/mL Cholesterol, 1.2 mg/mL mPEG-DSPE, with no carfilzomib); the line with open squares corresponds to 5 mg/kg of a non-liposomal carfilzomib SBE-B-CD composition (non-liposomal) administered on days 1 and 2 of each week; the line with solid circles corresponds to administration of pL-6=2 mg/mL CFZ, 12.5 mg/mL Sphingomylin, 3.2 mg/mL cholesterol, 1.3 mg/mL mPEG-DSPE providing a dose of 10 mg/kg of carfilzomib administered on days 1 and 2 of each week. The line with open triangles corresponds to administration of pL-6=2 mg/mL CFZ, 12.5 mg/mL Sphingomylin, 3.2 mg/mL cholesterol, 1.3 mg/mL mPEG-DSPE providing a dose of 15 mg/kg of carfilzomib administered once weekly. This figure presents data up to day 31. Error bars are represented unidirectionally.
Figure 8:
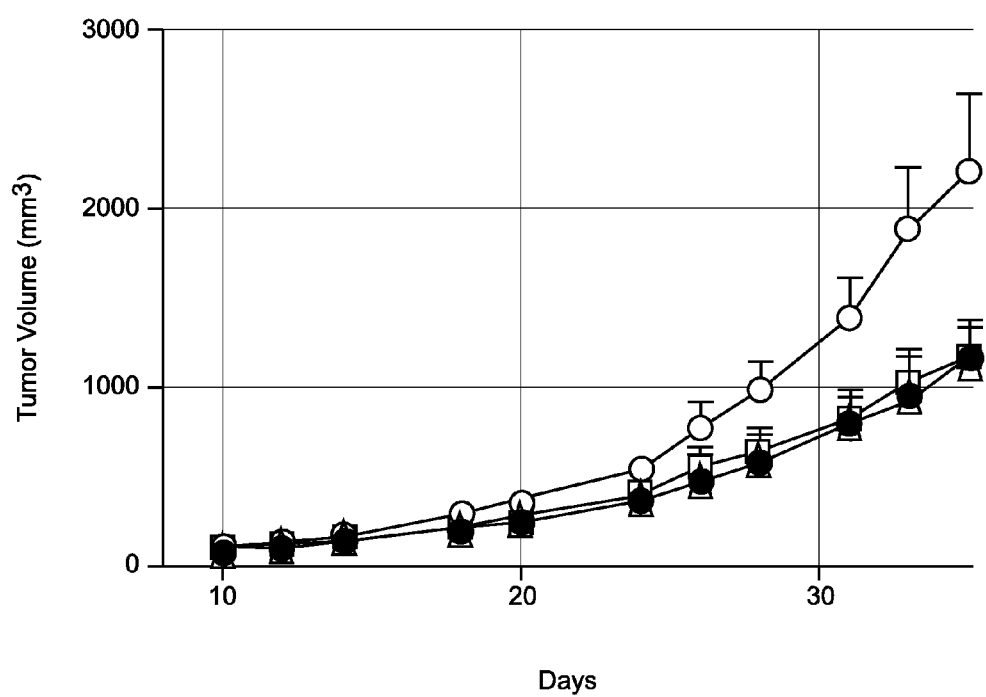
FIG. 8 corresponds to FIG. 7, with the exception that FIG. 8 presents data up to day 38 (i.e., two additional time points relative to FIG. 7). Error bars are represented unidirectionally.

Also, liposomal compositions of the present invention maintain anti-tumor efficacy as compared to a non-liposomal composition comprising the same peptide epoxyketone compound; further, liposomal compositions of the present invention maintain anti-tumor efficacy at a reduced dosing frequency as compared to a non-liposomal composition comprising the same peptide epoxyketone compound (Example 11, FIG. 7, FIG. 8; Example 12, FIG. 9, FIG. 10).

Example 13 sets forth exemplary criteria for screening and selection of advantageous liposomal compositions comprising peptide epoxyketone compounds. Liposomal compositions of the present invention and those produced by the methods of the present invention are screened based on, for example, pharmacokinetic data (e.g., plasma half-life and area under the plasma concentration time curve), pharmacodynamic profiles (e.g., biodistribution, maximum CT-L activity inhibition, and prolonged inhibition in tissues), and anti-tumor activity (e.g., as evaluated in human tumor xenograft rodent studies).

Accordingly, the data in the Examples demonstrate that liposomal compositions of the present invention resulted in prolonged exposure without affecting biodistribution. Tolerability of the peptide epoxyketone compound was also enhanced in animals, likely due to reduced exposure to high concentrations of free drug. The liposomal compositions comprising peptide epoxyketone compounds of the present invention provide the following improvements relative to the current non-liposomal CFZ SBE-B-CD composition: improved pharmacodynamic profiles of peptide epoxyketone compounds by delaying proteasome recovery; improved pharmacokinetic profiles by decreasing clearance and extending plasma half-life; improved safety profiles of peptide epoxyketone compounds (i.e. tolerability); and reduced dosing frequency.

Experimental

The following examples are put forth so as to provide those of ordinary skill in the art with a complete disclosure and description of how to practice the present invention, and are not intended to limit the scope of what the inventors regard as the invention. Efforts have been made to ensure accuracy with respect to numbers used (e.g., amounts, concentrations, percent changes, etc.) but some experimental errors and deviations should be accounted for. Unless indicated otherwise, temperature is in degrees Centigrade and pressure is at or near atmospheric.

The compositions used to practice the methods of the present invention meet the specifications for content and purity required of pharmaceutical products.

1.0 MATERIALS AND METHODS

Particle Size Reduction of Liposomal Suspension

Particle size reduction or deagglomeration of the rehydrated liposomal suspension can be carried out either by sonication (20 to 60 minutes) or by high-pressure homogenization/microfluidizer (up to 30,000 psi).

Content Determination by HPLC Assay

The liposomal suspension can be mixed with an organic solvent, for example, methanol, to dissolve lipids and free the carfilzomib. The solution can be filtered through a 0.2 µm PTFE filter prior to HPLC analysis.

Carfilzomib content can be determined by a gradient HPLC assay according to the method in Table 1 using sodium perchlorate buffer, 0.1M, pH 3.1 and acetonitrile (50:50 v/v).

TABLE 1

Column: Phenomenex Gemini ™ C18, 150 × 4.6 mm, 5 µm particle size
Column Temperature: 30 ± 2° C.
Autosampler Temperature: 5 ± 3° C.
Detection Wavelength: 220 nm
Flow Rate: 1.5 mL/min
Injection Volume: 10 µL
Total Run Time: 17 min Liposome Morphology The vesicle size, shape and surface morphology of the liposomal composition can be determined by scanning electron microscopy (SEM) and transmission electron microscopy (TEM).

Liposome/Carfilzomib Solid State

Polarized light microscopy, differential scanning calorimetry (DSC), X-ray diffraction (XRD), and freeze fracture electron microscopy can be used to elucidate the phase behavior of the vesicles.

Liposome Size and Distribution

Polarized light microscopy, dynamic light scattering, and TEM can be used to determine the size and size distribution range of the liposomes of the liposomal composition.

Determination of Free Drug

Because carfilzomib has extremely low aqueous solubility, the amount of entrapped drug versus free drug can be qualitatively determined based on polarized light microscope. Free drug precipitates in the aqueous medium, due to its extremely low aqueous solubility, and the precipitated material can be seen using a polarized light microscope.

Sulfobutyl Ether-β-Cyclodextrins

Sulfobutyl ether-β-cyclodextrins (SBE-B-CD), for example, CAPTISOL®, can be synthetically produced and/or are commercially available, for example from Ligand Pharmaceuticals, Inc., La Jolla, Calif.

2.0 EXAMPLES

Example 1

Preparation of Molecularly Dispersed Carfilzomib in Thin Lipid Film

To make liposomal carfilzomib, the following materials in the indicated ratios were added to a suitably sized round bottom flask: drug to total lipid weight ratio of 0.05:0.95 to 0.17:0.83. Total lipids typically comprise the lipids EPC, HSPC, DSPC, DSPG, POPC, DPPC, DSPE, and/or sphingomyelin (SPH) alone, or with cholesterol. If cholesterol is added, the phospholipid to cholesterol weight ratio (phospholipid:cholesterol) of from 0.9:0.1 to 0.5:0.5. An appropriate volume of phosphate buffer saline was used to rehydrate the lipid film to give a target carfilzomib concentration of 1 and 2 mg/mL, respectively.

To make PEGylated liposomal carfilzomib, the following materials in the indicated ratios were added to a suitably sized round bottom flask: drug to total lipid weight ratio of 0.11:0.89 to 0.16:0.84. Phospholipids typically comprise the lipids EPC, HSPC, DSPC, DPPC, DSPG, POPC, SPH, DSPE, or combinations thereof. When PEG-derivatized lipids are present (e.g., PEG-derivatized phospholipids) the typical weight ratio for total lipids (phospholipids:PEG-derivatized lipids) is from 0.9:0.1 to 0.75:0.25. Further, when cholesterol is also added the typical weight ratio for total lipids is (phospholipids:PEG-derivatized lipids:cholesterols) is from 0.833:0.0833:0.0833 to 0.57:0.14:0.29. An appropriate volume of phosphate buffer saline was used to rehydrate the lipid film to give a target carfilzomib concentration of 2 mg/mL.

To dissolve the lipids and carfilzomib, an appropriate volume of organic solvent (e.g., cloroform:MeOH (60:40 or 50:50 v/v)), enough to achieve between 10-20 mg/mL dissolved lipid, was added to the flask. The flask was attached to a rotary evaporator spinning at 50-100 rpm and immersed in a water bath set above the highest gel-liquid crystal phase transition (Tc) temperature of the lipids used. Although the Tc for egg phosphatidylcholine is below room temperature (−15° C. to −7° C.), the temperature bath used for EPC was approximately 45° C. to 50° C. For DSPC, DPPC, and mPEG-DSPE, the water bath temperature should be set greater than 55° C., 41° C., and 50° C., respectively.

The flask was allowed to rotate in the water bath for approximately 1 minute to equilibrate. A slow vacuum was pulled, to as low as <10 Torr, to obtain a thin dry film on the walls of the flask without precipitation. To remove any residual solvent, the flask was subjected to high vacuum at room temperature for a few hours or overnight. Table 2A presents nominal concentrations of the components of exemplary liposomal carfilzomib compositions (liposomal carfilzomib compositions, L-CFZ; pegylated liposomal carfilzomib compositions, pL-CFZ), as well as control compositions (i.e., "empty" liposomes).

TABLE 2A

| Composition Designation | Composition Name | CFZ* (mg/mL) | Phospholipid (mg/mL) | mPEG-DSPE (mg/mL) | Cholesterol (mg/mL) |
|---|---|---|---|---|---|
| A | Empty EPC Liposomes | 0 | 12.5 | 0 | 0 |
| B | 1 mg/mL Liposomal CFZ | 1 | 12.5 | 0 | 0 |
| C | 2 mg/mL Liposomal (EPC) CFZ | 2 | 12.5 | 0 | 0 |
| D | Empty PEG-Liposomes (EPC) | 0 | 12.5 | 1.3 | 0 |
| E | 2 mg/mL PEG-Liposomal (EPC) CFZ | 2 | 12.5 | 1.3 | 0 |
| F | Empty PEG-Liposomes (EPC) w/ Cholesterol | 0 | 12.5 | 1.3 | 3.1 |
| G | 2 mg/mL PEG-Liposomal (EPC) CFZ w/ Cholesterol | 2 | 12.5 | 1.3 | 3.1 |
| H | 2 mg/mL PEG-Liposomal (SPH) CFZ w/ Cholesterol | 2 | 12.5 | 1.3 | 3.1 |

*Total drug content may include unencapsulated drug that was not removed during processing.

The nominal concentrations of exemplary liposomal Compositions A to H are presented in Table 2A.

Note that the drug to lipid ratios in FIG. 1 (Drug:Lipid Ratio (%)) were calculated by taking the weight of drug (carfilzomib) divided by the weight of drug plus weight of phospholipid (wt. drug/(wt. drug+wt. phospholipid)). However, the more conventional calculation is a ratio of the weight of drug to the weight of total lipids (e.g. phospholipid, hydrophilic polymer-derivatized lipid, cholesterol; see, e.g., Table 3). The more conventional calculation of Drug:Total Lipid Ratio for the specific experimental formulations in FIG. 1 are presented in Table 2B.

TABLE 2B

| Lot | Composition Desig. | Composition Name | CFZ (mg) | Total lipids (mg) | Drug:Total lipid (wt. ratio) | Lipid composition[1] |
|---|---|---|---|---|---|---|
| 6005-27B | A | Empty liposomes | 0 | 104.1 | 0.000:1 | 1:0:0 |
| 6005-29C | B | 1 mg/mL liposomal CFZ | 5.8 | 111.3 | 0.052:0.948 | 1:0:0 |
| 6005-35B | D | Empty PEG-liposomes | 0 | 101.7 | 0.000:1 | 0.90:0.10:0 |
| 6005-45A | C | 2 mg/mL Liposomal CFZ | 17.2 | 112.3 | 0.153:0.847 | 1:0:0 |
| 6005-45B | C | 2 mg/mL Liposomal CFZ | 16.5 | 105.5 | 0.156:0.844 | 1:0:0 |
| 6005-45A/B Pooled | C | 2 mg/mL Liposomal CFZ | 16.85 | 108.9 | 0.155:0.845 | 1:0:0 |
| 6005-45C | E | 2 mg/mL PEG-liposomal CFZ | 17 | 107.3 | 0.158:0.842 | 0.88:0.12:0 |
| 6005-45D | E | 2 mg/mL PEG-liposomal CFZ | 16 | 105.4 | 0.152:0.848 | 0.89:0.11:0 |
| 6005-45C/D Pooled | E | 2 mg/mL PEG-liposomal CFZ | 16.5 | 106.35 | 0.155:0.845 | 0.89:0.11:0 |
| 6005-53A | C | 2 mg/mL Liposomal CFZ | 22.6 | 130.6 | 0.173:0.827 | 1:0:0 |
| 6005-53D | C | 2 mg/mL Liposomal CFZ | 41.9 | 251.8 | 0.166:0.834 | 1:0:0 |
| 6005-53A/D Pooled | C | 2 mg/mL Liposomal CFZ | 32.25 | 191.2 | 0.169:0.831 | 1:0:0 |
| 6005-53C | A | Empty Liposomes | 0 | 129.8 | 0.000:1 | 1:0:0 |
| 6005-67B | C | 2 mg/mL Liposomal CFZ | 41.7 | 252.9 | 0.165:0.835 | 1:0:0 |
| 6005-69A | C | 2 mg/mL Liposomal CFZ | 21.3 | 126.9 | 0.168:0.832 | 1:0:0 |
| 6005-69B | A | Empty Liposomes | 0 | 125.9 | 0.000:1 | 1:0:0 |
| 6005-71D | F | Empty PEG Liposomes w/ Cholesterol | 0 | 169.1 | 0.000:1 | 0.74:0.08:0.18 |
| 6005-71E | G | 2 mg/mL PEG liposomal CFZ w/ cholesterol | 20 | 172.4 | 0.116:0.884 | 0.74:0.08:0.18 |

[1] = (phospholipid wt./total lipid wt.:mPEG-DSPE wt./total lipid wt.:cholesterol wt./total lipid wt.)

Table 3 presents example ranges of components to be used in liposomal carfilzomib compositions of the present invention, as well as control compositions (i.e., "empty" liposomes). In the table, preferred phospholipids include EPC, HSPC, DSPC, DPPC, DSPG, POPC, SPH, DSPE, or combinations thereof

TABLE 3

| Composition Type | Drug:Total Lipid Weight Ratio (wt. %) | Total Lipid Weight Ratio (Phospholipid:Hydrophilic Polymer-derivatized Lipid:Cholesterol) (wt. %) |
|---|---|---|
| Empty Liposomes = Empty L | 0:1 (0 wt. % drug/100 wt. % Total Lipid) | 1:0:0 (100 wt. % Phospholipid) |
| Liposomal CFZ = L-CFZ | 0.005:0.995 to 0.35:0.65 (0.5 wt. % drug/95.5 wt. % Total Lipid to 35 wt. % drug/65 wt. % Total Lipid) | 1:0:0 (100 wt. % Phospholipid) |

TABLE 3-continued

| Composition Type | Drug:Total Lipid Weight Ratio (wt. %) | Total Lipid Weight Ratio (Phospholipid:Hydrophilic Polymer-derivatized Lipid:Cholesterol) (wt. %) |
| --- | --- | --- |
| Empty Liposomes w/ Cholesterol = Empty L Chol | 0:1 (0 wt. % drug/100 wt. % Total Lipid) | 0.9:0:0.1 to 0.5:0:0.5 (90 wt. % Phospholipid/10 wt. % Cholesterol to 50 wt. % Phospholipid/50 wt. % Cholesterol) |
| Liposomal CFZ w/ Cholesterol = L-CFZ Chol | 0.005:0.995 to 0.35:0.65 (0.5 wt. % drug/95.5 wt. % Total Lipid to 35 wt. % drug/65 wt. % Total Lipid) | 0.9:0:0.1 to 0.5:0:0.5 (90 wt. % Phospholipid/10 wt. % Cholesterol to 50 wt. % Phospholipid/50 wt. % Cholesterol) |
| Empty PEGylated Liposomes = Empty pL | 0:1 (0 wt. % drug/100 wt. % Total Lipid) | 0.9:0.1:0 to 0.75:0.25:0 (90 wt. % Phospholipid/10 wt. % Hydrophilic polymer-derivatized lipid to 75 wt. % Phospholipid/25 wt. % Hydrophilic polymer-derivatized lipid) |
| PEGylated Liposomal CFZ = pL-CFZ | 0.005:0.995 to 0.35:0.65 (0.5 wt. % drug/95.5 wt. % Total Lipid to 35 wt. % drug/65 wt. % Total Lipid) | 0.9:0.1:0 to 0.75:0.25:0 (90 wt. % Phospholipid/10 wt. % Hydrophilic polymer-derivatized lipid to 75 wt. % Phospholipid/25 wt. % Hydrophilic polymer-derivatized lipid) |
| Empty PEGylated Liposomes w/ Cholesterol = Empty pL Chol | 0:1 (0 wt. % drug/100 wt. % Total Lipid) | 0.833:0.0833:0.0833 to 0.57:0.14:0.29 (83.3 wt. % Phospholipid/8.33 wt. % Hydrophilic polymer-derivatized lipid/8.33 wt. % Cholesterol to 57 wt. % Phospholipid/14 wt. % hydrophilic polymer-derivatized lipid/29 wt. % Cholesterol |
| PEGylated Liposomal CFZ w Cholesterol = pL-CFZ Chol | 0.005:0.995 to 0.35:0.65 (0.5 wt. % drug/95.5 wt. % Total Lipid to 35 wt. % drug/65 wt. % Total Lipid) | 0.833:0.0833:0.0833 to 0.57:0.14:0.29 (83.3 wt. % Phospholipid/8.33 wt. % Hydrophilic polymer-derivatized lipid/8.33 wt. % Cholesterol to 57 wt. % Phospholipid/14 wt. % Hydrophilic polymer-derivatized lipid/29 wt. % Cholesterol |

Example 2

Lipid Hydration

The thin-filmed, round-bottom flask was immersed in a water bath set above the highest gel-liquid crystal phase transition. When EPC was used, rehydration occurred at room temperature. For DSPC, DPPC, and mPEG-DSPE, the water bath temperature should be set greater than 55° C., 41° C., and 50° C., respectively. An appropriate volume of phosphate buffered saline, pH 7.2, or water for injection was added to the lipid film to achieve the desired target carfilzomib concentration or dose. The flask was mildly agitated or shaken with intermittent vortexing, as needed, and sonicated in water bath at the appropriate Tc temperature for 1 to 2 minutes to facilitate complete hydration from flask walls.

After the film was dispersed, the mixture was transferred to a vial and sonicated for an additional 20 to 40 minutes in a water bath above the Tc to size the liposomes. When EPC was used, the temperature of the water bath in the sonicator was kept near room temperature. Upon hydration the lipid suspension appeared as a slightly hazy or milky solution.

FIG. 1 sets forth the composition of exemplary liposomal carfilzomib compositions of the present invention, as well as control compositions (i.e., "empty" liposomes) used in the studies described below. The nominal concentrations of exemplary liposomal Compositions A to G are presented in Table 2A.

Example 3

Characterization of Liposomes

Particle size reduction and/or deagglomeration of the rehydrated liposomal suspension was carried out by sonication (20 to 60 minutes).

The CFZ content of exemplary liposomal carfilzomib compositions was determined by HPLC as described above. The liposomal compositions were each diluted in methanol to dissolve lipids and carfilzomib. The solution was filtered through a 0.2 μm PTFE filter prior to HPLC analysis. The percent difference between the theoretical and experimental liposomal drug concentrations for the prepared lots (FIG. 1) were typically 2% or less (except for one of the first lots which had a 12% difference). The results of the HPLC analysis are presented in FIG. 1.

Based on polarized light microscope it was qualitatively determined that nearly all of the drug was entrapped in the liposomes. Any free drug would precipitate in the aqueous medium due to its extremely low aqueous solubility of <1 μg/mL and any precipitated material could be easily observed under the polarized light microscope. No visible precipitate was observed under the polarized light microscope.

Example 4

Tolerability of Liposomal Carfilzomib

The tolerability of carfilzomib incorporated in either liposomal (L-CFZ) or pegylated liposomal (pL-CFZ) carfilzomib compositions was evaluated in both mice and rats above the maximum tolerated dose (MTD) achieved using an injectable composition of carfilzomib formulated in 10% sulfobutylether beta cyclodextrin (SBE-β-CD, also referred to as CFZ SBE-B-CD), 10 mM Citrate, pH 3.5 (see, e.g., U.S. Patent Publication Nos. 2011/0236428).

Liposomal compositions prepared in Example 2 and characterized in Example 3 were rehydrated with an appropriate volume of aqueous medium to achieve a target carfilzomib concentration in the range of approximately 1 to 2 mg/ml (see composition data in FIG. 1). Toxicity for both L-CFZ and pL-CFZ compositions were tested in mice (Table 4). Toxicity for L-CFZ was tested in rats (Table 5).

Female BALB/c mice (7-8 week old; 5/cohort) were dosed intravenously as follows: 15 mg/kg CFZ SBE-B-CD (7.5 mL/kg); 10 mg/kg L-CFZ (5 mL/kg); 10 mg/kg pL-CFZ (5 mL/kg); 15 mg/kg L-CFZ (7.5 mL/kg); 15 mg/kg pL-CFZ (7.5 mL/kg); 20 mg/kg L-CFZ (10 mL/kg); 20 mg/kg pL-CFZ (10 mL/kg); 25 mg/kg L-CFZ (12.5 mL/kg); 25 mg/kg pL-CFZ (12.5 mL/kg); 30 mg/kg L-CFZ (15 mL/kg); 35 mg/kg L-CFZ (17.5 mL/kg); or empty liposome (15 mL/kg).). Survival was then monitored over a seven day period. The survival rates of mice, the liposomal compositions, and dosing used for treatment were as shown in Table 4.

TABLE 4

| Group | Composition Desig. (Dose Volume) | Dose (mg/kg) | Overall Mortality (No. dead/total) |
|---|---|---|---|
| CFZ alone (10 mg/kg MTD) | 2 mg/mL SBE-B-CD Composition (150 µL) | 15 | 5/5 |
| Empty Liposome | Composition A (300 µL) | 0 | 0/5 |
| L-CFZ | Composition B (200 µL) | 10 | 0/5 |
| L-CFZ | Composition C (150 uL) | 15 | 0/5 |
| L-CFZ | Composition C (200 uL) | 20 | 0/5 |
| L-CFZ | Composition C (250 uL) | 25 | 0/5 |
| L-CFZ | Composition C (300 uL) | 30 | 1/5 |
| L-CFZ | Composition C (350 uL) | 35 | 4/5 |
| Empty PEG Liposome | Composition D (300 µL) | 0 | 0/5 |
| pL-CFZ | Composition E (100 uL) | 10 | 0/5 |
| pL-CFZ | Composition E (150 uL) | 15 | 0/5 |
| pL-CFZ | Composition E (200 uL) | 20 | 5/5 |
| pL-CFZ | Composition E (250 uL) | 25 | 5/5 |

Male Sprague Dawley rats (5/cohort) weighing approximately 250-300 grams were dosed intravenously with the following: 8 mg/kg CFZ (SBE-B-CD composition) (5 mL/kg); 8 mg/kg L-CFZ (4 mL/kg); 10 mg/kg L-CFZ (5 mL/kg); 12.5 mg/kg L-CFZ (6 mL/kg); or empty liposome (5 mL/kg). Survival was then monitored over a seven day period. The survival rates of dosed rats were as shown in Table 5.

TABLE 5

| Group | Composition Desig. (mL/kg) | Dose (mg/kg) | Overall Mortality (No. dead/total) |
|---|---|---|---|
| CFZ (7 mg/kg MTD) | SBE-B-CD Composition (5 mL/kg) | 8 | 2/5 |
| Empty Liposome | Composition A (5 mL/kg) | 0 | 0/5 |
| L-CFZ | Composition C (4 mL/kg) | 8 | 0/5 |
| L-CFZ | Composition C (5 mL/kg) | 10 | 0/5 |
| L-CFZ | Composition C (6.25 mL/kg) | 12.5 | 3/5 |

Liposomal carfilzomib significantly enhanced tolerability (Table 4) by increasing the maximum tolerated dose (MTD) of carfilzomib in mice by approximately 2.5 fold for the liposomal carfilzomib compositions and by 0.5 fold with PEGylated liposomal carfilzomib compositions compared to SBE-B-CD based carfilzomib composition. Only a slight increase in the MTD in rats was observed with liposomal carfilzomib L-CFZ (10 mg/kg) compared to carfilzomib (7 mg/kg) formulated in SBE-B-CD.

These data demonstrate that liposomal compositions comprising peptide epoxyketone compounds significantly enhanced tolerability by increasing the maximum tolerated dose (MTD) of a peptide epoxyketone compound relative to non-liposomal compositions comprising peptide epoxyketone compounds.

Example 5

Pharmacodynamic Response of CFZ Liposomal Compositions

The pharmacodynamic response of carfilzomib formulated in SBE-B-CD (CFZ SBE-B-CD) (using a non-liposomal, injectable composition of carfilzomib formulated in 10% sulfobutylether beta cyclodextrin (SBE-B-CD), 10 mM Citrate, pH 3.5 (see, e.g., U.S. Patent Publication Nos. 2011/0236428)), empty liposomes (Composition D), liposomes comprising CFZ (L-CFZ, Composition C), and pegylated liposomes comprising (pL-CFZ, Composition E) was evaluated in BALB/C mice following a single intravenous bolus administration.

The mice (three mice per time point) were administered a dose of 10 mg/kg in a dose volume of 5 mL/kg. Blood samples and tissues for pharmacodynamic testing were taken at 1, 8, and 24 hours after administration of each composition. The pharmacodynamic response was determined by measurement of proteasome activity in whole blood (primarily erythrocytes) (see FIG. 2A), adrenal (see FIG. 2B), liver (see FIG. 2C), and heart (see FIG. 2D), using a fluorogenic substrate (LLVY-AMC [Leu-Leu-Val-Tyr-AMC {AMC=7-amido 4-methylcoumarin}]; as described by Lightcap E S, McCormack T A, Pien C S, et al., *Clin. Chem.* 46:673-683 (2000)) to quantitate the chymotrypsin-like activity of the proteasome. All samples were normalized to the appropriate vehicle (i.e., the corresponding composition without CFZ), and the vehicle time point was 1 hour post dose. Three tissue samples were evaluated per time point for each tissue from each mouse.

A single intravenous dose of 10 mg/kg resulted in rapid proteasome inhibition of >80% within 1 hour in whole blood and all tissues. Similar and complete recovery from proteasome inhibition was observed 24 hours post-dose in all tissues tested except for the blood and heart and occurred with at $t_{1/2}$ of 8-24 hours for all compositions. The slower recovery observed in the heart with both the liposomes and pegylated liposomes suggest that the heart tissue may act as a depot. As expected, there was no recovery of proteasome activity in blood due to the irreversible binding of carfilzomib and the lack of the erythrocytes to synthesize new proteasome.

These observations indicate that inhibition of proteasome activity in whole blood and tissues is rapid, similar across compositions. The liposomal compositions did not adversely affect biodistribution of CFZ.

Example 6

Circulation Half-Life of Liposomal CFZ

Circulation half-life of liposomal CFZ was evaluated in 7-8 week old female BALB/c mice (3/time point) following a single i.v. injection of either 5 mg/kg CFZ formulated in 10% sulfobutylether beta cyclodextrin, 10 mM Citrate, pH 3.5 (non-liposomal) or 15 mg/kg of liposomal carfilzomib compositions.

When CFZ was delivered in the composition containing SBE-B-CD at 5 mg/kg, plasma concentration rapidly declines with time and drops to below the limit of quantitation (BLOQ; limit of quantitation—LOQ) after 60 minutes (Table 6). The terminal plasma half-life ($t_{1/2}$) was about 20 minutes.

TABLE 6

Plasma Levels of CFZ Using SBE-B-CD Composition
I.V. Bolus 5 mg/kg in BALB/c Mice

| Time (min) | Plasma Conc. (uM) | |
|---|---|---|
| | Mean | STD |
| 0 | 0 | 0 |
| 2 | 10.379 | 0.844 |
| 5 | 1.732 | 0.431 |
| 10 | 0.310 | 0.064 |
| 20 | 0.176 | 0.040 |
| 30 | 0.061 | 0.011 |
| 60 | 0.042 | 0.032 |

LOQ = 1 ng/mL (MW = 719.4)

When delivered in liposomal compositions at 15 mg/kg (using L-CFZ, Composition C, or pL-CFZ-Chol, Composition G, with a dose volume of 150 μL), detectable CFZ was observed at 6 hours post-dosing (Table 7).

TABLE 7

Mean Plasma Levels of Liposomal CFZ
IV bolus at 15 mg/kg in BALB/c Mice

| | Plasma Conc. (uM) Liposomal CFZ Composition C | | Plasma Conc. (uM) PEGylated Liposomal CFZ Composition G | |
|---|---|---|---|---|
| Time (min) | Mean | STD | Mean | STD |
| predose | BLOQ | BLOQ | BLOQ | BLOQ |
| 2 | 102 | 21 | 79.0 | 22.7 |
| 5 | 51.4 | 9.1 | 42.5 | 8.4 |
| 10 | 22.2 | 6.2 | 9.81 | 3.48 |
| 30 | 1.26 | 0.48 | 0.183 | 0.045 |
| 60 | 0.143 | 0.018 | 0.0537 | 0.0200 |
| 120 | 0.0424 | 0.0134 | 0.0111 | 0.0010 |
| 240 | 0.0125 | 0.0010 | 0.0152 | 0.0070 |
| 360 | 0.0129 | 0.0023 | 0.0122 | 0.0100 |

The $t_{1/2}$ was 140 and 201 minutes, respectively, for liposomal CFZ and pegylated liposomal CFZ compositions, respectively. The data for liposomal CFZ compositions versus CFZ SBE-B-CD, clearly demonstrate the ability of liposome to significantly enhance the circulation half-life of peptide epoxyketone compounds.

Circulation half-life of liposomal CFZ was also evaluated in male Sprag-Dawley rats (3/time point) weighing approximately 250-300 grams following a single i.v. injection of 8 mg/kg CFZ formulated in 10% sulfobutylether beta cyclodextrin, 10 mM Citrate, pH 3.5, or 8 mg/kg liposomal CFZ. Similar to mice, a rapid decline in plasma concentration was observed in rats when CFZ SBE-B-CD was delivered (Table 8), with a plasma $t_{1/2}$ of 17 minutes. When CFZ was delivered in liposomal compositions (L-CFZ, Composition C, FIG. 1, with a dose volume of 4 mL/kg) at the same dose level, detectable CFZ was observed at 4 hours post-dosing (Table 8), with a $t_{1/2}$ of about 50 minutes.

TABLE 8

Plasma Levels of CFZ Using SBE-B-CD Composition or Liposomal CFZ
(IV bolus at 8 mg/kg) in Rats

| | SBE-B-CD Composition | | Liposomal-CFZ Composition C | |
|---|---|---|---|---|
| | Plasma Conc. (uM) | | | |
| Time (min) | Mean | STD | Mean | STD |
| predose | BLOQ | BLOQ | BLOQ | BLOQ |
| 0.1 | 42.9 | 4.4 | ND | ND |
| 1 | 3.93 | 0.36 | ND | ND |
| 2 | 1.90 | 0.26 | 36.9 | 4.8 |
| 5 | 0.651 | 0.115 | 21.0 | 1.8 |
| 15 | 0.0505 | 0.0030 | 0.583 | 0.072 |
| 30 | 0.0189 | 0.0030 | 0.139 | 0.050 |
| 60 | 0.0072 | 0.0020 | 0.058 | 0.029 |
| 120 | ND | ND | 0.012 | 0.003 |
| 240 | ND | ND | 0.004 | 0.001 |
| 420 | ND | ND | BLOQ | BLOQ |

The data presented in Table 9 and Table 10 demonstrate that, compared to CFZ SBE-B-CD, the exposure (AUC) to liposomal CFZ compositions (L-CFZ Composition C) and pegylated liposomal CFZ compositions (pL-CFZ Composition E), was increased about 5 to 7 and 20-fold in mice and rats, respectively.

TABLE 9

Mean AUC Levels of CFZ Using SBE-B-CD Composition or Liposomal
CFZ (IV bolus at 15 mg/kg) in Mice

| Species | Dose (mg/kg) | Composition | AUCinf (min * μmol/L) | Relative Increase AUC-$_{liposome}$/ AUC-$_{SBE-B-CD}$ |
|---|---|---|---|---|
| Mouse | 15 | SBE-B-CD | 130.5 | — |
| Mouse | 15 | L-CFZ-C | 942.8 | 7 |
| Mouse | 15 | pL-CFZ-E | 623.3 | 5 |

TABLE 10

Mean AUC Levels of CFZ Using SBE-B-CD Composition or Liposomal
CFZ (IV bolus at 8 mg/kg) in Rats

| Species | Dose (mg/kg) | Composition | AUCinf (min * μmol/L) | Relative Increase AUC-$_{liposome}$/ AUC-$_{SBE-B-CD}$ |
|---|---|---|---|---|
| Rat | 8 | SBE-B-CD | 14.5 | — |
| Rat | 8 | L-CFZ-C | 297.7 | 20 |

The increased AUC is significant because AUC is determined by measuring drug clearance rates and these data demonstrate that the liposomal compositions of the present invention are decreasing clearance of peptide epoxyketone compounds. These data demonstrate the extended duration of exposure to peptide epoxyketone compounds in liposomal composition versus the non-liposomal SBE-B-CD composition.

Example 7

Preparation of Thin Lipid Film and Use in Preparing Liposomes Comprising an Aqueous Core Loaded with Peptide Epoxyketone Compounds Complexed with SBE-B-CD To make the PEGylated liposomal film, the following materials at their indicated ratios were added to a suitably sized round bottom flask. Total lipids typically comprise the lipids EPC, HSPC, DSPC, DPPC, DSPG, POPC, SPH, DSPE, or combinations thereof, with PEG-derivatized lipids (e.g., PEG-derivatized phospholipids) in weight ratio (phospholipids:PEG-derivatized lipids) of from 0.9:0.1 to 0.75:0.25, or when cholesterol is added the phospholipid to PEG-derivatized lipid to cholesterol weight ratio (phospholipid:PEG-derivatized lipid:cholesterol) is from 0.83:0.083:0.083 to 0.57:0.14:0.29.

To dissolve the lipids, an appropriate volume of organic solvent (e.g., cloroform:MeOH (60:40 v/v)), enough to achieve between 10-20 mg/mL dissolved lipid, was added to the flask. The flask was attached to a rotary evaporator spinning at 100 rpm and immersed in a water bath set above the highest gel-liquid crystal phase transition (Tc) temperature of the lipids used. Although the Tc for egg phosphatidylcholine is below room temperature (−15° C. to −7° C.), the temperature bath used for EPC was approximately 45° C. to 50° C. For DSPC, DPPC, and mPEG-DSPE, the water bath temperature should be set greater than 55° C., 41° C., and 50° C., respectively. If there is no phase transition temperature, the water bath temperature is set between 35-45° C.

The flask was allowed to rotate in the water bath for approximately 1 minute to equilibrate. A slow vacuum was pulled, to as low as <10 Torr, to obtain a thin dry film on the walls of the flask without precipitation (typically for about 30 minutes). To remove any residual solvent, the flask was subjected to high vacuum at room temperature for a few hours or overnight.

Carfilzomib (CFZ) was solubilized in an aqueous solution by complexation with sulfobutylether beta cyclodextrin (SBE-B-CD). Excess carfilzomib was added to an aqueous solution of 20% SBE-B-CD and 20 mM citric acid. The solution pH was adjusted to approximately pH 2.5 with 1N HCl, if needed to solubilize CFZ. The mixture was sonicated for approximately 10 minutes and stirred using a magnetic stir bar for not less than an hour prior to filtration through a 0.2 μm filter to remove excess undissolved drug. After filtration the solution pH was adjusted to between pH 3.5 and 5. This aqueous solution of CFZ complexed with SBE-B-CD was used to rehydrate the thin lipid film.

Once the vesicles were rehydrated the unencapsulated free drug was removed by centrifugation at 31000 rpm for 30 minutes and washing with PBS or by being dialyzed using a membrane with a MWCO of 8-10 kD in PBS for up to 48 hours.

Table 11 presents nominal concentrations of the components of exemplary liposomal compositions comprising liposomes comprising an aqueous core loaded with CFZ complexed with SBE-B-CD.

TABLE 11

| Composition Designation | Lipid composition | Total Lipid Weight Ratios | Drug:Total Lipid Ratio* | Drug content** |
|---|---|---|---|---|
| apL | 12.5 mg/mL EPC, 1.3 mg/mL mPEG-DSPE, 3.3 mg/mL cholesterol | 0.73:0.08:0.19 | 0.05:0.95 | 0.9 mg/mL |
| apL-9 | 25 mg/mL EPC, 2.5 mg/mL mPEG-DSPE, 6.3 mg/mL cholesterol | 0.73:0.08:0.19 | 0.04:0.96 | 1.3 mg/mL |
| apL-11 (for 15 mg/kg dosing) | 12.5 mg/mL egg SPH, 1.3 mg/mL mPEG-DSPE, 3.3 mg/mL cholesterol | 0.73:0.08:0.19 | 0.05:0.95 | 0.8 mg/mL |
| apL-11 (for 5 mg/kg dosing) | 12.5 mg/mL egg SPH, 1.3 mg/mL mPEG-DSPE, 3.3 mg/mL cholesterol | 0.73:0.08:0.19 | 0.01:0.99 | 0.2 mg/mL |

*assuming 100% drug encapsulation
**Total drug content may include unencapsulated drug that was not removed during processing.

Example 8

Pharmacodynamic Response of CFZ Liposomal Compositions Comprising Liposome Comprising an Aqueous Core Loaded with Peptide Epoxyketone Compounds Complexed with SBE-B-CD The pharmacodynamic response of liposomal compositions comprising liposomes comprising an aqueous core loaded with CFZ complexed with SBE-B-CD was evaluated in BALB/C mice following a single intravenous bolus administration.

The pharmacodynamic response of injectable carfilzomib formulated in SBE-B-CD (non-liposomal; see, e.g., U.S. Patent Publication Nos. 2011/0236428) or liposomal compositions comprising liposomes comprising an aqueous core loaded with CFZ complexed with SBE-B-CD was evaluated in BALB/C mice (apL-11 (for 15 mg/kg dosing), Example 7; and apL-11 (for 5 mg/kg dosing), Example 7) following a single intravenous bolus administration. The mice (three mice per time point) were administered a dose of 5 or 10 mg/kg of non-liposomal carfilzomib or 5 or 15 mg/kg of liposomal carfilzomib as a solution in a dose volume of 5 mL/kg. Blood samples and tissues for pharmacodynamic testing were taken at 0, 1, 8, and 14 hours after administration of the non-liposomal composition at 10 mg/kg; 0, 1, 4, 6, 8 and 24 hours after administration of the non-liposomal composition at 5 mg/kg; and 0, 1, 4, 6, and 24 hours after administration of the liposomal compositions at 5 mg/kg and 15 mg/kg. Three tissue samples were evaluated per time point for each tissue from each mouse. The pharmacodynamic response was determined by measurement of proteasome activity in whole blood (primarily erythrocytes), adrenal, liver, and heart using a fluorogenic substrate (LLVY-AMC; as described by Lightcap E S, McCormack T A, Pien C S, et al., *Clin. Chem.* 46:673-683 (2000)) to quantitate the chymotrypsin-like activity of the proteasome. All samples were normalized to the corresponding vehicle without CFZ, and the vehicle sample time point measurement was 1 hour post dose.

A single dose of injectable carfilzomib formulated in SBE-B-CD (non-liposomal) at either 5 or 10 mg/kg or liposomal compositions comprising liposomes comprising an aqueous core loaded with CFZ complexed with SBE-B-CD (apL-11) at either 5 or 15 mg/kg resulted in a rapid inhibition of proteasome activity within 1 hour in whole blood and all other tissues. Greater inhibition of proteasome activity was observed at the 15 mg/kg dose, which resulted in >80% inhibition of proteasome activity at 1 hour in all tissue: whole blood (primarily erythrocytes) (see FIG. 3A), heart (see FIG. 3B), liver (see FIG. 3C), and adrenal (see FIG. 3D). Similar and near complete recovery from proteasome inhibition was observed 24 hours post-dose in all tissues tested except for the blood and heart and occurred with at $t_{1/2}$ of 6-24 hours for both the 5 and 10 mg/kg dose levels of injectable carfilzomib formulated in SBE-B-CD (non-liposomal). Delayed recovery of proteasome activity in the adrenals was observed with liposomal compositions comprising liposomes comprising an aqueous core loaded with CFZ complexed with SBE-B-CD at both 5 and 15 mg/kg; this result suggests long term exposure of CFZ. As expected, there was no recovery of proteasome activity in blood due to the irreversible binding of carfilzomib and the lack of the erythrocytes to synthesize new proteasome.

These observations indicate that inhibition of proteasome activity in whole blood and tissues was rapid and similar across between the non-liposomal composition and liposomal compositions comprising peptide epoxyketone compounds. Further, the delay in the recovery of proteasome activity in the adrenals with liposomal compositions comprising liposomes comprising an aqueous core loaded with peptide epoxyketone compound complexed with SBE-B-CD suggests extended exposure with the liposomal composition versus the non-liposomal composition. Further, the liposomal compositions comprising peptide epoxyketone compounds did not adversely affect biodistribution of the peptide epoxyketone compounds.

Example 9

Circulation Half-Life of Liposomal CFZ

Circulation half-life of liposomal CFZ was evaluated in 7-8 week old female BALB/c mice (3/time point) following a single i.v. injection of the following: 5 mg/kg CFZ formulated in 10% sulfobutylether beta cyclodextrin (CAPTISOL®), 10 mM Citrate, pH 3.5 (CFZ SBE-B-CD; non-liposomal); 5 mg/kg of liposomal carfilzomib compositions apL-11 (Example 7; apL-11 (for 5 mg/kg dosing)) and 15 mg/kg of liposomal carfilzomib compositions apL-11 (Example 7; apL-11 (for 15 mg/kg dosing)).

As shown in FIG. 4, the plasma concentration of injectable carfilzomib SBE-B-CD composition (non-liposomal) declined rapidly following intravenous, bolus administration due to rapid and extensive metabolism (FIG. 4: open squares containing an X corresponds to administration of 5 mg/kg of an injectable carfilzomib SBE-B-CD composition (non-liposomal). The half-life of carfilzomib dosed at 5 mg/kg was about 20 minutes and carfilzomib was not detectable after 1 hour post-dose.

When delivered in liposomal compositions, the duration of exposure to carfilzomib was greatly extended (FIG. 4, solid squares correspond to administration of 5 mg/kg of apL11 (Example 7), a pegylated liposomal composition of carfilzomib wherein the aqueous core of the pegylated liposomes comprises carfilzomib and SBE-B-CD; solid circles correspond to administration of 15 mg/kg of apL11 (Example 7), a pegylated liposomal composition of carfilzomib wherein the aqueous core of the pegylated liposomes comprises carfilzomib and SBE-B-CD). Total drug (encapsulated and released) was detectable for up to 24 hours post-dose. This is consistent with the observed delay in proteasome recovery in tissues.

The data for liposomal CFZ compositions versus CFZ SBE-B-CD (non-liposomal), demonstrate the ability of liposomal compositions to significantly enhance the circulation half-life of peptide epoxyketone compounds. Further, the data show the ability to provide extended duration of exposure to peptide epoxyketone compounds in liposomal compositions versus the non-liposomal SBE-B-CD composition.

Example 10

Preparation of Liposomes Comprising an Aqueous Core Loaded with Peptide Epoxyketone Using pH Control and an Ethanol Injection Method To make the liposomal compositions using an ethanol injection method, the following materials at their indicated ratios were used. Phospholipids typically comprise the lipids EPC, HSPC, DSPC, DPPC, DSPG, POPC, SPH, DSPE, or combinations thereof. When PEG-derivatized lipids are present (e.g., PEG-derivatized phospholipids) the typical weight ratio for total lipids (phospholipids:PEG-derivatized lipids) is from 0.9:0.1 to 0.75:0.25. Further, when cholesterol is also added the typical weight ratio for total lipids (phospholipids:PEG-derivatized lipids:cholesterols) is from 0.833:0.0833:0.0833 to 0.57:0.14:0.29.

Other materials used in the ethanol injection method include the following: absolute Ethanol; 1N HCl; Carfilzomib (crystalline or amorphous); Hamilton Syringe Gastight, 22 gauge; Dialysis kit, Spectra/Por® Float-A-Lyzer® G2 (Spectrum Laboratories Inc., Rancho Dominguez, Calif.) molecular weight cut off (MWCO) 8-10 kD; Water for Injection (WFI); and Phosphate buffer saline 1× (PBS).

A lipid/ethanol solution was prepared as follows: 2 mL of ethanol containing 125 mg/mL egg sphingomyelin, 31.25 mg/mL cholesterol, 12.5 mg/mL mPEG-DSPE. If needed, the lipid/ethanol solution was sonicated several minutes to facilitate dissolution.

An aqueous solution of CFZ was prepared as follows: 10 mL of a 0.1M HCl aqueous solution was prepared (~pH 1) and CFZ in excess of solubility was added. The aqueous solution was sonicated in heated water bath (~30° C.) for 20-30 minutes. Approximate carfilzomib solubility at pH 1 is 1.8 mg/mL. Undissolved excess drug was removed by filtering through a 0.2 μm filter to yield a visibly clear solution.

Alternatively, a supersaturated solution of carfilzomib was prepared by dissolving amorphous carfilzomib in 0.1M HCl solution with 6% (v/v) ethanol as a cosolvent followed by sonication in a warm water bath until the solution became clear.

Liposomes were formed by rapid injection of 1 mL of the lipid-ethanol solution into 9 mL of the aqueous solution of CFZ (prepared by one of the methods just described) with stirring using a magnetic stir bar. Stirring was continued for 5-10 minutes. The solution pH was ~pH 1. The resulting solution was dialyzed against phosphate buffer saline (or WFI) using the Dialysis kit (Spectra/Por® Float-A-Lyzer® G2) MWCO 8-10 kD for 12 to 16 hours. The bulk dialysis solution was replaced with fresh PBS or WFI after approximately 6-8 hours. Solution pH of the dialyzed liposome containing composition was about pH 3 to 3.5. The pH of the aqueous solution comprising the liposomes was adjusted with sodium hydroxide to between pH 3.5 to a physiologic pH, ~pH 6.8.

Table 12 presents nominal concentrations of the components of exemplary liposomal compositions.

TABLE 12

| Composition Designation | Lipid composition | Total Lipid Weight Ratios | Drug:Total Lipid Ratio* | Drug content** |
|---|---|---|---|---|
| apL-15 | 25 mg/mL egg SPH, 2.5 mg/mL mPEG-DSPE, 6.3 mg/mL cholesterol | 0.74:0.07:0.19 | 0.02:0.98 | 0.6 mg/mL |
| apL-11b | 12.5 mg/mL EPC, 1.2 mg/mL mPEG-DSPE, 3.1 mg/mL cholesterol | 0.74:0.08:0.18 | 0.06:0.94 | 1 mg/mL |

*assuming 100% drug encapsulation
**Total drug content may include unencapsulated drug that was not removed during processing.

Example 11

Liposomes Comprising Entrapped Peptide Epoxyketone Induce Anti-Tumor Response

To evaluate the anti-cancer effect of liposomal compositions comprising liposomes comprising peptide epoxyketone compounds, an exemplary liposomal composition was tested in a mouse xenograft tumor model.

The liposomal composition was made by the methods described in Example 1 and Example 2. The liposomal composition was as follows: pL6 (a specific formulation of Composition H; Table 2A)=2 mg/mL CFZ, 12.5 mg/mL Sphingomylin, 3.2 mg/mL cholesterol, 1.3 mg/mL mPEG-DSPE.

First, the pharmacodynamic response of injectable carfilzomib formulated in SBE-B-CD (non-liposomal; see, e.g., U.S. Patent Publication Nos. 2011/0236428) and the pL-6 a liposomal composition comprising liposomes loaded with CFZ was evaluated in BALB/C mice following a single intravenous bolus administration.

The mice (three mice per time point) were administered a dose of 10 mg/kg carfilzomib formulated in SBE-B-CD (non-liposomal) or 15 mg/kg of pL-6 a liposomal composition comprising liposomes loaded with CFZ as a solution in a dose volume of 7.5 mL/kg. Blood samples and tissues for pharmacodynamic testing were taken at 0, 1, 4, 6 and 24 hours after administration of the liposomal composition and 0, 1, 8, and 24 hours for the non-liposomal composition.

Three tissue samples were evaluated per time point for each tissue from each mouse. The pharmacodynamic response was determined by measurement of proteasome activity in whole blood (primarily erythrocytes), adrenal, liver, and heart using a fluorogenic substrate (LLVY-AMC; as described by Lightcap E S, McCormack T A, Pien C S, et al., Clin. Chem. 46:673-683 (2000)) to quantitate the chymotrypsin-like activity of the proteasome. All samples were normalized to the corresponding vehicle without CFZ, and the vehicle sample time point measurement was 1 hour post dose.

Figure 5A:
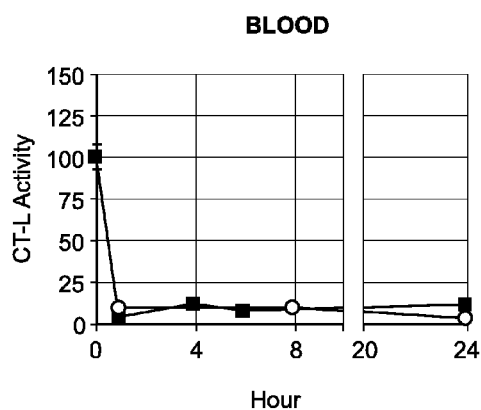
FIG. 5A presents data related to pharmacodynamic responses in BALB/C mice to different compositions of carfilzomib. In the figure, the vertical axis (CT-L Activity) is the percent (%) enzymatic activity relative to a corresponding vehicle without carfilzomib (CFZ), wherein the enzymatic activity corresponds to proteasome CT-L activity in whole blood (primarily erythrocytes). The horizontal axis is the time in hours (Hour). Two groups of data are presented. The first group (open circles) presents data for an injectable composition of carfilzomib (CFZ) formulated in 10% sulfobutylether beta cyclodextrin (SBE-B-CD), and 10 mM Citrate, pH 3.5, (non-liposomal) administered at 10 mg/kg with data points at 0, 1, 8, and 24 hours. The second group (solid squares) presents data for a liposomal composition of carfilzomib comprising liposomes comprising entrapped carfilzomib (pL-6) administered at 15 mg/kg with data points at 0, 1, 4, 6, and 24 hours. Error bars are represented bidirectionally.
Figure 5B:
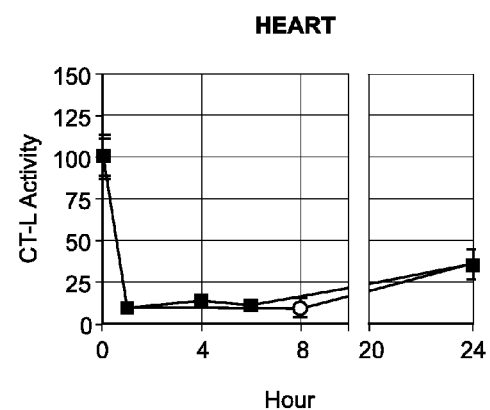
FIG. 5B presents data related to pharmacodynamic responses in BALB/C mice to different compositions of carfilzomib. In the figure, the vertical axis (CT-L Activity) is the percent (%) enzymatic activity relative to a corresponding vehicle without carfilzomib (CFZ), wherein the enzymatic activity corresponds to proteasome CT-L activity in heart tissue. The horizontal axis is the time in hours (Hour). Two groups of data are presented. The first group (open circles) presents data for an injectable composition of carfilzomib (CFZ) formulated in 10% sulfobutylether beta cyclodextrin (SBE-B-CD), and 10 mM Citrate, pH 3.5, (non-liposomal) administered at 10 mg/kg with data points at 0, 1, 8, and 24 hours. The second group (solid squares) presents data for a liposomal composition of carfilzomib comprising liposomes comprising entrapped carfilzomib (pL-6) administered at 15 mg/kg with data points at 0, 1, 4, 6, and 24 hours. Error bars are represented bidirectionally.
Figure 5C:
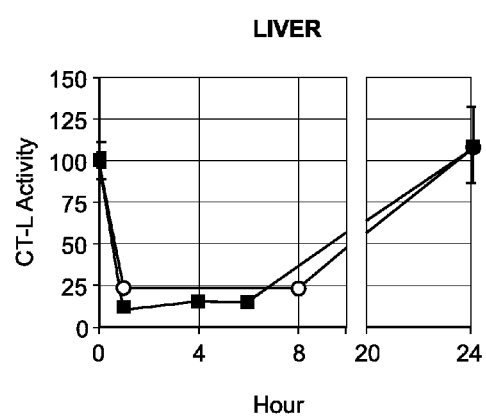
FIG. 5C presents data related to pharmacodynamic responses in BALB/C mice to different compositions of carfilzomib. In the figure, the vertical axis (CT-L Activity) is the percent (%) enzymatic activity relative to a corresponding vehicle without carfilzomib (CFZ), wherein the enzymatic activity corresponds to proteasome CT-L activity in liver tissue. The horizontal axis is the time in hours (Hour). Two groups of data are presented. The first group (open circles) presents data for an injectable composition of carfilzomib (CFZ) formulated in 10% sulfobutylether beta cyclodextrin (SBE-B-CD), and 10 mM Citrate, pH 3.5, (non-liposomal) administered at 10 mg/kg with data points at 0, 1, 8, and 24 hours. The second group (solid squares) presents data for a liposomal composition of carfilzomib comprising liposomes comprising entrapped carfilzomib (pL-6) administered at 15 mg/kg with data points at 0, 1, 4, 6, and 24 hours. Error bars are represented bidirectionally.
Figure 5D:
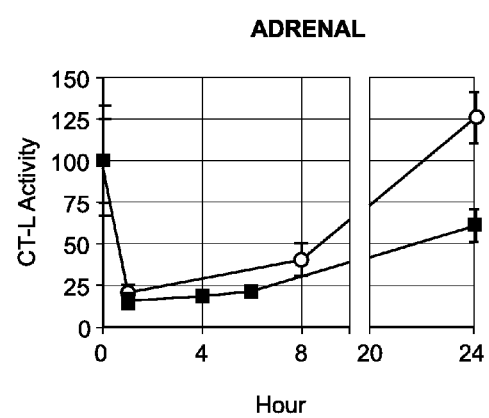
FIG. 5D presents data related to pharmacodynamic responses in BALB/C mice to different compositions of carfilzomib. In the figure, the vertical axis (CT-L Activity) is the percent (%) enzymatic activity relative to a corresponding vehicle without carfilzomib (CFZ), wherein the enzymatic activity corresponds to proteasome CT-L activity in adrenal tissue. The horizontal axis is the time in hours (Hour). Two groups of data are presented. The first group (open circles) presents data for an injectable composition of carfilzomib (CFZ) formulated in 10% sulfobutylether beta cyclodextrin (SBE-B-CD), and 10 mM Citrate, pH 3.5, (non-liposomal) administered at 10 mg/kg with data points at 0, 1, 8, and 24 hours. The second group (solid squares) presents data for a liposomal composition of carfilzomib comprising liposomes comprising entrapped carfilzomib (pL-6) administered at 15 mg/kg with data points at 0, 1, 4, 6, and 24 hours. Error bars are represented bidirectionally.

A single dose of injectable carfilzomib formulated in SBE-B-CD (non-liposomal) at 10 mg/kg (MTD) or liposomal compositions comprising liposomes comprising entrapped CFZ (pL-6) at 15 mg/kg resulted in a rapid inhibition of >80% of proteasome activity within 1 hour in whole blood and all other tissues: whole blood (primarily erythrocytes) (see FIG. 5A), heart (see FIG. 5B), liver (see FIG. 5C), and adrenal (see FIG. 5D). Similar and near complete recovery from proteasome inhibition was observed 24 hours post-dose in all tissues tested except for the blood and heart and occurred with a $t_{1/2}$ of 6-24 hours for the non-liposomal injectable CFZ. Delayed recovery of proteasome activity in the adrenals was observed with the liposomal composition pL-6 suggesting long-term exposure to CFZ. As expected, there was no recovery of proteasome activity in blood due to the irreversible binding of carfilzomib and the lack of the erythrocytes to synthesize new proteasome.

These observations indicate that inhibition of proteasome activity in whole blood and tissues is rapid and similar across compositions. The delay in recovery of proteasome activity in the adrenals suggests extended exposure with the liposomal composition. The liposomal compositions did not adversely affect biodistribution of CFZ.

Second, circulation half-life of liposomal CFZ was evaluated in 7-8 week old female BALB/c mice (3/time point) following a single i.v. injection of the following: injectable carfilzomib formulated in SBE-B-CD (non-liposomal) administered at 5 mg/kg; and the pL-6 a liposomal composition comprising liposomes loaded with CFZ administered at 15 mg/kg.

As shown in FIG. 6, the plasma concentration of injectable carfilzomib SBE-B-CD composition (non-liposomal) declined rapidly following intravenous, bolus administration and was below the limit of quantitation after 1 hour. The half life was about 20 minutes. This is due to rapid and extensive metabolism (FIG. 6, line with open circles).

When delivered in the pL-6 liposomal composition, the duration of exposure to carfilzomib was greatly extended (FIG. 6, solid squares). Plasma concentration of total drug (encapsulated and released) declined slowly and was detectable for up to 24 hours post-dose. This is consistent with the observed delay in proteasome recovery in tissues.

The data for the liposomal CFZ compositions versus CFZ SBE-B-CD (non-liposomal) demonstrate the ability of liposomal compositions to significantly enhance the circulation half-life of peptide epoxyketone compounds. Further, the data show the ability to provide extended duration of exposure to peptide epoxyketone compounds in liposomal compositions versus the non-liposomal SBE-B-CD composition.

Third, the anti-tumor response of injectable carfilzomib formulated in SBE-B-CD (non-liposomal) and the pL-6 liposomal composition comprising liposomes loaded with CFZ was evaluated in mice. Tumors were established by s.c. injection of RL cells (human non-Hodgkin's B cell lymphoma cells; passage number<9 and viability>95% at the time of implantation) in the right flank of beige-nude-XID (BNX) mice (n=8 per group). For RL studies, cell suspensions containing $1 \times 10^7$ cells in a volume of 0.1 mL were injected. Mice were randomized into treatment groups and dosing initiated when tumors reached ~100 mm³ (RL). Tumors were measured thrice weekly by recording the longest perpendicular diameters and tumor volumes were calculated using the equation V (in mm³)=(length×width)/2.

BNX mice bearing established human tumor xenograft derived from RL cells were treated with either non-liposomal carfilzomib or liposomal carfilzomib. Drug was administered on either a weekly (QW) schedule or a schedule of two consecutive daily doses administered each week (QD×2). The group sizes were N=8 mice/group.

The results are presented in FIG. 7 (data up to day 31) and FIG. 8. (data up to day 38, i.e., two additional time points relative to FIG. 7). The data presented in the figures demonstrate that once weekly IV administration (QW) of liposomal composition pL-6 comprising carfilzomib (FIG. 7/FIG. 8, liposomal composition 15 mg/kg, QW, open triangles) and QD×2 administration of liposomal composition pL-6 (FIG. 7/FIG. 8, liposomal composition, 10 mg/kg CFZ, QD×2, solid circles) induced anti-tumor responses similar to injectable carfilzomib formulated in SBE-B-CD (non-liposomal; FIG. 7/FIG. 8, QD×2, 5 mg/kg, open squares) administered on a Day 1/Day 2 schedule (i.e., QD×2). Statistical comparisons between treatment groups and vehicle controls were made by one-way ANOVA and Bonferroni post-hoc analysis (significance was p<0.001). The data presented in both FIG. 7 and FIG. 8 show that the liposomal composition administered at 15 mg/kg once a week was as efficacious as a liposomal or non-liposomal composition administered QD×2.

The data in this example demonstrate that liposomal compositions comprising peptide epoxyketone compounds maintain efficacy at a reduced dosing frequency relative to a non-liposomal composition comprising a peptide epoxyketone compound.

Example 12

Induction of Anti-Tumor Response Using Additional Liposomal Compositions Comprising Entrapped Peptide Epoxyketone A. Composition C The anti-tumor response of injectable carfilzomib formulated in SBE-B-CD (non-liposomal) and the liposomal Composition C comprising liposomes loaded with CFZ was evaluated in mice. Tumors were established by s.c. injection of RL cells (human non-Hodgkin's B cell lymphoma cells; passage number<9 and viability>95% at the time of implantation) in the right flank of BNX mice (n=8 per group). For RL studies, cell suspensions containing $1 \times 10^7$ cells in a volume of 0.1 mL were injected. Mice were randomized into treatment groups and dosing initiated when tumors reached ~100 mm³ (RL). Tumors were measured thrice weekly by recording the longest perpendicular diameters and tumor volumes were calculated using the equation V (in mm³)=(length×width)/2.

BNX mice bearing established human tumor xenograft derived from RL cells were treated with either non-liposomal carfilzomib or liposomal carfilzomib. Drug was administered on either a weekly (QW) schedule or a schedule of two consecutive daily doses administered each week (QD×2). The group sizes were N=8 mice/group.

Figure 9:
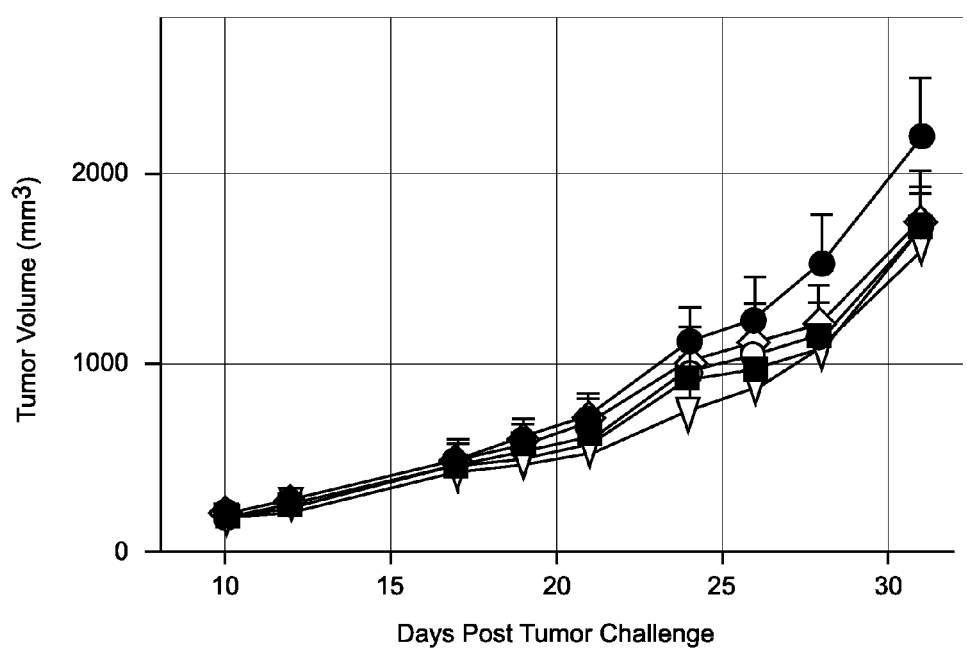
FIG. 9 presents data related to dose and dosing frequency in a mouse xenograft tumor model for a liposomal composition of carfilzomib comprising liposomes comprising entrapped carfilzomib (Composition C; 2 mg/ml CFZ, 12.5 mg/ml EPC). In the figure, the vertical axis is tumor volume in $mm^3$ (Tumor Volume ($mm^3$)), and the horizontal axis is days post-tumor challenge (Days Post Tumor Challenge). The line (top line in the figure at 30 days) with solid circles correspond to once-weekly administration (QW) of vehicle (empty liposomes comprising 12.5 mg/mL EPC); the line with solid squares corresponds to 5 mg/kg of a non-liposomal CFZ composition administered on days 1 and 2 of each week (QD×2). The line with open diamonds corresponds to 5 mg/kg of liposomal Composition C administered on days 1 and 2 of each week (QD×2). The line with open triangles corresponds to 10 mg/kg of liposomal Composition C administered on days 1 and 2 of each week (QD×2). The line with open circles corresponds to 15 mg/kg of liposomal Composition C administered once weekly (QW). Error bars are represented unidirectionally.

The results are presented in FIG. 9. The data presented in the figure demonstrate that once weekly IV administration of liposomal Composition C comprising carfilzomib (FIG. 9, liposomal composition 15 mg/kg, QW, open circles) and QD×2 administrations of liposomal compositions (FIG. 9, liposomal composition, 5 mg/kg, open diamonds, and 10 mg/kg, QD×2, open triangles) induced anti-tumor responses similar to injectable carfilzomib formulated in SBE-B-CD (non-liposomal; FIG. 9, QD×2, 5 mg/kg, solid squares) administered on a Day 1/Day 2 schedule (i.e., QD×2). Statistical comparisons between treatment groups and vehicle controls were made by one-way ANOVA and Bonferroni post-hoc analysis (significance was p<0.001). The data presented in FIG. 9 show that the liposomal composition administered at 15 mg/kg once a week (QW) was as efficacious as a liposomal or non-liposomal composition administered twice weekly (QD×2).

The data in this example demonstrate that liposomal compositions comprising peptide epoxyketone compounds maintain efficacy at a reduced dosing frequency relative to a non-liposomal composition comprising a peptide epoxyketone compound.

B. Composition G

The anti-tumor response of injectable carfilzomib formulated in SBE-B-CD (non-liposomal) and the pegylated liposomal Composition G comprising liposomes loaded with CFZ was evaluated in mice. Tumors were established by s.c. injection of RL cells (human non-Hodgkin's B cell lymphoma cells; passage number<9 and viability>95% at the time of implantation) in the right flank of BNX mice (n=8 per group). For RL studies, cell suspensions containing $1 \times 10^7$ cells in a volume of 0.1 mL were injected. Mice were randomized into treatment groups and dosing initiated when tumors reached ~100 mm³ (RL). Tumors were measured thrice weekly by recording the longest perpendicular diameters and tumor volumes were calculated using the equation V (in mm³)=(length×width)/2.

BNX mice bearing established human tumor xenograft derived from RL cells were treated with either non-liposomal carfilzomib or pegylated liposomal carfilzomib. Drug was administered on either a weekly (QW) schedule or a schedule of two consecutive daily doses administered each week (QD×2). The group sizes were N=8 mice/group.

Figure 10:
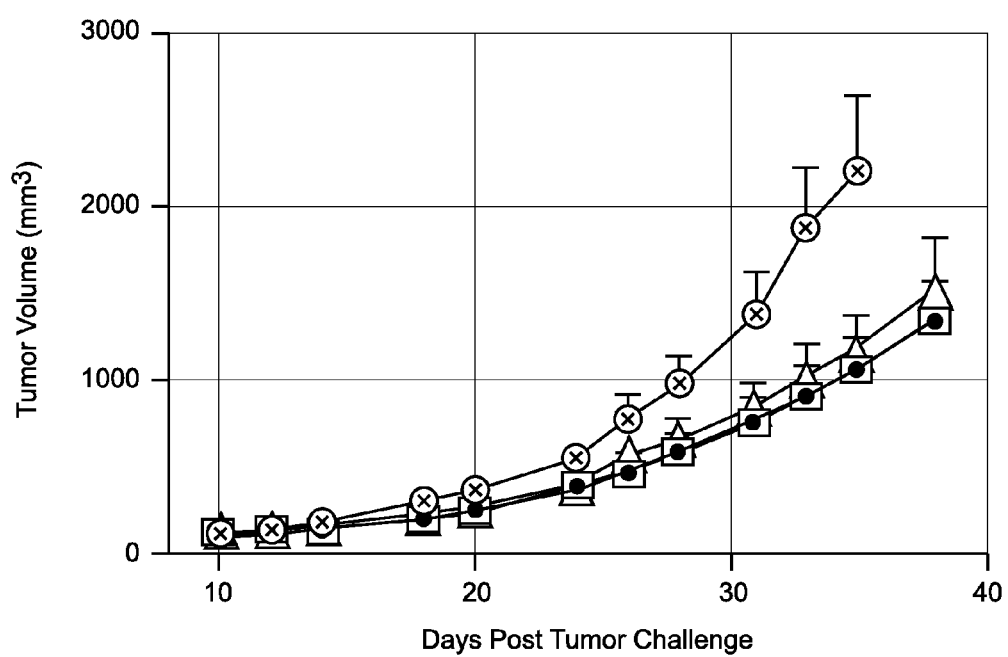
FIG. 10 presents data related to dose and dosing frequency in a mouse xenograft tumor model for a pegylated liposomal composition of carfilzomib comprising liposomes comprising entrapped carfilzomib (Composition G; 2 mg/ml CFZ, 12.5 mg/ml EPC, 1.3 mg/ml mPEG-DSPE, 3.1 mg/ml cholesterol). In the figure, the vertical axis is tumor volume in $mm^3$ (Tumor Volume ($mm^3$)), and the horizontal axis is days post-tumor challenge. The line (top line in the figure at 40 days) with open circles containing an X correspond to once-weekly administration of vehicle (empty liposomes comprising 12.5 mg/mL EPC, 10% mPEG, 25% Cholesterol); the line with open triangles corresponds to 5 mg/kg of a non-liposomal CFZ composition administered on days 1 and 2 of each week. The line with open squares corresponds to 10 mg/kg of liposomal Composition G administered on days 1 and 2 of each week. The line with solid circles corresponds to 15 mg/kg of liposomal Composition G administered once week. Error bars are represented unidirectionally.

The results are presented in FIG. 10. The data presented in the figure demonstrate that once weekly IV administration of liposomal Composition G comprising carfilzomib (FIG. 10, liposomal composition 15 mg/kg, QW, solid circles) and QD×2 administration of the liposomal composition (FIG. 10, liposomal composition, 10 mg/kg, QD×2, open squares) induced anti-tumor responses similar to injectable carfilzomib formulated in SBE-B-CD (non-liposomal; FIG. 10, QD×2, 5 mg/kg, open triangles) administered on a Day 1/Day 2 schedule (i.e., QD×2). Statistical comparisons between treatment groups and vehicle controls were made by one-way ANOVA and Bonferroni post-hoc analysis (significance was p<0.001). The data presented in FIG. 10 show that the liposomal composition administered at 15 mg/kg once a week was as efficacious as a liposomal or non-liposomal composition administered QD×2.

The data in this example demonstrate that liposomal compositions comprising peptide epoxyketone compounds maintain efficacy at a reduced dosing frequency relative to a non-liposomal composition comprising a peptide epoxyketone compound.

Example 13

Exemplary Criteria for Liposomal Compositions Comprising Peptide Epoxyketone Compounds Exemplary criteria for screening and selection of advantageous liposomal compositions comprising peptide epoxyketone compounds include, but are not limited to, the following.

A. Plasma Half-Life/Pharmacokinetic Data

Preferred liposomal compositions of the present invention comprising peptide epoxyketone compounds (e.g., carfilzomib) extend plasma half-life and provide longer duration of exposure relative to non-liposomal compositions comprising peptide epoxyketone compounds (e.g., a non-liposomal composition of carfilzomib formulated in 10% sulfobutylether beta-cyclodextrin and 10 mM Citrate, pH 3.5).

Methods for determination of pharmacokinetic parameters, including plasma half-life ($t_{1/2}$) and area under the plasma concentration time curve (AUC) are described herein (see, e.g., Example 6; Example 9, FIG. 4; Example 11, FIG. 6). Typically, pharmacokinetic parameters are obtained from rodent studies (e.g., using mice or rats). One such screening study to obtain pharmacokinetic parameters is as follows.

Plasma $t_{1/2}$ of a liposomal composition comprising a peptide epoxyketone compound is evaluated in 7-8 week old female BALB/c mice (3-10 mice/time point) following a single i.v. injection of the liposomal composition comprising the peptide epoxyketone compound that is being screened. The liposomal composition is typically administered at one or more drug doses (e.g., over a dose range of 0.5-50 mg/kg of the peptide epoxyketone compound). Additionally, a non-liposomal composition comprising the peptide epoxyketone compound can be included at one or more drug doses for comparison (e.g., over a dose range of 0.5-15 mg/kg of the peptide epoxyketone compound).

The plasma concentration of the peptide epoxyketone compound is evaluated at a number of time points over a selected time period (e.g., as shown in FIG. 4). The half-life of the peptide epoxyketone compound is determined by standard calculations from this data. AUC is determined by measuring drug clearance rates using standard calculations.

B. Pharmacodynamic Profile

Preferred liposomal compositions of the present invention, comprising peptide epoxyketone compounds (e.g., carfilzomib) demonstrate pharmacodynamic profiles comprising (i) at least equivalent or better biodistribution relative to the non-liposomal composition comprising the peptide epoxyketone compound (e.g., carfilzomib), (ii) at least equivalent or better maximum inhibition of chymotrypsin-like (CT-L) activity of 20S proteasome relative to the non-liposomal composition of carfilzomib, and (iii) prolonged inhibition of the CT-L activity in tissues (e.g., preventing complete recovery post dose of CT-L activity relative to vehicle, wherein (a) inhibition of the CT-L activity is observed in one or more selected target tissues (e.g., adrenal tissue), and (b) complete recovery from inhibition of CT-L activity is prevented in one or more selected target tissues (e.g., adrenal tissue) for greater than 4 hours, preferably at least 6 hours post dosing).

Methods for determination of pharmacodynamic data, including biodistribution, maximum CT-L activity inhibition, and prolonged inhibition in tissues are described herein (see, e.g., Example 5, FIG. 2A-2D; Example 8, FIG. 3A-3D; Example 11, FIG. 5A-5D). Typically, pharmacodynamic data are obtained from rodent studies (e.g., using mice or rats). One such study to obtain pharmacodynamic data is as follows.

The pharmacodynamic response of a liposomal composition comprising a peptide epoxyketone compound is evaluated in 7-8 week old female BALB/c mice (3-10 mice/time point) following a single i.v. injection of the liposomal composition (e.g., comprising carfilzomib) that is being screened. The liposomal composition is typically administered at one or more drug doses (e.g., over a dose range of 0.5-50 mg/kg of the peptide epoxyketone compound). Additionally, a non-liposomal composition comprising the peptide epoxyketone compound can be included at one or more drug doses for comparison (e.g., over a dose range of 0.5-15 mg/kg of the peptide epoxyketone compound).

The mice are administered selected drug dose(s) of the liposomal composition. Blood samples and tissues for pharmacodynamic testing are taken at a number of time points over a selected time period (e.g., 0.25-168 hour(s); see, e.g., FIG. 5A-5D) after administration of each dose of the liposomal composition comprising the peptide epoxyketone compound. Typically, a corresponding control liposomal composition without drug is included as a control. The pharmacodynamic response is determined by measurement over time of proteasome activity in blood and tissue (e.g., whole blood (primarily erythrocytes), adrenal tissue, liver tissue, heart tissue, and combinations thereof) using a fluorogenic peptide substrate (LLVY-AMC, as described by Lightcap E S, McCormack T A, Pien C S, et al., *Clin. Chem.* 46:673-683 (2000)) to quantitate the chymotrypsin-like activity of the proteasome. All samples are normalized relative to the appropriate vehicle (i.e., the corresponding composition without carfilzomib). Typically between three and five tissue samples are evaluated per time point for each tissue from each mouse for the chymotrypsin-like activity of the proteasome.

The biodistribution of the liposomal composition is determined based on inhibition of the CT-L activity in each evaluated tissue. The maximum inhibition of CT-L activity is determined relative to the non-liposomal peptide epoxyketone compound. Length of time of inhibition and time of complete recovery of the CT-L activity in tissues (e.g., adrenal tissue) is evaluated based on the tissue samples over time.

C. Anti-Tumor Activity

Preferred liposomal compositions of the present invention, comprising peptide epoxyketone peptides (e.g., carfilzomib) demonstrate anti-tumor activity in a human tumor xenograft model greater than or equal to the non-liposomal composition of the peptide expoxyketone compound (e.g., carfilzomib).

Methods for determination of anti-tumor activity are described herein (see, e.g., Example 11, FIG. 7, FIG. 8; Example 12, FIG. 9, FIG. 10). Typically, anti-tumor data are obtained from human tumor xenograft rodent studies (e.g., using mice or rats). One such study to obtain anti-tumor activity data is as follows.

Anti-tumor activity of a liposomal composition comprising a peptide epoxyketone compound is evaluated in mice.

The liposomal composition is typically administered at one or more drug doses (e.g., over a dose range of 0.5-50 mg/kg of the peptide epoxyketone compound). Additionally, the non-liposomal composition comprising the peptide epoxyketone compound can be included at one or more drug doses for comparison (e.g., over a dose range of 0.5-15 mg/kg of the peptide epoxyketone compound).

Tumors are established by s.c. injection of RL cells (human non-Hodgkin's B cell lymphoma cells; passage number<9 and viability>95% at the time of implantation) in the right flank of BNX mice (n=3-10 per group). For RL studies, cell suspensions containing $1 \times 10^7$ cells in a volume of 0.1 mL are injected. Mice are randomized into treatment groups and dosing is initiated when tumors reach ~100 mm³ (RL). Tumors are measured thrice weekly by recording the longest perpendicular diameters, and tumor volumes are calculated using the equation V (in mm³)=(length×width)/2.

BNX mice bearing established human tumor xenograft derived from RL cells are treated with the liposomal composition comprising the peptide epoxyketone compound. Typically, a non-liposomal composition comprising the peptide epoxyketone compound is included at one or more drug doses for comparison (e.g., over a dose range of 2-15 mg/kg of the peptide epoxyketone compound). Drug is typically administered on a weekly (QW) schedule and/or a schedule of two consecutive daily doses administered each week (QD×2). Tumors are measured and tumor volume is determined at a number of time points (e.g., as shown in FIG. 8) over a selected time period (e.g., 1-100 day(s)) after administration of the liposomal composition comprising the peptide epoxyketone compound. Typically, a corresponding control liposomal composition without drug is included as a control. The anti-tumor activity for the compositions is determined by measurement over time of tumor volume.

Statistical comparisons between treatment groups and vehicle controls are typically made by one-way ANOVA and Bonferroni post-hoc analysis.

As is apparent to one of skill in the art, various modification and variations of the above embodiments can be made without departing from the spirit and scope of this invention. Such modifications and variations are within the scope of this invention.

What is claimed is:

1. A pharmaceutical liposomal composition comprising:
   an aqueous solution comprising liposomes; and
   the liposomes comprising
   (i) between about 0.5 wt. % and about 50 wt. % of carfilzomib, wherein the carfilzomib is entrapped in the liposomes;
   (ii) between about 99.5 wt. % and about 50 wt. % total lipids, wherein the total lipids comprise a phospholipid selected from the group consisting of L-α-phosphatidylcholine; 1,2-distearoyl-sn-glycero-3-phosphocholine; 1,2-dipalmitoyl-sn-glycero-3-phosphocholine; 1,2-Distearoyl-sn-glycero-3-phospho-rac-(1-glycerol); 1-Palmitoyl-2-oleoyl-sn-glycero-3-phosphocholine; sphingomyelin; 1,2-distearoyl-sn-glycero-3-phosphoethanolamine; and combinations thereof;
   wherein the liposomes have an average size of between about 0.05 microns and about 0.5 microns, and the carfilzomib is present in the composition in a concentration between 1 mg/ml and 2 mg/ml.

2. The pharmaceutical liposomal composition of claim 1, wherein the phospholipid comprises L-α-phosphatidylcholine.

3. The pharmaceutical liposomal composition of claim 1, wherein the total lipids comprise between about 30 wt. % and about 90 wt. % of the phospholipid.

4. The pharmaceutical liposomal composition of 1, wherein the total lipids further comprise a hydrophilic polymer-derivatized lipid.

5. The pharmaceutical liposomal composition of claim 4, wherein the total lipids comprise between about 8 wt. % and about 20 wt. % of the hydrophilic polymer-derivatized lipid.

6. The pharmaceutical liposomal composition of claim 4, wherein the hydrophilic polymer-derivatized lipid comprises a hydrophilic polymer and a lipid, and the hydrophilic polymer is a polyethylene glycol.

7. The pharmaceutical liposomal composition of claim 6, wherein the lipid of the hydrophilic polymer-derivatized lipid is cholesterol or a phospholipid.

8. The pharmaceutical liposomal composition of claim 1, wherein the total lipids further comprise a cholesterol or cholesterol derivative.

9. The pharmaceutical liposomal composition of claim 8, wherein the total lipids comprise between about 15 wt. % and about 30 wt. % of the cholesterol or cholesterol derivative.

10. The pharmaceutical liposomal composition of claim 8, wherein the total lipids further comprise a hydrophilic polymer-derivatized lipid.

11. The pharmaceutical liposomal composition of claim 10, wherein the total lipids comprise between about 83.3 wt. % of the phospholipid and about 57 wt. % of the phospholipid, between about 8.33 wt. % of the hydrophilic polymer-derivatized lipid and about 14 wt. % of the hydrophilic polymer-derivatized lipid, and between about 8.33 wt. % of the cholesterol or cholesterol derivative and about 29 wt. % of the cholesterol or cholesterol derivative.

12. The pharmaceutical liposomal composition of claim 1, comprising between about 1 wt. % and about 25 wt. % carfilzomib, and between about 99 wt. % and about 75 wt. % of the total lipids.

13. The pharmaceutical liposomal composition of claim 1, wherein the average size of the liposomes is selected from the group consisting of: between about 0.05 microns and about 0.15 microns; and between about 0.05 microns and about 0.10 microns.

14. The pharmaceutical liposomal composition of claim 1, wherein the liposomes comprises carfilzomib and a solubilizing agent in an internal aqueous core of the liposomes.

15. The pharmaceutical liposomal composition of claim 14, wherein the solubilizing agent is sulfobutylether-beta-cyclodextrin, and the liposomes of the liposomal composition comprise carfilzomib complexed with the cyclodextrin in the internal aqueous core of the liposomes.

16. A pharmaceutically acceptable liposome comprising:
   (i) between about 0.5 wt. % and about 50 wt. % carfilzomib; and
   (ii) between about 99.5 wt. % and about 50 wt. % total lipids, wherein the total lipids comprise a phospholipid selected from the group consisting of L-α-phosphatidylcholine; 1,2-distearoyl-sn-glycero-3-phosphocholine; 1,2-dipalmitoyl-sn-glycero-3-phosphocholine; 1,2-Distearoyl-sn-glycero-3-phospho-rac-(1-glycerol); 1-Palmitoyl-2-oleoyl-sn-glycero-3-phosphocholine; sphingomyelin; 1,2-distearoyl-sn-glycero-3-phosphoethanolamine; and combinations thereof.

17. The pharmaceutically acceptable liposome of claim 16, wherein the total lipids comprise between about 30 wt. % and about 90 wt. % of the phospholipid.

18. The pharmaceutically acceptable liposome of claim 16, wherein the total lipids further comprise a hydrophilic polymer-derivatized lipid.

19. The pharmaceutically acceptable liposome of claim 16, wherein the total lipids further comprise a cholesterol or cholesterol derivative.

20. The pharmaceutically acceptable liposome of claim 16, wherein the total lipids comprise between about 83.3 wt. % of the phospholipid and about 57 wt. % of the phospholipid, between about 8.33 wt. % of a hydrophilic polymer-derivatized lipid and about 14 wt. % of a hydrophilic polymer-derivatized lipid, and between about 8.33 wt. % of a cholesterol or cholesterol derivative and about 29 wt. % of the cholesterol or cholesterol derivative.

21. The pharmaceutically acceptable liposome of claim 16, comprising between about 1 wt. % and about 25 wt. % of carfilzomib, and between about 99 wt. % and about 75 wt. % of the total lipids.

22. The pharmaceutically acceptable liposome of claim 16, further comprising sulfobutylether-betacyclodextrin.

23. The pharmaceutically acceptable liposome of claim 16, further comprising one or more additional excipients selected from the group consisting of a cryoprotectant agent, a sugar, a glass transition modifying agent selected from the group consisting of a sugar, a polyol, a polymer, an amino acid, and combinations thereof, and a combination of any of the foregoing.

24. A method of treating multiple myeloma in a subject in need of treatment, comprising:
administering a therapeutically effective amount of a pharmaceutical liposomal composition of claim 1 to the subject.

25. The method of claim 24, further comprising simultaneous, sequential, or separate administration of a therapeutically effective amount of a chemotherapeutic agent, a cytokine, a steroid, or an immunotherapeutic agent.

26. The pharmaceutical liposomal composition of claim 1, wherein the carfilzomib is present in the composition in a concentration of 2 mg/ml.

* * * * *